US010081841B2

(12) United States Patent
Mitchell et al.

(10) Patent No.: US 10,081,841 B2
(45) **Date of Patent: *Sep. 25, 2018**

(54) DETECTING FETAL CHROMOSOMAL ABNORMALITIES USING TANDEM SINGLE NUCLEOTIDE POLYMORPHISMS

(71) Applicant: University of Louisville Research Foundation, Inc., Louisville, KY (US)

(72) Inventors: Aoy Tomita Mitchell, Elm Grove, WI (US); Michael Mitchell, Elm Grove, WI (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/082,934

(22) Filed: Nov. 18, 2013

(65) Prior Publication Data

US 2014/0099640 A1 Apr. 10, 2014

Related U.S. Application Data

(63) Continuation of application No. 12/689,924, filed on Jan. 19, 2010, now Pat. No. 8,609,338, which is a continuation-in-part of application No. 11/713,069, filed on Feb. 28, 2007, now Pat. No. 7,799,531.

(60) Provisional application No. 60/777,865, filed on Feb. 28, 2006.

(51) Int. Cl.
*C12Q 1/68* (2018.01)
*C12Q 1/6883* (2018.01)

(52) U.S. Cl.
CPC ..... *C12Q 1/6883* (2013.01); *C12Q 2600/156* (2013.01); *C12Q 2600/158* (2013.01); *C12Q 2600/172* (2013.01)

(58) Field of Classification Search
None
See application file for complete search history.

(56) References Cited

U.S. PATENT DOCUMENTS

| | | | | |
|---|---|---|---|---|
| 6,258,540 | B1 | 7/2001 | Lo et al. | |
| 6,979,541 | B1 | 12/2005 | Pont-Kingdon et al. | |
| 7,799,531 | B2 * | 9/2010 | Mitchell et al. | 435/6.12 |
| 8,399,195 | B2 * | 3/2013 | Mitchell et al. | 435/6.11 |
| 8,609,338 | B2 * | 12/2013 | Mitchell | C12Q 1/6883 435/6.1 |
| 8,663,921 | B2 * | 3/2014 | Mitchell | C12Q 1/6883 435/6.1 |
| 9,181,586 | B2 * | 11/2015 | Mitchell | C12Q 1/6883 |
| 2001/0048756 | A1 | 12/2001 | Staub et al. | |
| 2003/0082606 | A1 | 5/2003 | Lebo et al. | |
| 2003/0211522 | A1 | 11/2003 | Landes et al. | |
| 2004/0137452 | A1 | 7/2004 | Levett et al. | |
| 2004/0137470 | A1 | 7/2004 | Dhallan | |
| 2005/0049793 | A1 | 3/2005 | Paterlini-Brechot | |
| 2005/0164241 | A1 | 7/2005 | Hahn et al. | |
| 2006/0121452 | A1 | 6/2006 | Dhallan | |
| 2006/0160105 | A1 | 7/2006 | Dhallan | |
| 2007/0207466 | A1 | 9/2007 | Cantor et al. | |
| 2008/0318235 | A1 | 12/2008 | Handyside | |

FOREIGN PATENT DOCUMENTS

| | | |
|---|---|---|
| WO | WO 00/34652 | 6/2000 |
| WO | WO 02/068685 | 9/2002 |
| WO | WO 03/062441 | 7/2003 |
| WO | WO 04/078999 | 9/2004 |
| WO | WO 04/079011 | 9/2004 |
| WO | WO 05/023091 | 3/2005 |
| WO | WO 05/035725 | 4/2005 |
| WO | WO 05/044086 | 5/2005 |
| WO | WO 06/011738 | 2/2006 |
| WO | WO 2011/057094 | 5/2011 |

OTHER PUBLICATIONS

Adams, K. et al., Microchimerism an investigative Frontier in Autoimmunity and Transplantation. JAMA. 2004, 291 (9): P-1127-1131.
Andonova, S., et al., Introduction of the QF-PCR analysis for the purposes of prenatal diagnosis in Bulgaria—estimation of applicability of 6 STR markers on chromosomes 21 and 18. Prenat. Diagn., 2004. 24(3): p. 202-208.
Andre et al., "Fidelity and Mutational Spectrum of Pfu DNA Polymerase on a Human Mitochondrial DNA Sequence," Genome Res., 1997, 7: 843-852.
Antonarakis et al., Analysis of DNA haplotypes suggests a genetic predisposition to trisomy 21 associated with DNA sequences on chromosome 21, PNAS, 82(10), 3360-3364 (1985).
BBC News, Safer test for unborn babies hope. BBC News Oct. 4, 2005. htt://news.bbc.co.uk/2/hi/health/4307628.stm.
Birch, L., et al., Accurate and Robust Quantification of Circulating Fetal and Total DNA in Maternal Plasma from 5 to 41 Weeks of Gestation. Clin_ Chem., 2005. 51(2): p. 312-320.
Chim, S.C., et al., Detection of the placental epigenetic signature of the maspin gene in maternal plasma, PNAS 2005, 102(41): p. 14753-14758.
Cline, J. et al., PCR fidlity of Pfu polymerase and other thermostable DNA polymerases, Nucleic Acids Res. 1996, 24(18): p. 3546-3551.
Database SNP (Online) Retrieved from NCBI Database Accession No. rs2822654 Abstract (2004).
Dhallan, R. et al., Methods to Increase the Percentage of Free Fetal DNA Recovered From the Maternal Circulation. JAMA, 2004. 291 (9): p. 1114-1119.
Dhallan, R., et al., A non-invasive test for prenatal diagnosis based on fetal DNA present in maternal blood: a preliminary study. www.thelancet.com 2007. DOl:10.1016/S0140-6736(07)60115-9.
Ding, C. et al., MS Analysis of single nucleotide differences in circulating nucleic acids: Application to noninvasive prenatal diagnosis. PNAS, 2004, 101 (29): p. 10762-10767.
HOWDY Database, Human Organized Whole Genome Database, Marker 5618, NM_003895, available via url: <howdy .jst.go.j p/HOWDYCU/HOW DY. pl?Cls Marker&Key=U KEY & Val+ 5618>.

(Continued)

*Primary Examiner* — Carla J Myers
(74) *Attorney, Agent, or Firm* — Fish & Richardson P.C.

(57) ABSTRACT

The invention provides tandem single nucleotide polymorphisms and methods for their use, for example, in diagnosing Down Syndrome.

7 Claims, 2 Drawing Sheets

Specification includes a Sequence Listing.

(56) References Cited

OTHER PUBLICATIONS

Human Chromosome 21 cSNP database, University of Geneva. Swiss Institute of Bioinformatics, HC21 S00131, available via url: <csnp.unige.ch/cgibin/csnp fetch?db=csnp&format=htmol&entry=HC21 G00062>.
Human Chromosome 21 cSNP database, University of Geneva. Swiss Institute of Bioinfomatics, HC21 S00027, available via url: <csnp.unige.ch/cgibin/csnp_fetch?db=csnp&format=html&entry=HC21 G00018>.
Illanes et al., Prenatal Diagnosis, 2006. 26: 1216-1218.
International Search Report for International Application No. PCT/US2007/005399 (dated 2007).
Khrapko, K., et al., Constant denaturant capillary electrophoresis (CDCE): a high resolution approach to mutational analysis. Nucleic Acids Res., 1994. 22(3): p. 364-369.
Lerman, L.S. et al., Computational simulation of DNA melting and its application to denaturing gradient gel electrophoresis. Methods Enzymol., 1987. 155: p. 482-501.
Li et al., Journal of the Society for Gynecologic Investigation. 2003. 10: 503-508.
Li, Y. et al., Detection of Paternally Inherited Fetal Point Mutations for {3-Thalessemia Using Size Fractionated Cell-Free DNA in Maternal Plasma. JAMA., 2005. 293(7): p. 843-9. Corr: jama, 2006. 293(14): p. 1728.
Li, Y. et al., Size Separation of Circulatory DNA in Maternal Plasma Permits Ready Detection of Fetal DNA Polymorphisms. Clin. Chem., 2004. 50(6): p. 1002-1011.
Lim, E.I. et al., Combination of Competitive Quantative PCR and Conatant Denaturant Capillary Electrophoresis for High-resolution Detection and Enumeration of Microbial Cells. 2001. Appl. Environ. Microbiol. 67(9): p. 3897-3903.
Li-Sucholeiki, X.C. et al., A sensitive scanning technology for low frequency nuclear point mutations in human genomic DNA. Nucleic Acids Res., 2000. 28(9): p. E44. (8 pages).
Lo, Y.M.D. et al., Free Fetal DNA in Maternal Circulation. 2004. JAMA 292(23): p. 2835-2836.
Lo, Y.M.D. et al., Increased Fetal DNA Concentrations in the Plasma of Pregnant Women Carrying Fetuses with Trisomy 21. Clin. Chem., 1999. 45(10): p. 1747-1751.
Lo, Y.M.D. et al., Quantitative analysis of Fetal DNA in Maternal Plasma and Serum: Implications for Noninvasive Prenatal Diagnosis. Am J. Hum. Genet., 1998. 62(4): p. 768-775.
Malone, F.D. et al., First-trimester sonographic screening for Down syndrome. Obstet. Gynecol., 2003. 102(5Pt1): p. 1066-1079.
Nagy et al., Rapid determination of trisomy 21 from amniotic fluid cells using single nucleotide polymorphic loci, Prenat. Diagn., 25(12). 1138-1141 (2005).
Parsons, B. et al., Genotypic selection methods for the direct analysis of point mutations. Mutation Research, 1997. 387: p. 97-121.
Pertl, B., et al., Detection of male and female fetal DNA in maternal plasma by multiplex fluorescent polymerase chain reaction amplification of short tandem repeats. Hum. Genet., 2000. 106: p. 45-49.
Pont-Kingdon et al., Direct molecular haplotyping by melting curve analysis of hybridization probes: beta 2-adrenergic receptor haplotypes as an example, Nucleic Acids Res., 33(10). e89 (2005).
Poon, L.M. et al., Differential DNA Methylation between Fetus and Mother as a Strategy for Detecting Fetal DNA in Maternal Plasma. Clin. Chem., 2002. 48(1): p. 35-41.
Puers, C., et al., Identification of Repeat Sequence Heterogeneity at the Polymorphic Short Tandem Repeat Locus HUMTH01 [AA TG]n and Reassignment of Alleles in Population Analysis by Using a Locus-specific Allelic Ladder, Am. J. Hum. Genet. 53:953-958, 1993.
Samu Ra, 0. et al., Diagnosis of Trisomy 21 in Fetal Nucleated Erythrocytes from Maternal Blood by Use of Short Tandem Repeat Sequences. Clin. Chem., 2001. 47(9): p. 1622-1626.
Simpson, J.L. et al., Cell-Free Fetal DNA in Maternal Blood: Evolving Clinical Applications. JAMA, 2004. 291(9): p. 1135-1137.
The EMBL-EBI Database. EBI Dbfetch, Accession No. F239726, Mar. 22, 2000.
The Free Dictionary definition for "Aneuploidy", available via url: <medical-dictionary.thefreedictionary.com/aneuploidy>, printed Aug. 26, 2013.
The International Hap Map Consortium, A haplotype map of the human genome. Nature, 2005.437. p. 1299-1320.
The International HapMap Consortium, The International HapMap Project. Nature, 2003. 426. p. 789-796.
Thompson, J.R., et al., Heteroduplexes in mixed-template amplifications: formation consequence and elimination by 'reconditioning PCR', Nucleic Acids Res., 2002. 30(9): p. 2083-2088.
Thorisson, G.A., et al., The International HapMap Project Web site. Genome Res., 2005. 15: p. 1592-1593.
Wald, N.J., et al., Antenatal screening for Down's syndrome with the quadruple test. Lancet, 2003. 361 (9360): p. 835-836.
Zheng, W. et al., Origins fo human mitochondrial point mutations as DNA polymerase y mediated errors, Mutat. Res., 2006. 599(1-2): p. 11-20.
Zhong et al., Annals NY Acad Sci. 2006, 945: 250-257.

* cited by examiner

DETECTING FETAL CHROMOSOMAL ABNORMALITIES USING TANDEM SINGLE NUCLEOTIDE POLYMORPHISMS

CROSS REFERENCE TO RELATED APPLICATIONS

This application is a continuation of U.S. Ser. No. 12/689,924, filed Jan. 19, 2010, which is a continuation-in-part of U.S. patent application Ser. No. 11/713,069, filed Feb. 28, 2007, which claims the benefit of priority of U.S. Provisional Patent Application No. 60/777,865, filed Feb. 28, 2006, each of which is hereby incorporated by reference in its entirety.

BACKGROUND

About 6.4 million women become pregnant in the U.S. each year, and about 70% of those women have maternal serum screening and/or an ultrasound test in an attempt to determine risks for common birth defects, such as those resulting from trisomy 13, 18, and 21 (Down Syndrome). Both the sensitivity and specificity of these common non-invasive screening tools are extremely poor. The best current non-invasive tests lead to a false positive rate between 7 and 20%. This high false positive rate has two catastrophic consequences for American families and society. First, it creates a large market for the two invasive diagnostic tests, chorionic villus sampling (CVS) and amniocentesis, which each carry a fetal loss rate of 0.5%-1%. These invasive tests directly result in the loss of thousands of normal fetuses annually. Second, the high false positive rate heightens maternal anxiety and stress in the large and fixed proportion of pregnant American women who receive false positive results. However, prenatal diagnosis are critical in managing a pregnancy with chromosomal abnormalities and localized genetic abnormalities, as the diagnosis can allow for interventional care during delivery and can prevent devastating consequences for the neonate. Non-invasive tests that rely on detection of short tandem repeat (STR) sequences and low complexity regions have low-sensitivity and are often riddled with false-positives and false-negatives. STR sequences and low complexity regions are highly susceptible to polymerase-induced stutters and therefore generate significant PCR-induced noise. This high background noise makes the detection and accurate quantification of low concentrations of fetal DNA in maternal plasma very unlikely, making these poor markers for use in non-invasive tests for fetal chromosomal abnormalities. Thus there is a tremendous need for the development of a sensitive and specific non-invasive test for chromosomal abnormalities, e.g., for prenatal diagnostics.

SUMMARY OF CERTAIN EMBODIMENTS OF THE INVENTION

Accordingly, certain embodiments of the present invention provide a method for determining whether a fetus has at least one chromosomal abnormality, comprising using tandem single nucleotide polymorphisms to compare fetal DNA to maternal DNA so as to determine whether the fetus has at least one chromosomal abnormality.

BRIEF DESCRIPTION OF THE FIGURES

FIG. 3A illustrates the output that may result from a maternal buccal swab, which will comprise maternal nucleic acids but no fetal nucleic acids (upper graphs), and from a sample comprising fetal DNA but no maternal DNA, where the fetus has trisomy (lower graphs). As shown in FIG. 3A, a maternal buccal swab would be expected to show a 1:1 ratio for markers for which the maternal genome is heterozygous. The lower graphs in FIG. 3A illustrate that fetal output would show a ratio of 1:1:1 or 2:1. FIG. 3B illustrates the output that results from a sample comprising both maternal and fetal nucleic acids, where the fetus has trisomy. In this case, the output will either show two peaks of equal area and a third smaller peak or three peaks with different areas, where the areas are in a ratio of peak:x:peak+2x, where “x” represents the number of molecules of the allele inherited by the fetus from the father. FIG. 3C illustrates the output that results from a sample comprising both maternal and fetal nucleic acids, where the fetus is normal. Again, three alleles will be detected, and the peaks will be of different areas, but in this situation, the ratio of the peaks will be peak:x:peak+x.

DETAILED DESCRIPTION

Figure 1:
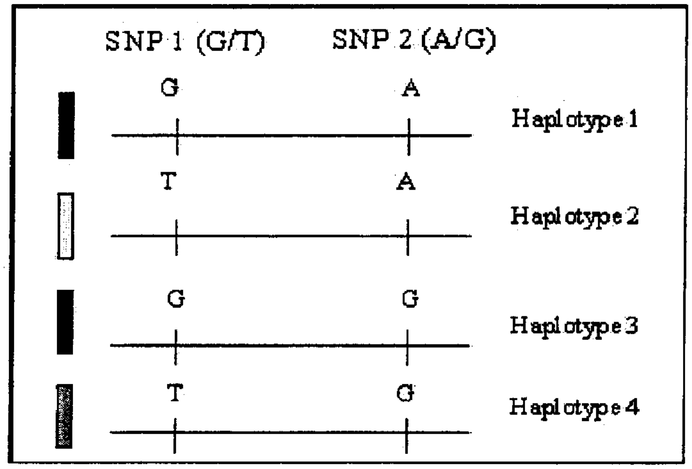
FIG. 1 depicts an example of a tandem SNP.

For years, it has been hoped that the use of fetal cells in maternal blood might be used to assess the genetic status of a developing embryo. Unfortunately, the extremely small amount of fetal cells in maternal blood (about 1 cell per ml) has proven a difficult obstacle to overcome when trying to isolate these cells for widespread clinical testing. However, cell-free fetal DNA is present in circulating maternal serum at higher percentages than fetal cells and has the potential to be assessed for chromosomal or gene defects. Cell-free fetal DNA can range from 1-47/of total DNA in maternal blood. However, a critical limitation that has yet to be successfully overcome is that maternal DNA contamination makes it difficult to differentiate fetal from maternal DNA.

As described herein, this limitation has been overcome by identifying tandem single nucleotide polymorphisms (SNPs) to detect chromosomes, e.g., to detect fetal chromosomal abnormalities. The tandem SNPs are combined with a sensitive DNA separation technology, e.g., high-fidelity PCR and constant denaturant capillary electrophoresis (CDCE), to detect fetal chromosomal abnormalities, e.g., through the simple sampling and comparison of maternal DNA to fetal DNA, e.g., from maternal serum and maternal buccal swabs. This approach substantially eliminates false positives and significantly reduces false negatives.

Accordingly, certain embodiments of the present invention provide a method for determining whether a fetus has at least one chromosomal abnormality, comprising using tandem single nucleotide polymorphisms to compare fetal DNA to maternal DNA so as to determine whether the fetus has at least one chromosomal abnormality.

In certain embodiments of the invention, fetal DNA is obtained from maternal blood. In certain embodiments of the invention, fetal DNA is cell-free fetal DNA. In certain embodiments of the invention, maternal DNA is obtained from a biological sample, e.g., maternal blood. In certain embodiments of the invention, maternal DNA is obtained from a buccal swab. In certain embodiments of the invention, maternal DNA is obtained from a biological sample that does not comprise fetal DNA.

In certain embodiments of the invention, fetal DNA is obtained from maternal blood, maternal urine, maternal sweat, maternal cells, or cell free DNA from the mother.

In certain embodiments, the biological sample is biological fluid. In certain embodiments, the biological sample is a maternal biological sample. In certain embodiments, samples may be whole blood, bone marrow, blood spots, blood serum, blood plasma, buffy coat preparations, saliva, cerebrospinal fluid, buccal swabs, solid tissues such as skin and hair, body waste products, such as feces and urine. In other embodiments, samples may be lysates, homogenates, or partially purified samples of biological materials. In other instances, biological materials can include crude or partially purified mixtures of nucleic acids. In certain embodiments, the biological sample is serum, urine, sweat, cells, or cell free DNA.

In certain embodiments of the invention, the comparison step comprises using high-fidelity PCR and constant denaturant capillary electrophoresis to compare the fetal DNA to maternal DNA. In certain embodiments of the invention, the comparison step comprises using at least about 96 tandem single nucleotide polymorphisms.

In certain embodiments of the invention, the method further comprises the step of converting the nucleic acid molecules to a homoduplex state, as opposed to being in heteroduplex form. This can be accomplished, e.g., by using an excess of primers and can aid in the tandem SNP analysis.

In certain embodiments of the invention, methods such as mutation detection technologies can be used to analyze the tandem SNPs. In certain embodiments of the invention, methods such as denaturing HPLC, denaturing capillary electrophoresis, cycling temperature capillary electrophoresis, allele-specific PCRs, quantitative real time PCR approaches such as TaqMan® PCR system, polony PCR approaches, and microarray approaches can be used to analyze the tandem SNPs.

In certain embodiments of the invention, the single nucleotide polymorphisms in each tandem single nucleotide polymorphism are each at most about 250 basepairs apart. In certain embodiments of the invention, the single nucleotide polymorphisms in each tandem single nucleotide polymorphism are each at most about 200 basepairs apart. In certain embodiments of the invention, the single nucleotide polymorphisms in each tandem single nucleotide polymorphism are each at most about 150 basepairs apart. In certain embodiments of the invention, the single nucleotide polymorphisms in each tandem single nucleotide polymorphism are each at most about 100 basepairs apart. In certain embodiments of the invention, the single nucleotide polymorphisms in each tandem single nucleotide polymorphism are each at most about 50 basepairs apart.

In certain embodiments of the invention, at least one tandem single nucleotide polymorphism is located on the p arm of chromosome 21. In certain embodiments of the invention, at least one tandem single nucleotide polymorphism is located on the q arm of chromosome 21.

In certain embodiments of the invention, the chromosomal abnormality is chromosomal aneuploidy. In certain embodiments of the invention, the chromosomal abnormality is trisomy 13, 18 or 21. In certain embodiments of the invention, the chromosomal abnormality is trisomy 21.

In certain embodiments of the invention, the chromosomal abnormality is an insertion mutation (e.g., a large insertion (≥3 megabasepair) or small insertion (<3 megabasepair). In certain embodiments of the invention, the chromosomal abnormality is a deletion mutation (e.g., a large deletion (≥3 megabasepair) or small deletion (<3 megabasepair)). The deleted region could include a deleted gene.

In certain embodiments of the invention, the methods can be used to detect copy number polymorphisms and/or copy number variants in the genome. In certain embodiments of the invention, the methods can be used to detect chromosome 22q11 deletion syndrome, which is associated with cardiac defects.

Chromosomal abnormalities include deletions associated with genetic syndromes and disorders such as the 22q11 deletion syndrome on chromosome 22, which is associated with cardiac defects. Other examples of chromosomal abnormalities include the 11q deletion syndrome on chromosome 11 and 8p deletion syndrome on chromosome 8, both of which are also associated with cardiac defects.

In certain embodiments of the invention, the fetus is a male fetus. In certain embodiments of the invention, the fetus is a female fetus. In certain embodiments of the invention, the fetus is a mammal. In certain embodiments of the invention, the fetus is a human. In certain embodiments of the invention, the fetus is a non-human mammal. In certain embodiments of the invention, the fetus has been determined to be at an elevated risk for having a chromosomal abnormality.

In certain embodiments of the invention, the method further comprises using tandem single nucleotide polymorphisms to compare paternal DNA to the fetal and/or maternal DNA.

In certain embodiments of the invention, the fetal DNA is subjected to an enrichment step. In certain embodiments of the invention, the fetal DNA is not subjected to an enrichment step.

Certain embodiments of the present invention provide a method for identifying chromosomes, comprising comparing tandem single nucleotide polymorphisms on the chromosomes so as to identify the chromosomes. Thus, the methods of the present invention are not limited to maternal-fetal analysis, but can also be applied to other situations, e.g., forensic analysis of blood samples.

In certain embodiments of the invention, the methods further comprises, prior to the comparison step, determining a set of tandem single nucleotide polymorphisms for a specific chromosome.

Certain embodiments of the present invention provide a system comprising packaging material and primers that specifically hybridize to each of the single nucleotide polymorphisms of at least one of the tandem single nucleotide polymorphisms identified herein.

Certain embodiments of the present invention provide a system comprising packaging material and primers that specifically hybridize flanking sequences of at least one of the tandem single nucleotide polymorphisms of the invention.

Certain embodiments of the present invention provide a system comprising packaging material and at least one oligonucleotide that specifically hybridizes to at least one of the tandem single nucleotide polymorphisms of the invention.

Certain embodiments of the present invention provide the use of high-fidelity PCR (HiFi-PCR) to amplify SNPs or tandem SNPs for the purpose of, e.g., determining chromosomal abnormalities.

Certain embodiments of the present invention provide the use of HiFi-PCR to amplify nucleic acids, e.g., DNA, isolated, e.g., from a maternal biological sample to analyze fetal DNA for chromosomal abnormalities.

In certain embodiments, HiFi-PCR is used to detect aneuploidy and large (≥3megabasepairs) or small (<3 megabasepairs) deletions and/or insertions.

In certain embodiments, the maternal biological sample is serum, urine, sweat, cells, or cell free DNA.

Certain embodiments of the present invention provide an isolated nucleic acid sequence comprising at least one of SEQ ID NOs 1-357.

Certain embodiments of the present invention provide an isolated nucleic acid sequence of the invention (e.g., a nucleic acid sequence comprising a tandem SNP or a primer; e.g., at least one of SEQ ID NOs 1-357) for use in medical treatment or diagnosis.

In certain embodiments, the nucleic acid sequences may be, e.g., isolated nucleic acid sequences and may be, e.g., about 1000 or fewer, e.g., about 900 or fewer, e.g., about 800 or fewer, e.g., about 700 or fewer, e.g., about 600 or fewer, e.g., about 500 or fewer, e.g., about 400 or fewer, e.g., about 300 or fewer, e.g., about 250 or fewer, e.g., about 200 or fewer, e.g., about 150 or fewer, e.g., about 100 or fewer, or e.g., about 50 or fewer nucleic acids in length.

Thus, short haplotypes are used to detect fetal chromosomal abnormalities in maternal serum, e.g., for the most common of these defects, trisomy 21. To demonstrate this method, tandem SNPs for chromosome 21 are identified, heterozygosity of the tandem SNPs determined, the ability to detect fetal DNA from maternal serum demonstrated, and the ability to detect fetal chromosomal abnormalities in maternal serum demonstrated. 118 tandem SNPs have already been identified. These tandem SNPs are useful in the diagnosis of chromosomal abnormalities, for example, of trisomy 21. Thus, certain embodiments of the invention provide the specific tandem SNPs, or combinations thereof, as well as their use in diagnostic and therapeutic applications.

The output of these experiments, e.g., assays based on a set of tandem SNPs for chromosome 21, can be used in the clinic as an alternative to invasive diagnostic tests like amniocentesis and CVS, using, e.g., CDCE or other techniques capable of detecting the tandem SNPs. These diagnostics are sensitive and specific. The tandem SNP assay is particularly suited for fetal DNA analysis because fetal DNA present in maternal serum is generally present as short fragments (e.g., an average of 300 basepairs or fewer).

Thus, certain embodiments of the present invention are directed to each of these tandem SNPs individually, and certain embodiments are directed to combinations of any and/or all of the tandem SNPs. Certain embodiments of the invention are directed to methods of using the tandem SNPs for diagnosing chromosomal abnormalities. Certain embodiments of the invention are directed to compilations of the tandem SNPs (e.g., reference tables) that are useful for diagnosing chromosomal abnormalities. Certain embodiments of the invention are also directed to primers for each of these tandem SNPs individually, and certain embodiments are directed to combinations of primers for any and/or all of the tandem SNPs. Certain embodiments of the invention provide isolated nucleic acid sequences that comprise at least one of the tandem SNPs and compositions that comprise the isolated nucleic acid sequences.

Prenatal Screening

An increasing number of fetal medical conditions can be successfully managed during the neonatal period if an early diagnosis is made. A variety of prenatal screening tools are available for chromosomal and birth defects. The two most commonly utilized non-invasive tools are ultrasound and measurements of maternal serum markers. Both of these "tests" have inadequate sensitivity and specificity for screening the most common of the defects, Down Syndrome (trisomy 21).

An ultrasound screening called the nuchal translucency test is becoming more common. However, this test has an overall sensitivity of 77% for trisomy 21 with a false positive rate of 6% (Malone et al., Obstet Gynecol, 2003. 102(5 Pt 1): p. 1066-79). The most advanced serum marker test is the "quad" screen, which measures the levels of alpha-fetoprotein (AFP), human chorionic gonadotropin (hCG), unconjugated estriol (E3), and inhibin-A. The biological reason for these markers to be elevated or reduced in a percentage of mothers carrying children with trisomy 21 is not understood. Further, the test is only capable of assigning risk categories (i.e., 1 in 250, 1 in 100, 1 in 10), and not in making specific diagnoses. The quad screen is associated with a false positive rate of 7% and a sensitivity of less than 80%, rates which do not approach those achieved by invasive prenatal diagnostic tests (Wald et al., Lancet, 2003. 361(9360): p. 835-6).

Because of the inadequate sensitivity and specificity of currently available non-invasive tools, amniocentesis and chorionic villus sampling (CVS), both invasive procedures, remain the standard for the definitive detection of fetal chromosomal abnormalities. Both of these procedures carry a 0.5%-1% fetal loss rate, which translate into the death of thousands of normal fetuses annually. To solve this problem and meet the overwhelming need for an accurate non-invasive test, several strategies have been previously proposed by other investigators. However, those studies have been limited by their ability to detect and differentiate fetal DNA from maternal DNA.

A PCR-based approach for detecting aneuploidy relies on a method called quantitative fluorescent polymerase chain reaction (QF-PCR) of short tandem repeats (STRs). However, polymerase errors are frequently made in the repeat sequences, generating a high background "noise" for each STR assay. These PCR errors (stutters) make peak area measurements difficult and thus the detection and quantification of low frequency fetal DNA in maternal serum not possible (Dhallan et al., JAMA, 2004. 291(9): p. 1114-9).

In 1994, a technology called constant denaturant capillary electrophoresis (CDCE) combined with high-fidelity PCR (HiFi-PCR) was developed to allow researchers to detect and quantify low frequency somatic mutations present in heterogeneous cell populations (Khrapko et al., Nucleic Acids Res, 1994. 22(3): p. 364-9). Compared to other DNA separation methods, CDCE permits the highest resolution separation of DNA sequences differing by even a single base pair. The separation is based on differences in the melting temperature and the resulting electrophoretic mobility differences as the DNA molecules migrate through a linear polyacrylamide matrix under partially denaturing conditions (Khrapko et al., 1994). CDCE coupled with HiFi-PCR has been demonstrated to detect mutations in about 100 bp sequences with a sensitivity of at least $2\times10^{-6}$ in human cells and tissues (Li-Sucholeiki et al., Nucleic Acids Res, 2000. 28(9): p. E44). As described herein, this technology can be applied to single nucleotide polymorphisms (SNPs), natural single basepair variations present in the genome, to separate alleles. CDCE is used in the present invention to screen tandem SNPs to increase the informativeness (or heterozygosity) of each CDCE assay by increasing the number of possible alleles (or haplotypes) available. Through the use of tandem SNPs, a highly specific and sensitive assay for detecting fetal chromosomal abnormalities by simply comparing maternal serum to maternal buccal swabs has been created.

High-Fidelity PCR is an amplification method resulting in an error rate (in per basepair doubling) equal to or better than standard PCR. For example, Taq polymerase has an error rate of about $10^{-4}$ per basepair doubling. As an example, *Pyrococcus furiosus* (Pfu) is a high-fidelity polymerase. The published error rate for Pfu is $1.3\times10^{6}$ per basepair doubling (Cline et al, Nucleic Acids Res. 1996 Sep. 15; 24(18): 3546-3551).

Methods for improving PCR fidelity include, among others: A) using a high-fidelity polymerase enzyme; and B) the addition of chemical reagents (e.g., betaine) that can lower temperatures required during the PCR process. The prolonged heating of DNA and nucleotides during PCR can lead to damaged products, such as deaminated cytosines (uracils) and thus lead to misincorporation errors and miscopying errors during PCR (Andre, Kim, Khrapko, Thilly. Genome Res. 1997 7: 843-852. Zheng, Khrapko, Coller, Thilly, Copeland. Mutat Res. 2006 Jul. 25; 599(1-2):11-20). Examples of high-fidelity enzymes include Pfu and its derivations, or other enzymes with similar proofreading 3'→5' exonucleases.

In certain embodiments of the invention, amplification, e.g., HiFi-PCR, is performed with primers being in molar excess (e.g., $10^{12}$ copies/μl of primer vs $10^{6}$ or less of the template) so that it is more likely that primers will anneal with template DNA than with each other (see, e.g., Li-Sucholeiki X C, Thilly W G. Nucleic Acids Res. 2000 May 1; 28(9):E44; Thompson J R, Marcelino L, Polz M. Nucleic Acids Res. 2002 May 1; 30(9): 2083-2088.). This can significantly reduce the creation of heteroduplexes.

A "single nucleotide polymorphism (SNP)" is a single basepair variation in a nucleic acid sequence. A "tandem SNP" is a pair of SNPs that are located in a nucleic acid sequence, e.g. on a chromosome, in a manner that allows for the detection of both of the SNPs. The distance between SNPs generally is about 250 basepairs or fewer, e.g., about 200 basepairs or fewer, e.g., about 150 basepairs or fewer, e.g., about 100 basepairs or fewer, e.g., about 50 basepairs or fewer. The tandem SNPs can be detected by a variety of means that are capable of detecting the tandem SNPs. In one embodiment of the invention, constant denaturant capillary electrophoresis (CDCE) can be combined with high-fidelity PCR (HiFi-PCR) to detect the tandem SNP. In another embodiment, hybridization on a microarray is used. In another embodiment, high-fidelity PCR is used and another method capable of detecting SNPs present at low frequencies is used (e.g., denaturing HPLC, denaturing capillary electrophoresis, cycling temperature capillary electrophoresis, allele-specific PCRs, quantitative real time PCR approaches such as TaqMan® PCR system, polony sequencing approaches, microarray approaches, and mass spectrometry). In another embodiment, high-throughput sequencing approaches, e.g., at a single molecule level, are used.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA which can be single-stranded or double-stranded, optionally containing synthetic, non-natural or altered nucleotide bases capable of incorporation into DNA or RNA polymers. The terms "nucleic acid," "nucleic acid molecule," or "polynucleotide" are used interchangeably.

Certain embodiments of the invention encompass isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm. Non-limiting examples of such mathematical algorithms are the algorithm of Myers and Miller (Myers and Miller, CABIOS, 4, 11 (1988)); the local homology algorithm of Smith ct al. (Smith et al., Adv. Appl. Math., 2, 482 (1981)); the homology alignment algorithm of Needleman and Wunsch (Needleman and Wunsch, JMB, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993)).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (Higgins et al., CABIOS, 5, 151 (1989)); Corpet et al. (Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)). The ALIGN program is based on the algorithm of Myers and Miller, supra. The BLAST programs of Altschul et al. (Altschul et al., JMB, 215, 403 (1990)) are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity to the promoter sequences disclosed herein may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, 79%/o, 80%, 81%, 82%, 83%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, 80%, 90%, or even at least 95%.

Another indication that nucleotide sequences are substantially identical is if two molecules hybridize to each other under stringent conditions. Generally, stringent conditions are selected to be about 5' C lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even 95%, 96%, 97%, 98% or 99%, sequence identity to the reference sequence over a specified comparison window. In certain embodiments, optimal alignment is conducted using the homology alignment algorithm of Needleman and Wunsch (Needleman and Wunsch, JMB, 48, 443 (1970)). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, certain embodiments of the invention provide nucleic acid molecules that are substantially identical to the nucleic acid molecules described herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point (Tm) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m$ 81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10. C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), the SSC concentration is increased so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. For short nucleotide sequences (e.g., about 10 to 50 nucleotides), stringent conditions typically involve salt concentrations of less than about 1.5 M, less than about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins—that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

In addition to the chemical optimization of stringency conditions, analytical models and algorithms can be applied to hybridization data-sets (e.g. microarray data) to improve stringency.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The invention will now be illustrated by the following non-limiting Examples.

Example 1 Tandem SNPs for Chromosome 21

96 allelic markers on chromosome 21 are selected by examining tandem SNPs. These tandem SNPs will cover both q and p arms of the chromosome. Using heterozygosity data available through dbSNP, DCC Genotype Database and through the HapMap Project, SNPs that appear to be promising for high heterozygosity (≥25%) are selected. Because all four possibilities may not exist in nature due to haplotype blocks in regions of low recombination, those that suggest less than three haplotypes are screened out. FIG. 1 depicts an example of tandem SNPs (SNP 1=rs2839416, average estimated heterozygosity 0.444 and SNP2=rs2839417, average estimated heterozygosity 0.414).

Target sequences covering tandem SNPs are designed using Vector NTI and WinMelt software. As an example, the melting map of a CDCE target covering two tandem SNPs (dbSNP rs2839416 and rs2839417) on chromosome 21 was calculated using WinMelt according to the algorithm of Lerman and Silverstein (Lerman et al., Methods Enzymol, 1987. 155: p. 482-501) and is depicted in FIG. 2.

Figure 2:
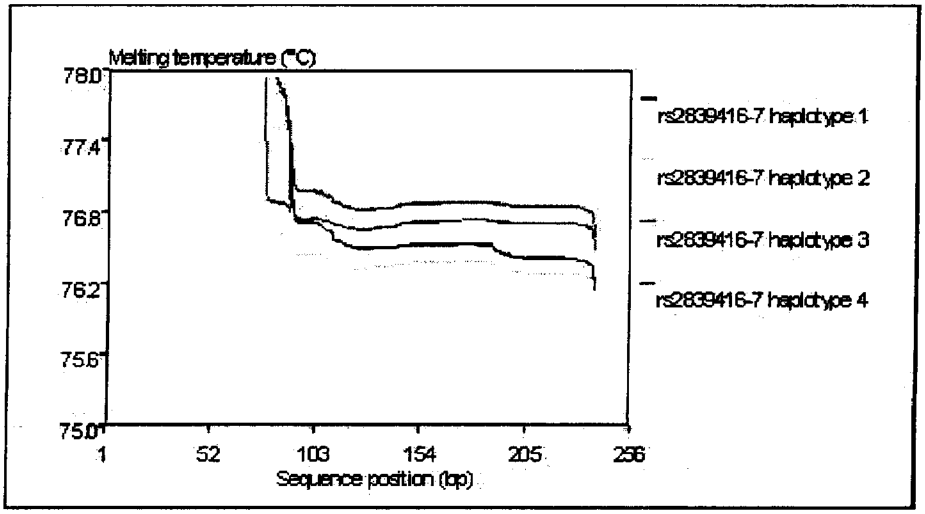
FIG. 2 depicts a DNA melting map of a constant denaturant capillary electrophoresis target sequence covering a tandem SNP.

FIG. 2 depicts a DNA melting map of a CDCE target sequence covering tandem SNPs. All four haplotypes can be theoretically separated according to DNA melting temperature. The black line indicates haplotype 1 (G,A). The yellow line indicates haplotype 2 (T,A). The red line indicates haplotype 3 (G,G). The green line indicates haplotype 4 (T,G).

HiFi PCR optimization for each target sequence is performed using Pfu polymerase. One of primers flanking the target sequence is ~20 bases in length and labeled 5' with a fluorescein molecule. The other primer is about 74 bases including a ~20-base target specific sequence and the 54-base clamp sequence. A standard HiFi PCR condition is applied to all target sequences, varying only annealing temperatures. These PCR amplicons are subjected to CDCE electrophoretic separation. The resulting electropherogram are analyzed for yield and purity of the PCR products. The purity is evaluated by comparing the peak area of the desired products to that of the byproducts and nonspecific amplification. Target sequences that can be amplified with a high PCR efficiency (≥45% per cycle) and low levels of byproducts and nonspecific amplification (≥0.1% of the desired products) are immediately be subjected to CDCE optimization. For those target sequences that do not have acceptable PCR products in the first stage, increasing amounts of $Mg^{-2}$ concentrations (up to about 7 mM) in combination with different annealing temperatures are tested. For the remaining target sequences that still do not work, primer positions are changed and the entire optimization process is repeated.

For CDCE optimization, the relevant haplotypes are created for the targets. The optimal separation condition for each haplotype should provide the greatest resolution among the observed peaks. Initial optimization is done around the theoretical melting temperature ($T_m$) in a 2° C. temperature range in increments of 0.2° C. which covers ($T_m$−1° C.±a predetermined offset) to ($T_m$+° C.±a predetermined offset).

Electropherogram and peak measurements are transferred to a spreadsheet for analysis. To ensure the quality of the data, minimum and maximum peak heights are used. Individual markers are failed if electrophoretic spikes occur. Peak areas are used to calculate allele ratios. A check for allelic preferential amplification is performed on all 96 tandem SNPs.

Results

In the fall of 2005, the International HapMap Project publicly released genotypes and frequencies from 270 people of four ethnic populations. Chromosome 21 haplotype data from approximately 40,000 SNPs genotyped across four populations, including U.S. residents with northern and western European ancestry, residents of Ibadan, Nigeria, of Tokyo, Japan, and of Beijing, China, were downloaded (2005-10-24: HapMap Public Release #19) and converted to the +orientation. Tandem SNP candidates fell within 100 basepairs from each other and at least three haplotypes existed in all four ethnic populations. CDCE target sequences and primers are designed for the tandem SNPs identified through the HapMap Project. The neighboring sequences for each of the tandem SNPs are imported into a software program, e.g., Sequencher (Gene Codes, Ann Arbor, Mich.) and/or Vector NTI (Invitrogen, Carlsbad, Calif.) for sequence alignment and primer design, and into Winmelt (Medprobe, Oslo, Norway) or Poland software (available on the world wide web at biophys.uniduesseldorf.de/local/POLAND/poland.html) where the algorithm for computing DNA melting temperatures given the Gotoh-Tagashira values for the enthalpy of melting DNA sequences are used to calculate melting temperatures of target sequences. CDCE candidates generally have a high melting region adjacent to a low melting region, lie in a low melting region, melting temperatures of the low melting region fall below 80° C., and no "valleys" occur between the high melting region and the low melting region.

All of the 40,000 genotypes on chromosome 21 have been analyzed for tandem SNP/CDCE marker suitability. 118 tandem SNPs/CDCE targets meeting our requirements have been identified (see Table 1 for the first 42 identified and Table 2 for all 118).

Primer sequences for these 118 tandem SNP/CDCE targets have been designed. These will be optimized as described herein using HiFi PCR and CDCE. These optimizations are described herein and include the creation of relevant haplotypes for all targets, a check for allelic preferential amplification during HiFi PCR, and obtaining the greatest resolution among peaks during CDCE. Haplotypes may be separated as homoduplex peaks. However, if certain targets cannot be separated out as homoduplexes, maternal DNA can be separated from fetal DNA as heteroduplexes.

TABLE 1

| Tandem SNP #/Observed haplotypes | dbSNP Name | | Chromosome | Chromosome Position | dp dif |
|---|---|---|---|---|---|
| 1 | rs10482852 | A/C | Chr21 | 14613855 | 86 |
| CC/CT/AC | rs2822567 | C/T | Chr21 | 14613941 | |
| 2 | rs2822654 | A/C | Chr21 | 14687773 | 13 |
| AA/AG/CG/CA | rs1882882 | A/G | Chr21 | 14687786 | |
| 3 | rs2822785 | A/G | Chr21 | 14876399 | 65 |
| AG/GG/AA/GA | rs2822786 | A/G | Chr21 | 14876464 | |
| 4 | re2822786 | A/G | Chr21 | 14876464 | 67 |
| GC/AC/GT | rs2822787 | C/T | Chr21 | 14876531 | |
| 5 | rs2822816 | A/G | Chr21 | 14948471 | 97 |
| AA/GT/GA | rs2822817 | A/T | Chr21 | 14948566 | |
| 6 | rs2822878 | C/T | Chr21 | 15033311 | 90 |
| CA/CG/TG | rs2822879 | A/G | Chr21 | 15033401 | |
| 7 | rs2223163 | A/G | Chr21 | 15149849 | 72 |
| AT/GT/AC | rs2822963 | C/T | Chr21 | 15149921 | |
| 8 | rs1297213 | A/G | Chr21 | 15253641 | 83 |
| GG/AG/GT/AT | rs1297214 | G/T | Chr21 | 15253724 | |
| 9 | rs2142450 | C/T | Chr21 | 15257273 | 67 |
| CT/CC/TT | rs10482863 | C/T | Chr21 | 15257340 | |
| 10 | rs10482863 | C/T | Chr21 | 15257340 | 46 |
| TC/CC/TT | rs1041403 | C/T | Chr21 | 15257366 | |
| 11 | rs2823333 | C/T | Chr21 | 15825896 | 89 |
| TA/CA/TG | rs2823334 | A/G | Chr21 | 15825985 | |
| 12 | rs2823335 | A/G | Chr21 | 15826379 | 76 |
| GG/AC/GC | rs992557 | C/G | Chr21 | 15826457 | |
| 13 | rs2823348 | A/G | Chr21 | 15833575 | 26 |
| AAA/GG/AG | rs2823349 | A/G | Chr21 | 15833601 | |
| 14 | rs2823502 | A/C | Chr21 | 16124651 | 32 |
| AT/AC/CT/CC | rs2823503 | C/T | Chr21 | 16124683 | |
| 15 | rs960391 | C/T | Chr21 | 17034864 | 29 |
| CC/CA/TC/TA | rs13049140 | A/C | Chr21 | 17034893 | |
| 16 | rs2824076 | C/T | Chr21 | 17134418 | 30 |
| CA/TA/TG | rs10482886 | A/G | Chr21 | 17134448 | |
| 17 | rs1999286 | C/T | Chr21 | 17696177 | 92 |
| CT/CC/TC | rs208897 | C/T | Chr21 | 17696269 | |
| 18 | rs2824310 | A/G | Chr21 | 17744045 | 99 |
| GG/GA/AA/AG | rs6517774 | A/G | Chr21 | 17744144 | |
| 19 | rs728015 | A/G | Chr21 | 17968624 | 33 |
| GG/AA/AG/GA | rs728014 | A/G | Chr21 | 17968657 | |
| 20 | rs1047976 | C/G | Chr21 | 18091026 | 63 |
| GG/CG/CC/GC | rs2824495 | C/G | Chr21 | 18091089 | |
| 21 | rs157058 | A/G | Chr21 | 18355312 | 53 |
| GT/GC/AT/AC | rs150141 | C/T | Chr21 | 18355365 | |
| 22 | rs2824733 | A/G | Chr21 | 18610953 | 79 |
| GG/GT/AG/AT | rs2824734 | G/T | Chr21 | 18611032 | |
| 23 | rs963638 | A/G | Chr21 | 19009158 | 56 |
| AA/GT/GA/AT | rs963639 | A/T | Chr21 | 19009214 | |
| 24 | rs2187166 | A/T | Chr21 | 19081111 | 99 |
| AC/TA/TC/AA | rs2156203 | A/C | Chr21 | 19081210 | |
| 25 | rs2825470 | C/T | Chr21 | 19567109 | 60 |
| CT/TC/CC/TT | rs2825471 | C/T | Chr21 | 19567169 | |
| 26 | rs2407561 | G/T | Chr21 | 20272611 | 28 |
| TT/GC/GT | rs2825926 | C/T | Chr21 | 20272639 | |
| 27 | rs377685 | A/G | Chr21 | 20272988 | 33 |
| GT/AT/GC/AC | rs420778 | C/T | Chr21 | 20273021 | |
| 28 | rs2826058 | A/C | Chr21 | 20464969 | 92 |
| AG/CT/CG | rs2826059 | G/T | Chr21 | 20465061 | |
| 29 | rs2826072 | C/T | Chr21 | 20487958 | 95 |
| CT/CC/TT | rs2826073 | C/T | Chr21 | 20488053 | |
| 30 | rs2032203 | C/T | Chr21 | 20598845 | 98 |
| CC/TC/TT | rs2826152 | C/T | Chr21 | 20598943 | |
| 31 | rs1735808 | C/T | Chr21 | 20766284 | 45 |
| CA/TA/CG/TG | rs1766400 | A/G | Chr21 | 20766329 | |
| 32 | rs2014509 | C/T | Chr21 | 21113061 | 79 |
| TG/CA/CG/GA | rs2014519 | A/G | Chr21 | 21113160 | |
| 33 | rs2155798 | A/G | Chr21 | 21471022 | 75 |
| GA/AA/GG | rs2155799 | A/G | Chr21 | 21471097 | |
| 34 | rs1475881 | C/G | Chr21 | 21748820 | 96 |
| GA/GG/CA | rs7275487 | A/G | Chr21 | 21748916 | |
| 35 | rs2522558 | C/G | Chr21 | 21916691 | 23 |
| CG/GG/GC/CC | rs12627388 | C/G | Chr21 | 21916714 | |
| 36 | rs12627366 | C/G | Chr21 | 21916714 | 48 |
| GC/GT/CC/CT | rs2522559 | C/T | Chr21 | 21916762 | |
| 37 | rs1735934 | A/G | Chr21 | 21995555 | 78 |
| AC/GC/GT | rs2826958 | C/T | Chr21 | 21995633 | |
| 38 | rs994676 | A/G | Chr21 | 22043945 | 34 |
| AC/GT/AT/GC | rs2826982 | C/T | Chr21 | 22043979 | |

TABLE 1-continued

| Tandem SNP #/Observed haplotypes | dbSNP Name | | Chromosome | Chromosome Position | dp dif |
|---|---|---|---|---|---|
| 39 | rs1735976 | A/G | Chr21 | 22054777 | 31 |
| AA/GC/AC | rs2827016 | A/C | Chr21 | 22054808 | |
| 40 | rs1013069 | A/G | Chr21 | 22545627 | 67 |
| AA/GA/AG/GG | rs2827307 | A/G | Chr21 | 22545694 | |
| 41 | rs244260 | A/G | Chr21 | 23311737 | 88 |
| AT/GT/AC/GC | rs244261 | C/T | Chr21 | 23311825 | |
| 42 | rs2051265 | A/C | Chr21 | 23334109 | 47 |
| CG/CC/AG/AC | rs198061 | C/G | Chr21 | 23334156 | |

Example 2 Determining Heterozygosity of the Tandem SNPs

As a complement to Example 1, genomic DNA samples from 300 anonymous subjects have been obtained from healthy young adults who are less than 35 years old. The samples are anonymous as the only data obtained were the geographic location of the Red Cross blood donor center, donor gender, and whether or not the donor was 35 and under. These samples were spot-checked to look for the haplotypes seen in the HapMap project.

Example 3 Detecting Fetal DNA from Maternal Serum

A cohort of patients who have been confirmed to have trisomy 21 by traditional karyotype analysis are examined. Tandem SNPs are used to demonstrate detection of trisomy in patients. DNA from 20 patients who have been characterized by traditional karyotype analysis to have trisomy 21 are analyzed with the tandem SNP panel.

Biological samples, including a buccal (cheek) swab and a blood sample are collected from a cohort of pregnant women. Maternal buccal swab samples are compared to maternal serum to demonstrate that a third (paternal) peak is observed in several of the tandem SNP assays. Approximately 20 maternal buccal swab to maternal serum comparisons are made. To control for experimental artifacts, genomic DNA samples from maternal buccal swabs are utilized for each target sequence. The buccal samples are subjected to the process in parallel with the maternal blood sample. Any artifacts generated by the CDCE/HiFi-PCR procedure (including nonspecific PCR amplification and polymerase-induced mutations) are revealed as background peaks in the buccal swab samples.

Example 4 Detecting Fetal Chromosomal Abnormalities

Figure 3:
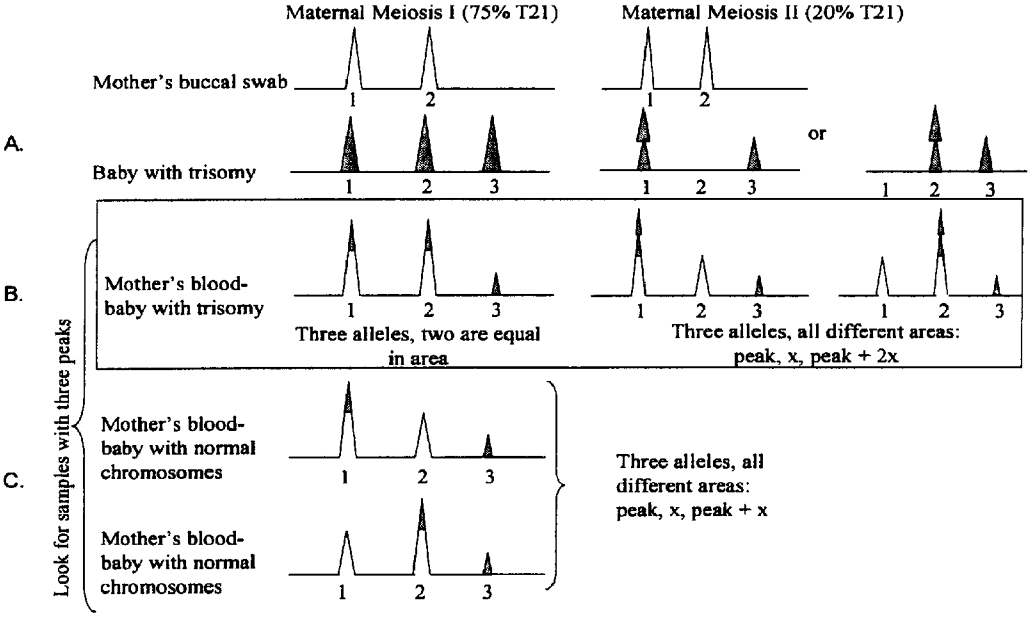
FIG. 3 depicts an example of a constant denaturant capillary electrophoresis electropherogram output. Each peak in these graphs represents the number of molecules of each allele for a marker detected in a sample.

A blinded study is performed where the goal is to detect 20 known trisomy 21 fetuses by assaying maternal serum from 40 patients (previously determined by amniocentesis or CVS) (see FIG. 3).

FIG. 3 depicts an example of a CDCE electropherogram output with the peaks at full scale. FIG. 3A depicts a sample from maternal buccal swab. Markers exhibiting two alleles are pursued. A baby with trisomy is expected to show either three alleles, evident by three peaks in a 1:1:1 ratio or two alleles in a 2:1 ratio. FIG. 3B depicts a sample from maternal serum. Markers exhibiting three alleles are informative. Maternal serum from a woman carrying a baby with trisomy is expected to exhibit three alleles, evident by two equal peaks with a third smaller peak if the trisomy occurred during meiosis I (75% of T21 cases) or three alleles with different areas if the trisomy occurred during meiosis II (20% of T21 cases) where areas are: peak, x, and peak+2x. FIG. 3C depicts analysis of a sample from maternal serum. Markers exhibiting three alleles are informative. Maternal serum from a woman with a normal baby with three alleles has three different areas where areas are: peak, x, and peak+x.

Interretation of Results

For the case of the minimum heterozygosity, where both SNP1 and SNP2 are heterozygous at their respective loci at a rate of 25%, if 96 tandem SNPs are assayed, an average of 43 markers (44.5%) are expected to be heterozygous (two haplotypes) in the mother. The mother's expected heterozygosity is calculated using the following formula:

$$H=1-\Sigma p_i^2$$

for i=1 to k alleles where $p_i$=estimated allele frequency.

The allele frequencies at each SNP loci are expected to be 85% and 15% for the majority and minority alleles, respectively, assuming Hardy-Weinberg equilibrium. The desired third haplotype is expected to be present at an average of 6.4 markers (15%) of per maternal-fetal sample tested. Because most loci have a heterozygosity value greater than 25%, for every maternal-fetal sample tested using the panel of 96 tandem SNP assays, greater than about 6.4 markers are most informative. Thus, while a panel of 96 tandem SNPs may be used, 6 or 7 of those tandem SNPs may be informative for any one specific maternal-fetal sample tested, and a 'positive' result from any one of those tandem SNPs is informative.

Finally, in order to diagnose a trisomy, a "positive" tandem SNPs should be identified on both the p and the q arm of chromosome 21. Because of the comparative nature of the basic approach, the tandem SNP assay is predicted to have a detection rate of 95% (those that occur during maternal meiosis) for trisomy 21. If paternal samples are available, non-disjunctions that occur during paternal meiosis can also be detected. Thus, detection rates would be higher (about ~99%) with a 0% false positive rate.

Example 5 Tandem SNPs and Primers

Table 2 provides exemplary tandem SNPs of the invention and primers that can be used in the methods of the invention to detect the tandem SNPs. Certain embodiments of the present invention provide primers that can be used to amplify at least one of the SNPs. Certain embodiments of the present invention provide nucleic acid sequences that comprise at least one of the SNPs, e.g., at least one of the tandem SNPs.

TABLE 2

```
1) Whole sequence ::: rs432114-rs305433 CC/CT/GC/GT

AACAAATCTTCATCTTGGAATAGCCTGTGAGAATGCCTAATCATCTACGAATgTTACTTT
GGCACOATCTACTOGACkgA7TAAATAACAACCAACTCACTGIGGATTAGACCTACTTCT
ATTTCAG (SEQ ID NO: 1)

OLIGO start len tm gc % any C:\Documents and Settings\Ramakrishna
Mulpuri\Desktop\first 10 primers -redesigned\primer3_www_results_help.cgi -
PRIMER_THREE 3' seq (SEQ ID NOs: 2, 3)
LEFT PRIMER      20  20  55.08  45.00  3.00 2.00 ATAGCCTGTGAGAATGCCTA
RIGHT PRIMER    107  20  55.30  45.00  5.00 0.00 ATCCACAGTGAGTTGGTTGT
SEQUENCE SIZE: 127
INCLUDED REGION SIZE: 127

PRODUCT SIZE: 88, PAIR ANY COMPL: 5.00, PAIR 3' COMPL: 1.00

   1 AACAAATCTTCATCTTGGAATAGCCTGTGAGAATGCCTAATCATCTACGAATgTTACTTT
            >>>>>>>>>>>>>>>>>>>>

  61 GGCACCATCTACTGGACAgATTAAATAACAACCAACTCACTGTGGATTAGACCTACTTCT
               <<<<<<<<<<<<<<<<<<<<

 121 ATTTCAG

2) Whole sequence ::: rs7277033-rs2110153 CC/CT/TC/TT
PCR did not work

TTCCTGGAAAACAAAAGTATTTCTTTCATAGCCCAGCTAGCAtGATAAATCAGCgAGTCA
GAATTCTAGCTTTGTTGTAAGGTT (SEQ ID NO: 4)

OLIGO start len tm gc % any C:\Documents and Settings\Ramakrishna
Mulpuri\Desktop\first 10 primers -redesigned\primer3_www_results_help.cgi -
PRIMER_THREE 3' seq (SEQ ID NOs: 5, 6)
LEFT PRIMER       2  20  51.63  30 00  5.00 3.00 TCCTGGAAAACAAAAGTATT
RIGHT PRIMER     84  21  51.36  33.33  4.00 0.00 AACCTTACAACAAAGCTAGAA
SEQUENCE SIZE: 84
INCLUDEO REGION SIZE: 84

PRODUCT SIZE: 83, PAIR ANY COMPL: 3.00, PAIR 3' COMPL: 2.00

   1 TTCCTGGAAAACAAAAGTATTTCTTTCATAGCCCAGCTAGCAtGATAAATCAGCgAGTCA
     >>>>>>>>>>>>>>>>>>>>

  61 GAATTCTAGCTTTGTTGTAAGGTT
     <<<<<<<<<<<<<<<<<<<<
```

TABLE 2-continued

```
3) Whole sequence ::: rs2822654-rs1882882 AA/AG/CA/CG

CACTAAGCCTTGGGGATCCAGCTGCTTaAGGACTAAGACCgTATCTAGCTCCTTTTAGTA
TTTCCACAGCA (SEQ ID NO: 7)

OLIGO start len tm gc % any c:\Documents and Settings\Ramakrishna
Mulpuri\Desktop\first 10 primers -redesigned\primer3_www_results_help.cgi -
PRIMER_THREE 3' seq (SEQ ID NOs: 8, 9)
LEFT PRIMER       2  20  60.46  55.00  6.00 2.00 ACTAAGCCTTGGGGATCCAG
RIGHT PRIMER     71  21  54.78  38.10  3.00 0.00 TGCTGTGGAAATACTAAAAGG
SEQUENCE SIZE: 71
INCLUDED REGION SIZE: 71

PRODUCT SIZE: 70, PAIR ANY COMPL: 4.00, PAIR 3' COMPL: 0.00

   1 CACTAAGCCTTGGGGATCCAGCTGCTTaAGGACTAAGACCgTATCTAGCTCCTTTTAGTA
     >>>>>>>>>>>>>>>>>>>>        <<<<<<<<<<

  61 TTTCCACAGCA
   <<<<<<<<<<

4) Whole sequence ::: rs366657-rs376635 AA/AG/GA/GG

TCCTCCAGAGGTAATCCTGTGATCAGCACTAACaCCACATACCAGCCCTTTCATCAGCTT
CTTGGAGAAGCATCTTTACTTCCCgCCAAGCAGTGACCTagataccatctcacaccagtt
agaatcaggatcattaaaaagtcaagaaaaaacag (SEQ ID NO: 10)

OLIGO start len tm gc % any c:\Documents and Settings\Ramakrishna
Mulpuri\Desktop\first 10 primers -redesigned\primer3_www_results_help.cgi -
PRIMER_THREE 3' seq (SEQ ID NOs: 11, 12)
LEFT PRIMER       3  20  55.20  50.00  5.00 3.00 CTCCAGAGGTAATCCTGTGA
RIGHT PRIMER    117  21  55.10  47.62  5.00 2.00 tggtgtgagatggtatctAGG
SEQUENCE SIZE: 155
INCLUDED REGION SLZE: 155

PRODUCT SIZE: 115, PAIR ANY COMPL: 3.00, PAIR 3' COMPL: 2.00

   1 TCCTCCAGAGGTAATCCTGTGATCAGCACTAACaCCACATACCAGCCCTTTCATCAGCTT
     >>>>>>>>>>>>>>>>>>>>

  61 CTTGGAGAAGCATCTTTACTTCCCgCCAAGCAGTGACCTagataccatctcacaccagtt
                  <<<<<<<<<<<<<<<<<<<<

 121 agaatcaggatcattaaaaagtcaagaaaaaacag

5) Whole sequence ::: rs2822731-rs2822732 AA/AG/GA/GG

TCCAAGTATAATCCATGAATCTTGTTTAAATATAGATCAAaTAAACCACTATACCAAAAA
CATCAAAAGACAACTGGGTAAATTTTTTAAATGACTAGCTATTTGATGTTAAgGAAGTAA
TGTTACTCTCTTATATACAATTTGAA (SEQ ID NO: 13)

OLIGO start len tm gc % any c:\Documents and Settings\Ramakrishna
Mulpuri\Desktop\first 10 primers -redesigned\primer3_www_results_help.cgi -
PRIMER_THREE 3' seq (SEQ ID NOs: 14, 15)
LEFT PRIMER       6  22  50.35  27.27  6.00 3.00 GTATAATCCATGAATCTTGTTT
RIGHT PRIMER    146  22  45.69  22.73  6.00 1.00 TTCAAATTGTATATAAGAGAGT
SEQUENCE SIZE: 146
INCLUDED REGION size: 146

PRODUCT SIZE: 141, PAIR ANY COMPL: 4.00, PAIR 3' COMPL: 2.00

   1 TCCAAGTATAATCCATGAATCTTGTTTAAATATAGATCAAaTAAACCACTATACCAAAAA
       >>>>>>>>>>>>>>>>>>>>

  61 CATCAAAAGACAACTGGGTAAATTTTTTAAATGACTAGCTATTTGATGTTAAgGAAGTAA

 121 TGTTACTCTCTTATATACAATTTGAA
     <<<<<<<<<<<<<<<<<<<<

6) Whole sequence ::: rS6516899-RS455221 CC/CT/TC/TT

ATGGAACCGAAACTTCAAGTAGTTTCATAcGTATCACATTGACAGTTTTCTCTAAGTTTT
CtGGTCTTATGACTCGTTGTTTCATTATTAAAACTGTGCCAGTGTATGCATAGGGCTTAG
(SEQ ID NO: 16)

OLIGO start len tm gc % any c:\Documents and Settings\Ramakrishna
Mulpuri\Desktop\first 10 primers -redesigned\primer3_www_results_help.cgi -
PRIMER_THREE 3' seq (SEQ ID NOs: 17, 18)
LEFT PRIMER       1  16  53.87  38.89  4.00 3.00 ATGGAACCGAAACTTCAA
RIGHT PRIMER     91  22  52.84  27.27  5.00 1.00 TTAATAATGAAACAACGAGTCA
```

TABLE 2-continued

```
SEQUENCE SIZE: 132
INCLUDED REGION SIZE: 132

PRODUCT SIZE: 91, PAIR ANY COMPL: 4.00, PAIR 3' COMPL: 0.00

   1 ATGGAACCGAAACTTCAAGTAGTTTCATAcGTATCACATTGACAGTTTTCTCTAAGTTTT
    >>>>>>>>>>>>>>>>>>>>

  61 CtGGTCTTATGACTCGTTGTTTCATTATTAAAACTGTGCCAGTGTATGCATAGGGCTTAG
        <<<<<<<<<<<<<<<<<<<<

 121 AATTTTTTAAT

7) Whole sequence ::: rs7275381-rs12627144 GA/GG/TA/TG

acaggatccttcctgaagacaccaccttggggagggtgaagGataaagaatttgatcaga
aatcaagggtggtgagatacatgttaaggatgaataaactggccttttaggattcttgct
aaaAttagacaatgcagaggcaaccacagagtccaag (SEQ ID NO: 19)

OLIGO start len tm gc % any c:\Documents and Settings\Ramakrishna
Mulpuri\Desktop\first 10 primers -redesigned\primer3_www_results_help.cgi -
PRIMER_THREE 3' seq (SEQ ID NOs: 20, 21)
LEFT PRIMER      10  19  55.53  47.37  4.00 0.00 ttctgaagacaccacctt
RIGHT PRIMER    157  18  54.94  55.56  3.00 2.00 cttggactctgtggttgc
SEQUENCE SIZE: 157
INCLUDED REGION SIZE: 157

PRODUCT SIZE 148, PAIR ANY COMPL: 5.00, PAIR 3' COMPL: 1.00

   1 acaggatccttcctgaagacaccaccttggggagggtgaagGataaagaatttgatcaga
         >>>>>>>>>>>>>>>>>>>>

  61 aatcaagggtggtgagatacatgttaaggatgaataaactggccttttaggattcttgct

 121 aaaAttegacaatgcagaggcaaccacagagtccaag
              <<<<<<<<<<<<<<<<<<<<

8) Whole sequence ::: rs1999288-rs208897 CC/CT/TC

AATTTCCATTAAATCTTGTTCGTTGCTTTACTGAGGCACTGAAGTTACCAATGTTcCACT
GGTTGACCTGCGGGGCTATCTCTAGGTTATGTTACTCCAGAAAATGAATTGTGTATAAAA
GAGGCCTTGGAGGAAGGCGTTTTATTCaCATCAGTTGTTTTGCACATTGCTTA (SEQ ID NO: 22)

OLIGO start len tm gc % any c:\Documents and Settings\Ramakrishna
Mulpuri\Desktop\first 10 primers -redesigned\primer3_www_results_help.cgi -
PRIMER_THREE 3' seq (SEQ ID NOs: 23, 24)
LEFT PRIMER      30  20  54.40  50.00  4.00 2.00 ACTGAGGCACTGAAGTTACC
RIGHT PRIMER    173  20  54.96  35.00  4.00 0.00 TAAGCAATGTGCAAAACAAC
SEQUENCE SIZE: 173
INCLUDED REGION SIZE: 173

PRODUCT SIZE 144, PAIR ANY COMPL: 4.00, PAIR 3' COMPL: 0.00

   1 AATTTCCATTAAATCTTGTTCGTTGCTTTACTGAGGCACTGAAGTTACCAATGTTcCACT
                >>>>>>>>>>>>>>>>>>>>

  61 GGTTGACCTGCGGGGCTATCTCTAGGTTATGTTACTCCAGAAAATGAATTGTGTATAAAA

 121 GAGGCCTTGGAGGAAGGCGTTTTATTCaCATCAGTTGTTTTGCACATTGCTTA
               <<<<<<<<<<<<<<<<<<<<

9) Whole sequence ::: rs1475681-rs7275487 CA/CG/GA/GG
POR did not work

TCGGTTTCAGCAGGAAAGTTATTTTTAATAACTTCCCTGTATTTcTTGGTTTCAGTTATTAATTAACTCA
TTAATGCTAAACTTTGTGATCCTAGGTTAAAAAACATATTCAAGATAGCTTCAGAATGTTTGGTATACA
AgTAGGTCTGGCTAAATATAAGTGTTAGCTTTCTCAAGCATCTAAATGCTGG (SEQ ID NO: 25)

OLIGO start len tm gc % any http://frodo.wi.mit.edu/cgi-
bin/primer3/primer3_www_results_help.cgi - PRIMER_THREE 3' seq
(SEQ ID NOs: 26, 27)
LEFT PRIMER      10  20  48.49  25.00  5.00 3.00 GCAGGAAAGTTATTTTTAAT
RIGHT PRIMER    179  21  54.70  38.10  4.00 1.00 TGCTTGAGAAAGCTAACACTT
SEQUENCE SIZE: 191
INCLUDED REGION SIZE: 191
```

TABLE 2-continued

PRODUCT SIZE: 170, PAIR ANY COMPL: 5.00, PAIR 3' COMPL: 2.00

```
  1 TCGGTTTCAGCAGGAAAGTTATTTTTAATAACTTCCCTGTATTTcTTGGTTTCAGTTATT
       >>>>>>>>>>>>>>>>>>>>

 61 AATTAACTCATTAATGCTAAACTTTGTGATCCTAGGTTAAAAAACATATTCAAGATAGCT

121 TCAGAATGTTTGGTATACAAgTAGGTCTGGCTAAATATAAGTGTTAGCTTTCTCAAGCAT
                    <<<<<<<<<<<<<<<<<<

181 CTAATGCTGG
```

ALTERNATIVE:: (LESS THAN 5 bp APART)

AAGTTATTTTTAATAACTTCCCTGTATTTcTTGGTTTCAGTTATTAATTAACTCATTAAT
GCTAAACTTTGTGATCCTAGGTTAAAAAACATATTCAAGATAGCTTCAGAATGTTTGGTA
TACAAgTAGGTCTGGCTAAATATAAGTGTTAGCTTTCTCAAGCATC (SEQ ID NO: 28)

OLIGO start len tm gc % any http://frodo.wi.mit.edu/cgi-
bin/primer3/primer3_www_results_help.cgi - PRIMER_THREE 3' seq
(SEQ ID NOs: 29, 30)
LEFT PRIMER      6  20  47.68  25.00  6.00  0.00 ATTTTTAATAACTTCCCTGT
RIGHT PRIMER   140  20  49.30  40.00  4.00  0.00 CACTTATATTTAGCCAGACC
SEQUENCE SIZE: 166
INCLUDED REGION SIZE: 166

PRODUCT SIZE: 143, PAIR ANY COMPL: 4.00, PAIR 3' COMPL: 1.00

```
  1 AAGTTATTTTTAATAACTTCCCTGTATTTcTTGGTTTCAGTTATTAATTAACTCATTAAT
       >>>>>>>>>>>>>>>>>>>>

 61 GCTAAACTTTGTGATCCTAGGTTAAAAAACATATTCAAGATAGCTTCAGAATGTTTGGTA

121 TACAAgTAGGTCTGGCTAAATATAAGTGTTAGCTTTCTCAAGCATC
              <<<<<<<<<<<<<<<<<<
```

10) What sequence ::: rs1735976-rs2827016 AA/AC/GA/GC

ATTCATTGTGTAGAAAGTGCCTGACTCAGTGTTTGGAAATTGTCTGACTTTTCCTCATAT
aTAGTGTGGTTTCATGTTATTGTATATAAGAaCTGACATGAACTCTGTTTACAATAATCT
CCCAGTGCCATAAAGACCATAATAAATAATAT (SEQ ID NO: 31)

OLIGO start len tm gc % any c:\Documents and Settings\Ramakrishna
Mulpuri\Desktop\first 10 primers -redesigned\primer3_www_results_help.cgi -
PRIMER_THREE 3' seq (SEQ ID NOs: 32, 33)
LEFT PRIMER     27  20  54.11  40.00  4.00  1.00 CAGTGTTTGGAAATTGTCTG
RIGHT PRIMER   129  20  55.17  45.00  3.00  2.00 GGCACTGGGAGATTATTGTA
SEQUENCE SIZE: 152
INCLUDED REGION SIZE: 152

PRODUCT SIZE: 103, PAIR ANY COMPL: 5.00, PAIR 3' COMPL: 1.00

```
  1 ATTCATTGTGTAGAAAGTGCCTGACTCAGTGTTTGGAAATTGTCTGACTTTTCCTCATAT
                                >>>>>>>>>>>>>>>>>>>>

 61 aTAGTGTGGTTTCATGTTATTGTATATAAGAaCTGACATGAACTCTGTTTACAATAATCT
                       <<<<<<<<<

121 CCCAGTGCCATAAGACCATAATAAATAATAT
      <<<<<<<<<
```

2<sup>nd</sup> group of primers

11) Whole sequence ::: rs447349-rs2824097 CT/TC/TT (156 long)

CACTGGGTCCTGTTGTTAAGTACACATAATACCACaCAGGAGAAAATCAGGCTAATTGTA
AATGGGCAACCTACTTAATTGTTTCATTAAAAAGCATACAGATTACATTTACACTAtAGC
TAGTCTTGTTTGTTTTTTTATTTTGCAAAAGTAATTACGGCCC (SEQ ID NO: 34)

OLIGO start len tm gc % any http://frodo.wi.mit.edu/cgi-
bin/primer3/primer3_www_results_help.cgi - PRIMER_THREE 3' seq
(SEQ ID NOs: 35, 36)
LEFT PRIMER      8  20  47.79  35.00  6.00  2.00 TCCTGTTGTTAAGTACACAT
RIGHT PRIMER   163  18  53.29  44.44  8.00  2.00 GGGCCGTAATTACTTTTG
SEQUENCE SIZE: 163
INCLUDED REGION SIZE: 163

TABLE 2-continued

PRODUCT SIZE: 156, PAIR ANY COMPL: 5.00, PAIR 3' COMPL: 1.00

1 CACTGGGTCCTGTTGTTAAGTACACATAATACCACaCAGGAGAAAATCAGGCTAATTGTA
>>>>>>>>>>>>>>>>>>>>

61 AATGGGCAACCTACTTAATTGTTTCATTAAAAAGCATACAGATTACATTTACACTAtAGC

121 TAGTCTTGTTTGTTTTTTTATTTTGCAAAAGTAATTACGGCCC
<<<<<<<<<<<<<<<<<<<<

12) Whole sequence ::: rs418989-rs13047338 AC/AT/CC

CTACTCAGTAGGCACTTTGTGTCTAGAAACTTCTGTGTCAACgGTTTTCCCTCTCTCTGG
AATTCaTCAGGACAGAAGTGATTGGTGTGGTGGAAGAGGGTTGTGSTA (SEQ ID NO: 37)

OLIGO start len tm gc % any http://frodo.wi.mit.edu/cgi-bin/primer3/primer3_www_results_help.cgi - PRIMER_THREE 3' seq
(SEQ ID NOs: 38, 39)
LEFT PRIMER 3 21 64.60 47.62 5.00 3.00 ACTCAGTAGGCACTTTGTGTC
RIGHT PRIMER 97 18 54.95 50.00 2.00 0.00 TCTTCCACCACACCAATC
SEQUENCE SIZE: 108
INCLUDED REGION SIZE: 108

PRODUCT SIZE: 95, PAIR ANY COMPL: 5.00, PAIR 3' COMPL: 2.00

1 CTACTCAGTAGGCACTTTGTGTCTAGAAACTTCTGTGTCAACgGTTTTCCCTCTCTCTGG
>>>>>>>>>>>>>>>>>>>>

61 AATTCaTCAGGACAGAAGTGATTGGTGTGGTGGAAGAGGGTTGTGSTA
<<<<<<<<<<<<<<<<<<<<

13) Whole sequence ::: rs967960-rs987961 AG/GG/GT

TGGCTTTTCAAAGGTAAAATTTACTaAGTGTATTAATATTTTACCAATTTCCAGCCAGGA
GAGTATGAATGTTGCATTATTACATTGCTTTGAAACAAAGCATTAgTCTTAATTCAGAAG
TTTAAATTCAGATGTTAACGTTGC (SEQ ID NO: 40)

OLIGO start len tm gc % any http://frodo.wi.mit.edu/cgi-bin/primer3/primer3_www_results_help.cgi - PRIMER_THREE 3' seq
(SEQ ID NOs: 41, 42)
LEFT PRIMER 1 19 53.67 31.58 6.00 2.00 TGGCTTTTCAAAGGTAAAA
RIGHT PRNER 144 21 54.59 33.33 6.00 3.00 GCAACGTTAACATCTGAATTT
SEQUENCE SIZE: 144
INCLUDED REGION SIZE: 144

PRODUCT SIZE: 144, PAIR ANY COMPL: 6.00, PAIR 3' COMPL: 3.00

1 TGGCTTTTCAAAGGTAAAATTTACTaAGTGTATTAATATTTTACCAATTTCCAGCCAGGA
>>>>>>>>>>>>>>>>>>>>

61 GAGTATGAATGTTGCATTATTACATTGCTTTGAAACAAAGCATTAgTCTTAATTCAGAAG

121 TTTAAATTCAGATGTTAACGTTGC
<<<<<<<<<<<<<<<<<<<<

14) Whole sequence ::: rs4143392-rs4143391 CA/CG/GA/GG

TAAGTATTGAAGAAAGGAGAATTTAAATTACTTCATATACctgataaaggaaaacatata
CAAGGCAAATAAACATCTTAGATCATGACATATAAAATAATAGATTATTA (SEQ ID NO: 43)

OLIGO start len tm gc % any http://frodo.wi.mit.edu/cgi-bin/primer3/primer3_www_results_help.cgi - PRIMER_THREE 3' seq
(SEQ ID NOs: 44, 45)
LEFT PRIMER 7 20 49.58 25.00 4.00 4.00 TTGAAGAAAGGAGAATTTAA
RIGHT PRIMER 98 22 45.86 22.73 6.00 3.00 ATTTTATATGTCATGATCTAAG
SEQUENCE SIZE: 110
INCLUDED REG1ON SIZE: 110

PRODUCT SIZE: 92, PAIR ANY COMPL: 4.00, PAIR 3' COMPL: 1.00

1 TAAGTATTGAAGAAAGGAGAATTTAAATTACTTCATATACctgataaaggaaaacatata
>>>>>>>>>>>>>>>>>>>>

61 CAAGGCAAATAAACATCTTAGATCATGACATATAAAATAATAGATTATTA
<<<<<<<<<<<<<<<<<<<<

TABLE 2-continued

```
15) Whole sequence ::: rs1691324-rs13050434 CG/TA/TG
(4 bp apart for right primer)

TGCAGAGATTACAGGTGTGAGCCACCGTGCCCAGCCTCATAACcGTTTCAACTACTTTTT
CACTTGACAAGCAGATGTGAAGTTAACAAAGTCACCCATATTTGAAATAAAGATAGTATA
TTCCTGGGGtAGGCAGAGGCAGTTGAGGATCATGAAATAACTATG (SEQ ID NO: 46)

OLIGO start len tm gc % any http://frodo.wi.mit.edu/cgi-
bin/primer3/primer3_www_results_help.cgi - PRIMER_THREE 3' seq
(SEQ ID NOs: 47, 48)
LEFT PRIMER       4  19  49.78  47.37  4.00  4.00 AGAGATTACAGGTGTGAGC
RIGHT PRIMER    153  19  54.61  47.37  4.00  0.00 ATGATCCTCAACTGCCTCT
SEQUENCE SIZE: 165
INCLUDED REGION SIZE: 165

PRODUCT SIZE: 150, PAIR ANY COMPL: 4.00, PAIR 3' COMPL: 2.00

   1 TGCAGAGATTACAGGTGTGAGCCACCGTGCCCAGCCTCATAACcGTTTCAACTACTTTTT
        >>>>>>>>>>>>>>>>>>>

  61 CACTTGACAAGCAGATGTGAAGTTAACAAAGTCACCCATATTTGAAATAAAGATAGTATA

 121 TTCCTGGGGtAGGCAGAGGCAGTTGAGGATCATGAAATAACTATG
                   <<<<<<<<<<<<<<<<<<<

16) Whole sequence ::: rs11909758-rs9980111 (159 bp long) AG/AT/GT

TGCAATGAAACTCAAAAGAGAAAAGTTAACAGGTGCAAaAGGTAGTTTTATTATAAAAGG
AGGGTAGGCAACAAGAATATGTTTAATTTTTCTTCCTTTTCATGAGTAAGGACAAGAGTg
TCATATATGTGaatatttttatttaattttaaGTAGAAATCTGTTTTTAAATATGGG
(SEQ ID NO: 49)

OLIGO start len tm gc % any http://frodo.wi.mit.edu/cgi-
bin/primer3/primer3_www_results_help.cgi - PRIMER_THREE 3' seq
(SEQ ID NOs: 50, 51)
LEFT PRIMER       6  20  49.91  30.00  3.00  0.00 TGAAACTCAAAAGAGAAAAG
RIGHT PRIMER    164  20  42.77  20.00  6.00  4.00 ACAGATTTCTACttaaaatt
SEQUENCE SIZE: 178
INCLUDED REGION SIZE: 178

PRODUCT SIZE: 159, PAIR ANY COMPL: 6.00, PAIR 3' COMPL: 3.00

   1 TGCAATGAAACTCAAAAGAGAAAAGTTAACAGGTGCAAaAGGTAGTTTTATTATAAAAGG
          >>>>>>>>>>>>>>>>>>>>

  61 AGGGTAGGCAACAAGAATATGTTTAATTTTTCTTCCTTTTCATGAGTAAGGACAAGAGTg

 121 TCATATATGTGaatatttttatttaattttaaGTAGAAATCTGTTTTTAAATATGG
                             <<<<<<<<<<<<<<<<<<<<

17) Whole sequence ::: rs854613-rs854614 AA/AG/TG

CCACCATTCATCAAAACTTTGATACTGGACTCAATTGTGAATTTGaCTTGAAATTTGATA
ATGCTTTTGTTTTACTgTTCTGCTCAGCAAAATAGTACATGT (SEQ ID NO: 52)

OLIGO start len tm gc % any http://frodo.wi.mit.edu/cgi-
bin/primer3/primer3_www_results_help.cgi - PRIMER_THREE 3' seq
(SEQ ID NOs: 53, 54)
LEFT PRIMER      12  20  49.40  35.00  0.00  1.00 CAAAACTTTGATACTGGACT
RIGHT PRIMER    102  19  46.05  31.58  0.00  1.00 ACATGTACTATTTTGCTGA
SEQUENCE SIZE: 102
INCLUDED REGION SIZE: 102

PRODUCT SIZE: 91, PAIR ANY COMPL: 6.00, PAIR 3' COMPL: 1.00

   1 CCACCATTCATCAAAACTTTGATACTGGACTCAATTGTGAATTTGaCTTGAAATTTGATA
                >>>>>>>>>>>>>>>>>>>>

  61 ATGCTTTTGTTTTACTgTTCTGCTCAGCAAAATAGTACATGT
                            <<<<<<<<<<<<<<<<<<<
```

3rd group - order primers from 18-25

TABLE 2-continued

18) Whole sequence ::: rs2826225-rs2826226 AA/GA/GC

GCCTGCATAAAGTGAGGATGGTGTAGTAATTGGGTATCTCCAGTTATAAACACAAaAAGC
ATGATAGAGCTGGGAcTGTGATTGCAGGAAAGCAATAGTCACTCCAAAAGGAGATCCTCA
TGATATGAATACGGAAGAAACAATATTTCCTGCTAATGTAGTAGCC (SEQ ID NO: 55)

OLIGO start len tm gc % any http://frodo.wi.mit.edu/cgi-
bin/primer3/primer3_www_results_help.cgi - PRIMER_THREE 3' seq
(SEQ ID NOs: 56, 57)
LEFT PRIMER 2 20 58.17 50.00 4.00 0.00 CCTGCATAAAGTGAGGATGG
RIGHT PRIMER 120 21 59.27 47.62 6.00 0.00 TGAGGATCTCCTTTTGGAGTG
SEQUENCE SIZE: 166
INCLUDED REGION SIZE: 166

PRODUCT SIZE: 119, PAIR ANY COMPL: 6.00, PAIR 3' COMPL: 3.00

1 GCCTGCATAAAGTGAGGATGGTGTAGTAATTGGGTATCTCCAGTTATAAACACAAaAAGC
>>>>>>>>>>>>>>>>>>>>

61 ATGATAGAGCTGGGAcTGTGATTGCAGGAAAGCAATAGTCACTCCAAAAGGAGATCCTCA
<<<<<<<<<<<<<<<<<<<<<

121 TGATATGAATACGGAAGAAACAATATTTCCTGCTAATGTAGTAGCC

19) Whole Sequence ::: rs2826842-rs232414 CA/CG/TA/TG

GCAAAGGGGTACTCTATGTAATGAAcATgacctggcagtactgacatctcctgagggact
gttagaagtgcagactcttgtatcttttctcaagtctatgaaatctagacttcattttaa
caagatgacccgatatttacatacacattaaagt (SEQ ID NO: 58)

OLIGO start len tm gc % any http://frodo.wi.mit.edu/cgi-
bin/primer3/primer3_www_results_help.cgi - PRIMER_THREE 3' seq
(SEQ ID NOs: 59, 60)
LEFT PRIMER 1 20 52.04 45.00 4.00 2.00 GCAAAGGGGTACTCTATGTA
RIGHT PRIMER 135 20 53.29 35.00 4.00 3.00 tatcgggtcatcttgttaaa
SEQUENCE SIZE: 164
INCLUDED REGION SIZE: 164

PRODUCT SIZE 135, PAIR ANY COMPL: 3.00, PAIR 3' COMPL: 2.00

1 GCAAAGGGGTACTCTATGTAATGAAcATgacctggcagtactgacatctcctgagggact
>>>>>>>>>>>>>>>>>>>>

61 gttagaagtgcagactcttgtatcttttctcaagtctatgaaatctagacttcattttaa
<<<<<

121 caagatgacccgatatttacatacacattaaagt
<<<<<<<<<<<<<<<

20) Whole sequence ::: rs1960969-rs1960970 AA/AG/TA/TG

GTATCTAACAAAGCTCTGTCCAAAATTTTGAATTTCTCGTTAAAaGCATCATGATTATAG
AACAGAGGTTACAATCAATTATTCAGTCACACAATCACTCTCATCAGTCATTAAGGTGCg
TACCTGGTGTTCCAGTTATTCAGTGTGGTATAACAAACTACCTGGAACTTAATG (SEQ ID NO: 61)

OLIGO start len tm gc % any http://frodo.wi.mit.edu/cgi-
bin/primer3/primer3_www_results_help.cgi - PRIMER_THREE 3' seq
(SEQ ID NOs: 62, 63)
LEFT PRIMER 4 22 56.88 36.36 8.00 2.00 TCTAACAAAGCTCTGTCCAAAA
RIGHT PRIMER 148 21 56.12 42.86 3.00 1.00 CCACACTGAATAACTGGAACA
SEQUENCE SIZE: 174
INCLUDED REGION SIZE: 174

PRODUCT SIZE: 145, PAIR ANY COMPL: 4.00, PAIR 3' COMPL: 1.00

1 GTATCTAACAAAGCTCTGTCCAAAATTTTGAATTTCTCGTTAAAaGCATCATGATTATAG
>>>>>>>>>>>>>>>>>>>>>>

61 AACAGAGGTTACAATCAATTATTCAGTCACACAATCACTCTCATCAGTCATTAAGGTGCg

121 TACCTGGTGTTCCAGTTATTCAGTGTGGTATAACAAACTACCTGGAACTTAATG
<<<<<<<<<<<<<<<<<<<<<

4th group

TABLE 2-continued

```
21) Whole sequence ::: rs189900-rs2221492

AGAGTGGTTAAGTGACTTGATCAATTCCTCAGGTGGGGATTCAAGCTCTTAAAGCTGTAG
ACTATGTCGTCCAAACAAAcACTGACATGAATATGACTTCCAATAGGCAAGAAAAGAGGC
CTAGGTCgAGATACTGCAAGACATGCAAGCAATCTAGTAATGGCATAAAACCTGCTATCC
GAATTGGCTAAAATTATGTATT (SEQ ID NO: 64)

OLIGO start len tm gc % any http://fokker.wi.mit.edu/cgi-
bin/primer3/primer3_www_results_help.cgi - PRIMER_THREE 3' seq
(SEQ ID NOs: 65, 66)
LEFT PRIMER      32  20  59.13  50.00  4.00  2.00 GGTGGGGATTCAAGCTCTTA
RIGHT PRIMER    180  22  59.38  40.91  5.00  3.00 GGATAGCAGGTTTTATGCCATT
SEQUENCE SIZE: 202
INCLUDED REGION SIZE: 202

PRODUCT SIZE: 149, PAIR ANY COMPL: 4.00, PAIR 3' COMPL: 1.00

   1 AGAGTGGTTAAGTGACTTGATCAATTCCTCAGGTGGGGATTCAAGCTCTTAAAGCTGTAG
                 >>>>>>>>>>>>>>>>>>>>

  61 ACTATGTCGTCCAAACAAAcACTGACATGAATATGACTTCCAATAGGCAAGAAAAGAGGC

 121 CTAGGTCgAGATACTGCAAGACATGCAAGCAATCTAGTAATGGCATAAAACCTGCTATCC
                   <<<<<<<<<<<<<<<<<<<<

 181 GAATTGGCTAAAATTATGTATT

22) Whole sequence ::: rs2827920-rs2827921

TTCTTTCTCACACAATGGGTTCCATTCCCACTACTACTCCATTCAAATTGAAGTGCCTTC
aATGATTATTAAAAAACTCTCTTTAAAATAGCTCAcGTAACCTTACATCCTTTGACTGAG
GCTCAACTCATGTCAATGCTTCAGTATCAACTTTTC (SEQ ID NO: 67)

OLIGO start len tm gc % any http://frodo.wi.mit.edu/cgi-
bin/primer3/primer3_www_results_help.cgi - PRIMER_THREE 3' seq
(SEQ ID NOs: 68, 69)
LEFT PRIMER      14  21  59.93  47.62  7.00  0.00 AATGGGTTCCATTCCCACTAC
RIGHT PRIMER    125  20  58.96  50.00  7.00  1.00 TGAGCCTCAGTCAAAGGATG
SEQUENCE SIZE: 156
INCLUDED REGION SIZE: 156

PRODUCT SIZE: 112, PAIR ANY COMPL: 4.00, PAIR 3' COMPL: 1.00

   1 TTCTTTCTCACACAATGGGTTCCATTCCCACTACTACTCCATTCAAATTGAAGTGCCTTC
          >>>>>>>>>>>>>>>>>>>>

  61 aATGATTATTAAAAAACTCTCTTTAAAATAGCTCAcGTAACCTTACATCCTTTGACTGAG
                       <<<<<<<<<<<<<<<

 121 GCTCAACTCATGTCAATGCTTCAGTTCAACTTTTC
   <<<<<

23) Whole sequence ::: rs198047-rs2827935

ATTTGTAATAACATTTAGTAAGTATTTATTTGAGGAGTTTGAATTTTGTTCTTGTTTATC
TTGTTCTCTTTCTTcGTAGATTAGTTGGTGTTAACATCAATAGGATAACCCTTTCTTTCA
GCATATGTGAATGAAATaAACCAATTATTGCCACTTTCCAGGTTAACCAGAATATACATA
GATACGAGGACAGTGGACTGTT (SEQ ID NO: 70)

OLIGO start len tm gc % any http://fokker.wi.mit.edu/cgi-
bin/primer3/primer3_www_results_help.cgi - PRIMER_THREE 3' seq
(SEQ ID NOs: 71, 72)
LEFT PRIMER      30  22  56.07  31.82  4.00  1.00 TTGAGGAGTTTGAATTTTGTTC
RIGHT PRIMER    164  20  57.22  40.00  3.00  1.00 AACCTGGAAAGTGGCAATAA
SEQUENCE SIZE: 202
INCLUDED REGION SIZE: 202

PRODUCT SIZE: 135, PAIR ANY COMPL: 3.00, PAIR 3' COMPL: 2.00

   1 ATTTGTAATAACATTTAGTAAGTATTTATTTGAGGAGTTTGAATTTTGTTCTTGTTTATC
                 >>>>>>>>>>>>>>>>>>>>

  61 TTGTTCTCTTTCTTcGTAGATTAGTTGGTGTTAACATCAATAGGATAACCCTTTCTTTCA

 121 GCATATGTGAATGAAATaAACCAATTATTGCCACTTTCCAGGTTAACCAGAATATACATA
             <<<<<<<<<<<<<<<<<<<<

 181 CATACGAGGACGTGGACTGTT
```

TABLE 2-continued

```
24) Whole sequence ::: rs9978999-rs9979175

tagggcagagagagcaagcaagctctctaccttctcatataagggcactaatcccaccat
gaaggcgccactgtcatgacCtgattatgtcacaaagaccccggggcaaatattaccact
Gtgaggagtacagtttttagcatgtgaattttggaagaacacaaacatttag (SEQ ID NO: 73)

OLIGO start len tm gc % any http://frodo.wi.mit.edu/cgi-
bin/primer3/primer3_www_results_help.cgi - PRIMER_THREE 3' seq
(SEQ ID NOs: 74, 75)
LEFT PRIMER      14  21  58.50  52.38  4.00 0.00 gcaagcaagctctctaccttc
RIGHT PRIMER    160  22  59.98  36.38  4.00 2.00 tgttcttccaaaattcacatgc
SEQUENCE SIZE: 171
INCLUDED REGION SIZE: 171

PRODUCT SIZE: 147, PAIR ANY COMPL: 3.00, PAR 3' COMPL: 0.00

   1 tagggcagagagagcaagcaagctctctaccttctcatataagggcactaatcccaccat
             >>>>>>>>>>>>>>>>>>>>

  61 gaaggcgccactgtcatgacCtgattatgtcacaaagaccccggggcaaatattaccact

 121 Gtgaggagtacagttttagcatgtgaattttggaagaacacaaacatttag
             <<<<<<<<<<<<<<<<<<<<

25) Whole sequence ::: rs1034346-rs12481852

ATTCTAATTTTAAATATCATTGATGTAGAACATTCTATTTCACTATTCCTTCATTTTATT
aTTATGGGAAATTATATACAGTTCTCCAGATTTTTAAAGCCTTGCTAACATGTTTTAAGT
CACACAAATATTCTcCTGTGGGAAAATGACAGTAATTTAGTGTGCAACAATTATATAGAA
CTATTTTTCAAACTT (SEQ ID NO: 76)

OLIGO start len tm gc % any http://frodo.wi.mit.edu/cgi-
bin/primer3/primer3_www_results_help.cgi - PRIMER_THREE 3' seq
(SEQ ID NOs: 77, 78)
LEFT PRIMER      37  21  50.04  23.81  2.00 0.00 ATTTCACTATTCCTTCATTTT
RIGHT PRIMER    173  22  50.19  27.27  6.00 3.00 TAATTGTTGCACACTAAATTAC
SEQUENCE SIZE: 195
INCLUDED REGION SIZE: 195

PRODUCT SIZE: 137, PAIR ANY COMPL: 4.00, PAIR 3' COMPL: 2.00

   1 ATTCTAATTTTAAATATCATTGATGTAGAACATTCTATTTCACTATTCCTTCATTTTATT
                     >>>>>>>>>>>>>>>>>>>>

  61 aTTATGGGAAATTATATACAGTTCTCCAGATTTTTAAAGCCTTGCTAACATGTTTTAAGT

 121 CACACAAATATTCTcCTGTGGGAAAATGACAGTAATTTAGTGTGCAACAATTATATAGAA
                 <<<<<<<<<<<<<<<<<<<<

 181 CTATTTTTCAAACTT
```

5th group

```
26) Whole sequence ::: rs7509629-rs2828358

ACTGTCATGGACTTAAACAATTGTCTTTGAATTGTCTTTTTTCATACTTTTATTTGCATC
TTTcCACTAAAAAGATGgCACAAAGTAATCCTAGTTTACATTTTTTACCATGTAATTCCA
TATTACTTTTTCCTGAAA (SEQ ID NO: 79)

OLIGO start len tm gc % any http://frodo.wi.mit.edu/cgi-
bin/primer3/primer3_www_results_help.cgi - PRIMER_THREE 3' seq
(SEQ ID NOs: 80, 81)
LEFT PRIMER       1  20  50.46  35.00  4.00 0.00 ACTGTCATGGACTTAAACAA
RIGHT PRIMER    137  22  53.49  27.27  4.00 0.00 TTCAGGAAAAAGTAATATGGAA
SEQUENCE SIZE: 138
INCLUDED REGION SIZE: 138

PRODUCT SIZE: 137, PAIR ANY COMPL: 4.00, PAIR 3' COMPL: 0.00

   1 ACTGTCATGGACTTAAACAATTGTCTTTGAATTGTCTTTTTTCATACTTTTATTTGCATC
     >>>>>>>>>>>>>>>>>>>>

  61 TTTcCACTAAAAAGATGgCACAAAGTAATCCTAGTTTACATTTTTTACCATGTAATTCCA
                           <<<<<

 121 TATTACTTTTTCCTGAAA
   <<<<<<<<<<<<<<<
```

6th group

TABLE 2-continued

27) Whole sequence ::: rs4817013-rs7277036 aaagaaaaaaaagccacagaaatcagtcctagagaaaacCgatctatgagctgcctgaAa
ataattataaaataactatcataaaaatgcccagtgagatataagaaaacacagacaac
(SEQ ID NO: 82)

OLIGO    start len tm    gc %  any  http://frodo.wi.mit.edu/cgi-
bin/primer3/primer3_www_results_help.cgi - PRIMER_THREE 3' seq
(SEQ ID NOs: 83, 84)
LEFT PRIMER      8  21  56.10  38.10  4.00  2.00 aaaaagccacagaaatcagtc
RIGHT PRIMER   107  22  55.60  36.36  4.00  2.00 ttcttatatctcactgggcatt
SEQUENCE SIZE: 119
INCLUDED REGION SIZE: 119

PRODUCT SIZE: 100, PAIR ANY COMPL: 5.00, PAIR 3' COMPL: 1.00

1 aaagaaaaaaaagccacagaaatcagtcctagagaaaacCgatctatgagctgcctgaAa
         >>>>>>>>>>>>>>>>>>>>

61 ataattataaaataactatcataaaaatgcccagtgagatataagaaaacacagacaac
                         <<<<<<<<<<<<<<<<<<<<<<

28) Whole sequence ::: rs9981121-rs2829696

CAAGGTCAGAGAAGTTATCTTGGATGGTAGAAGAGAAGAAAGGAGAAGAAaGGATAAGCA
GAAAATCAAAAAGGGCATAAAAAAATTACTGGgGAAAATAATTCTTAGTCACTCACCATT
TCTTATGTTTGTGAAAACAGAAA (SEQ ID NO: 85)

OLIGO    start len tm    gc %  any  http://frodo.wi.mit.edu/cgi-
bin/primer3/primer3_www_results_help.cgi - PRIMER_THREE 3' seq
(SEQ ID NOs: 86, 87)
LEFT PRIMER     22  22  56.24  45.45  2.00  0.00 GGATGGTAGAAGAGAAGAAAGG
RIGHT PRIMER   134  22  55.74  31.82  4.00  1.00 TCACAAACATAAGAAATGGTGA
SEQUENCE SIZE: 143
INCLUDED REGION SIZE: 143

PRODUCT SIZE: 113, PAIR ANY COMPL: 3.00, PAIR 3' COMPL: 0.00

1 CAAGGTCAGAGAAGTTATCTTGGATGGTAGAAGAGAAGAAAGGAGAAGAAaGGATAAGCA
                             >>>>>>>>>>>>>>>>>>>>>>

61 GAAAATCAAAAAGGGCATAAAAAAATTACTGGgGAAAATAATTCTTAGTCACTCACCATT
                                                          <<<<<<<<

121 TCTTATGTTTGTGAAAACAGAAA
         <<<<<<<<<<<<<<

29) Whole sequence ::: rs455921-rs2898102 gaccacaattcacaaatgcaaagatgcagaaccaacctaagtggccaCtgactaatgaga
ggataaagaagatgtggcatatataTatcagggactactactcagccattacaaggaaca
aaataatgtcttttgc (SEQ ID NO: 88)

OLIGO    start len tm    gc %  any  http://frodo.wi.mit.edu/cgi-
bin/primer3/primer3_www_results_help.cgi - PRIMER_THREE 3' seq
(SEQ ID NOs: 89, 90)
LEFT PRIMER     17  20  59.85  45.00  4.00  0.00 tgcaaagatgcagaaccaac
RIGHT PRIMER   123  22  59.63  36.36  2.00  1.00 ttttgttccttgtaatggctga
SEQUENCE SIZE: 136
INCLUDED REGION SIZE: 136

PRODUCT SIZE: 107, PAIR ANY COMPL: 6.00, PAIR 3' COMPL: 1.00

1 gaccacaattcacaaatgcaaagatgcagaaccaacctaagtggccaCtgactaatgaga
                      >>>>>>>>>>>>>>>>>>>>

61 ggataaagaagatgtggcatatataTatcagggactactactcagccattacaaggaaca
                                             <<<<<<<<<<<<<<<<<<<<<<

121 aaataatgtcttttgc
         <<<

TABLE 2-continued

30) Whole sequence ::: rs2898102-rs458848 gaccacaattcacaaatgcaaagatgcagaaccaacctaagtggccactgactaatgaga
ggataaagaagatgtggcatatataCatcagggactactTctcagccattacaaggaaca
aaataatgtcttttgcaacaacttggatagagctggaggc (SEQ ID NO: 91)

OLIGO start len tm gc % any http://frodo.wi.mit.edu/cgi-bin/primer3/primer3_www_results_help.cgi - PRIMER_THREE 3' seq
(SEQ ID NOs: 92, 93)
LEFT PRIMER 17 20 59.85 45.00 4.00 0.00 tgcaaagatgcagaaccaac
RIGHT PRIMER 160 21 59.86 52.38 4.00 3.00 gcctccagctctatccaagtt
SEOUENCE SIZE: 160
INCLUDED REGION SIZE: 160

PRODUCT SIZE: 144, PAIR ANY COMPL: 4.00, PAIR 3' COMPL: 3.00

1 gaccacaattcacaaatgcaaagatgcagaaccaacctaagtggccactgactaatgaga
>>>>>>>>>>>>>>>>>>>>

61 ggataaagaagatgtggcatatataCatcagggactactTctcagccattacaaggaaca 121 aaataatgtcttttgcaacaacttggatagagctggaggc
<<<<<<<<<<<<<<<<<<<<<

31) Whole sequence ::: rs961301-rs2830208

AATCCTAGACCTTGGATTGCAAGAGACTCCTTAATATCTTCCCATGTCCACATTTcCTTC
ACATGATTTGAATGTGGCTTCTATTATATACAGATACAAGATTCAAATCCAACCTCTAtG
ATGACTGGTCTTGTGAATAAGCAGAAGAGGCACTAACAAT (SEQ ID NO: 94)

OLIGO start len tm gc % any http://frodo.wi.mit.edu/cgi-bin/primer3/primer3_www_results_help.cgi - PRIMER_THREE 3' seq
(SEQ ID NOs: 95, 96)
LEFT PRIMER 29 22 57.95 40.91 4.00 2.00 CCTTAATATCTTCCCATGTCCA
RIGHT PRIMER 160 22 57.35 40.91 3.00 0.00 ATTGTTAGTGCCTCTTCTGCTT
SEQUENCE SIZE: 160
INCLUDED REGION SIZE: 160

PRODUCT SIZE: 132, PAIR ANY COMPL: 3.00, PAIR 3' COMPL: 1.00

1 AATCCTAGACCTTGGATTGCAAGAGACTCCTTAATATCTTCCCATGTCCACATTTcCTTC
>>>>>>>>>>>>>>>>>>>>>>

61 ACATGATTTGAATGTGGCTTCTATTATATACAGATACAAGATTCAAATCCAACCTCTAtG

121 ATGACTGGTCTTGTGAATAAGCAGAAGAGGCACTAACAAT
<<<<<<<<<<<<<<<<<<<<<<

32) Whole sequence ::: rs2174536-rs458076

AAGAGAAGTGAGGTCAGCAGCTGCAAGCCACCTCCGTCATTTAGAAAAGCTTCaTGATGT
AGTGTGTCGTTTCGATGTGACACTGTCTCACAGAGTTAAAATGATGTtAAGGAACTGTTC
AATGGAAATTTAGAAATTTCTCTTTTTCTCAATTTTAGTGTA (SEQ ID NO: 97)

OLIGO start len tm gc % any http://frodo.wi.mit.edu/cgi-bin/primer3/primer3_www_results_help.cgi - PRIMER_THREE 3' seq
(SEQ ID NOs: 98, 99)
LEFT PRIMER 3 20 57.31 55.00 5.00 5.00 GAGAAGTGAGGTCAGCAGCT
RIGHT PRIMER 136 22 53.92 27.27 6.00 2.00 TTTCTAAATTTCCATTGAACAG
SEQUENCE SIZE: 162
INCLUDED REGION SIZE: 162

PRODUCT SIZE: 134, PAIR ANY COMPL: 4.00, PAIR 3' COMPL: 2.00

1 AAGAGAAGTGAGGTCAGCAGCTGCAAGCCACCTCCGTCATTTAGAAAAGCTTCaTGATGT
>>>>>>>>>>>>>>>>>>>>

61 AGTGTGTCGTTTCGATGTGACACTGTCTCACAGAGTTAAAATGATGTtAAGGAACTGTTC
<<<<<<

121 AATGGAAATTTAGAAATTTCTCTTTTTCTCAATTTTAGTGTA
<<<<<<<<<<<<<<<<

TABLE 2-continued

33) Whole sequence ::: rs432557-rs1012766

ATGGCTGAATAGTATTCCCTTGTGTATATATCTaTTTATCCTTTTATTCATTGATGGACA
CTTAGGCTGATTTTCTCTCTTCTCATGGCTGGCTTCTCATCACCCTTTGGTCCTCCTGTA
TCCTGgTGTAATAAAGCTCTTCCCCAATATCTCGATAGAT (SEQ ID NO: 100)

OLIGO start len tm gc % any http://frodo.wi.mit.edu/cgi-bin/primer3/primer3_www_results_help.cgi - PRIMER_THREE 3' seq (SEQ ID NOs: 101, 102)

```
LEFT PRIMER      3  22  57.77  45.45  9.00  0.00 GGCTGAATAGTATTCCCTTGTG
RIGHT PRIMER   155  20  59.22  50.00  4.00  2.00 TCGAGATATTGGGGAAGAGC
SEQUENCE SIZE: 160
INCLUDED REGION SIZE: 160

PRODUCT SIZE: 153, PAIR ANY COMPL: 5.00, PAIR 3' COMPL: 1.00

   1 ATGGCTGAATAGTATTCCCTTGTGTATATATCTaTTTATCCTTTTATTCATTGATGGACA
       >>>>>>>>>>>>>>>>>>>>

  61 CTTAGGCTGATTTTCTCTCTTCTCATGGCTGGCTTCTCATCACCCTTTGGTCCTCCTGTA

 121 TCCTGgTGTAATAAAGCTCTTCCCCAATATCTCGATAGAT
          <<<<<<<<<<<<<<<<<<<<
```

34) Whole sequence ::: rs10222076-rs10222075 cattttaacttgattacctccacaaagactattccagaataaggttatgttctgaggtat
taggggttacAacttcaacatatgaattttgagtggacacaattcaacccatagcaCCTC
CGTGTAAGAGCTGGGAAGGGAAAGTGGCTAAGTTGTGCAAATGTGCACATTGGTTGGAGA
TGATTAACTTCTGGCATGT (SEQ ID NO: 103)

OLIGO start len tm gc % any http://frodo.wi.mit.edu/cgi-bin/primer3/primer3_www_results_help.cgi - PRIMER_THREE 3' seq (SEQ ID NOs: 104, 105)

```
LEFT PRIMER     17  22  58.32  45.45  4.00  2.00 cctccacaaagactattccaga
RIGHT PRIMER   146  20  60.76  55.00  4.00  2.00 CACTTTCCCTTCCCAGCTCT
SEQUENCE SIZE: 199
INCLUDED REGION SIZE: 199

PRODUCT SIZE: 130, PAIR ANY COMPL: 4.00, PAIR 3' COMPL: 3.00

   1 cattttaacttgattacctccacaaagactattccagaataaggttatgttctgaggtat
                    >>>>>>>>>>>>>>>>>>>>

  61 taggggttacAacttcaacatatgaattttgagtggacacaattcaacccatagcaCCTC

 121 CGTGTAAGAGCTGGGAAGGGAAAGTGGCTAAGTTGTGCAAATGTGCACATTGGTTGGAGA
       <<<<<<<<<<<<<<<<<<<<

 181 TGATTAACTTCTGGCATGT
```

35) Whole sequence ::: rs11088023-rs11088024 aggggaaattggcaatctgattctaaaattcataCggaaaaaaacaatggagttagaat
aactaaaacaagtccgaaaaagaaaaagaaatggaggactaatgctacctgatttcaagt
cttatcTtataaatctacatcaataaaggacaagttg (SEQ ID NO: 106)

OLIGO start len tm gc % any http://frodo.wi.mit.edu/cgi-bin/primer3/primer3_www_results_help.cgi - PRIMER_THREE 3' seq (SEQ ID NOs: 107, 108)

```
LEFT PRIMER      6  20  54.34  35.00  7.00  3.00 gaaattggcaatctgattct
RIGHT PRIMER   157  21  51.94  33.33  5.00  0.00 caacttgtcctttattgatgt
SEQUENCE SIZE: 157
INCLUDED REGION SIZE: 157

PRODUCT SIZE: 152, PAIR ANY COMPL: 4.00, PAR 3' COMPL: 0.00

   1 aggggaaattggcaatctgattctaaaattcataCggaaaaaaacaatggagttagaat
        >>>>>>>>>>>>>>>>>>>>

  61 aactaaaacaagtccgaaaaagaaaaagaaatggaggactaatgctacctgatttcaagt

 121 cttatcTtataaatctacatcaataaaggacaagttg
             <<<<<<<<<<<<<<<<<<<<
```

TABLE 2-continued

36) Whole sequence ::: rs1011734-rs1011733

TCTGTGTTTGTCTATGTTGATAAAACATTGAAATGCCAaATAGCTCAAAGGTCATTCACT
TAAGAAATCTAAGTACTGATAACATCTTAGCCCCGATTCTTCATAGGCATTGTTAAGCCT
ATTATAATTTTGGTtCAGAGAGAAGGTAAACTATATTCCAGACAGGCATATAA (SEQ ID NO: 109)

OLIGO start len tm gc % any http://frodo.wi.mit.edu/cgi-bin/primer3/primer3_www_results_help.cgi - PRIMER_THREE 3' seq (SEQ ID NOs: 110, 111)

```
LEFT PRIMER      12  22  50.06  22.73  6.00  2.00 CTATGTTGATAAAACATTGAAA
RIGHT PRIMER    167  20  51.09  40.00  4.00  2.00 GCCTGTCTGGAATATAGTTT
SEQUENCE SIZE: 173
INCLUDED REGION SIZE: 173

PRODUCT SIZE: 156, PAIR ANY COMPL: 5.00, PAIR 3' COMPL: 3.00

   1 TCTGTGTTTGTCTATGTTGATAAAACATTGAAATGCCAaATAGCTCAAAGGTCATTCACT
         >>>>>>>>>>>>>>>>>>>>

  61 TAAGAAATCTAAGTACTGATAACATCTTAGCCCCGATTCTTCATAGGCATTGTTAAGCCT

 121 ATTATAATTTTGGTtCAGAGAGAAGGTAAACTATATTCCAGACAGGCATATAA
               <<<<<<<<<<<<<<<<<<<<
```

37) Whole sequence ::: rs2831244-rs9789638

TGCAGGGCATATAATCTAAGCTGTAAACGTCCTGTcAGAAGACAACATATTCATCTTGCT
AAGGTtTAAGCTATATGACTGGCACTGTGCTCAACTCAGAGTCATTGAATGAACAGTATT
TATTTA (SEQ ID NO: 112)

OLIGO start len tm gc % any http://frodo.wi.mit.edu/cgi-bin/primer3/primer3_www_results_help.cgi - PRIMER_THREE 3' seq (SEQ ID NOs: 113, 114)

```
LEFT PRIMER       3  22  55.40  40.91  5.00  3.00 CAGGGCATATAATCTAAGCTGT
RIGHT PRIMER    107  21  55.99  47.62  7.00  2.00 CAATGACTCTGAGTTGAGCAC
SEQUENCE SLZE: 126
INCLUDED REGION SIZE: 126

PRODUCT SIZE: 105, PAIR ANY COMPL: 4.00, PAIR 3' COMPL: 2.00

   1 TGCAGGGCATATAATCTAAGCTGTAAACGTCCTGTcAGAAGACAACATATTCATCTTGCT
     >>>>>>>>>>>>>>>>>>>>

  61 AAGGTtTAAGCTATATGACTGGCACTGTGCTCAACTCAGAGTCATTGAATGAACAGTATT
               <<<<<<<<<<<<<<<<<<<<

 121 TATTTA
```

38) Whole sequence ::: rs8132769-rs2831440

TTCACATTATTCCCTTAAAATAAACTCTCTCCCTCCCCTCTCCCGTCTCAaCCTTGTCCC
TTTCTTTATATAATGGGTAATtCGTTAATGTCAGCAGAATAGTTTTGGGGCCATAATGGC
AAGTATCAGTG (SEQ ID NO: 115)

OLIGO start len tm gc % any http://frodo.wi.mit.edu/cgi-bin/primer3/primer3_www_results_help.cgi - PRIMER_THREE 3' seq (SEQ ID NOs: 116, 117)

```
LEFT PRIMER      23  19  56.84  57.89  1.00  0.00 AACTCTCTCCCTCCCCTCT
RIGHT PRIMER    115  20  56.24  40.00  4.00  2.00 TATGGCCCCAAAACTATTCT
SEQUENCE SIZE: 132
INCLUDED REGION SIZE: 132

PRODUCT SIZE: 93, PAIR ANY COMPL: 2.00, PAIR 3' COMPL: 0.00

   1 TTCACATTATTCCCTTAAAATAAACTCTCTCCCTCCCCTCTCCCGTCTCAaCCTTGTCCC
           >>>>>>>>>>>>>>>>>>>>

  61 TTTCTTTATATAATGGGTAATtCGTTAATGTCAGCAGAATAGTTTTGGGGCCATAATGGC
                   <<<<<<<<<<<<<<<<<<<<

 121 AAGTATCAGTG
```

TABLE 2-continued

```
39) Whole sequence ::: rs8134080-rs2831524

TCAGGAAGCAACAAGTACTGGGCAGATTGATACTGTAGCTaGGCTCTAGCTCTATACCTC
TAGAATaaatgttacaaactagcaacttgaaagctaaacctggcccacag (SEQ ID NO: 118)

OLIGO start len tm gc % any http://frodo.wi.mit.edu/cgi-
bin/primer3/primer3_www_results_help.cgi - PRIMER_THREE 3' seq
(SEQ ID NOs: 119, 120)
LEFT PRIMER      11  20  55.75  45.00  6.00 2.00 ACAAGTACTGGGCAGATTGA
RIGHT PRIMER    104  20  56.27  45.00  4.00 2.00 gccaggtttagctttcaagt
SEQUENCE SIZE: 110
INCLUDED REGION SIZE: 110

PRODUCT SIZE: 94, PAIR ANY COMPL: 4.00, PAIR 3' COMPL: 3.00

   1 TCAGGAAGCAACAAGTACTGGGCAGATTGATACTGTAGCTaGGCTCTAGCTCTATACCTC
          >>>>>>>>>>>>>>>>>>>>

  61 TAGAATaaatgttacaaactagcaacttgaaagctaaacctggcccacag
                <<<<<<<<<<<<<<<<<<<<

40) Whole sequence ::: rs4817219-rs4817220

tggttcttgagaattttatatcaggagaaacactgtcagtCtgtattgaaaggaacagag
aaaatTcgaaattaaagaagactattaaacctccaaaattctggca (SEQ ID NO: 121)

OLIGO start len tm gc % any http://frodo.wi.mit.edu/cgi-
bin/primer3/primer3_www_results_help.cgi - PRIMER_THREE 3' seq
(SEQ ID NOs: 122, 123)
LEFT PRIMER      14  22  51.54  31.82  4.00 3.00 ttttatatcaggagaaacactg
RIGHT PRIMER    104  21  55.03  33.33  8.00 2.00 ccagaattttggaggtttaat
SEQUENCE SIZE: 106
INCLUDED REGION SIZE: 106

PRODUCT SiZE: 91, PAIR ANY COMPL: 4.00, PAIR 3' COMPL: 2.00

   1 tggttcttgagaattttatatcaggagaaacactgtcagtCtgtattgaaaggaacagag
               >>>>>>>>>>>>>>>>>>>>

  61 aaaatTcgaaattaaagaagactattaaacctccaaaattctggca
                 <<<<<<<<<<<<<<<<<<<<

41) Whole sequence ::: rs2250911-rs2250997

GCATCAAACTACACACTGTCATTCCTCCTTTATCTCCAAAAGCTTGAAAATTCCTCACTT
GTaTCTCATTCTTTCTCTCTTAGAAAACTGATCACCTCTGATGAATTAgAACGGAATGAC
CAAGCTTTGGGAGAGGCAAAAGAATCTCGGTGTTAAAGACTCAGAGTTTAA (SEQ ID NO: 124)

OLIGO start len tm gc % any http://frodo.wi.mit.edu/cgi-
bin/primer3/primer3_www_results_help.cgi - PRIMER_THREE 3' seq
(SEQ ID NOs: 125, 126)
LEFT PRIMER      17  22  58.65  40.91  3.00 0.00 TGTCATTCCTCCTTTATCTCCA
RIGHT PRIMER    144  20  59.42  45.00  4.00 2.00 TTCTTTTGCCTCTCCCAAAG
SEQUENCE SIZE: 171
INCLUDED REGION SIZE: 171

PRODUCT SIZE: 128, PAIR ANY COMPL: 4.00, PAIR 3' COMPL: 0.00

   1 GCATCAAACTACACACTGTCATTCCTCCTTTATCTCCAAAAGCTTGAAAATTCCTCACTT
             >>>>>>>>>>>>>>>>>>>>

  61 GTaTCTCATTCTTTCTCTCTTAGAAAACTGATCACCTCTGATGAATTAgAACGGAATGAC

 121 CAAGCTTTGGGAGAGGCAAAAGAATCTCGGTGTTAAAGACTCAGAGTTTAA
        <<<<<<<<<<<<<<<<<<<<
```

TABLE 2-continued

```
42) Whole sequence ::: rs2831899-rs2831900

TTGAAAATTAAGAAACCCTGGCACAGTGTTGACTGGAGCCaCTTACCTTAATAGAAAATA
AAGCTCACATATATCCATAATGAAAAGCAGAGACCAGCACAACCATAGTCACCTGACAGT
TTtAAAATCCAAGGCCAGGATCTTCTCAACTCAGGCCCACTCA (SEQ ID NO: 127)

OLIGO start len tm gc % any http://frodo.wi.mit.edu/cgi-
bin/primer3/primer3_www_results_help.cgi - PRIMER_THREE 3' seq
(SEQ ID NOs: 128, 129)
LEFT PRIMER       15  20  60.63  55.00  6.00  2.00 ACCCTGGCACAGTGTTGACT
RIGHT PRIMER     159  20  59.80  50.00  4.00  2.00 TGGGCCTGAGTTGAGAAGAT
SEQUENCE SIZE: 163
INCLUDED REGION SIZE: 163

PRODUCT SIZE: 145, PAIR ANY COMPL: 5.00, PAIR 3' COMPL: 1.00

   1 TTGAAAATTAAGAAACCCTGGCACAGTGTTGACTGGAGCCaCTTACCTTAATAGAAAATA
                   >>>>>>>>>>>>>>>>>>>>

  61 AAGCTCACATATATCCATAATGAAAAGCAGAGACCAGCACAACCATAGTCACCTGACAGT

 121 TTtAAAATCCAAGGCCAGGATCTTCTCAACTCAGGCCCACTCA
                       <<<<<<<<<<<<<<<<<<<<

43) Whole sequence ::: rs2831902-rs2831903

CACATAACTAATAAATTTGTAAGTATGTGCAACGGCTCACaCTTGCTTCCAGAATGGCAC
CTAAAAAACAGATTTACCTCTCCCCAAATTCAGATATGGAATTAAATGTAATGTCAGGAA
AAcTGTCTAAGAGTTGGAAATGGGAAAAAAATGTTCTTTTGGT (SEQ ID NO: 212)

OLIGO start len tm gc % any http://frodo.wi.mit.edu/cgi-
bin/primer3/primer3_www_results_help.cgi - PRIMER_THREE 3' seq
(SEQ ID NOs: 213, 130)
LEFT PRIMER       14  21  53.16  33.33  4.00  2.00 AATTTGTAAGTATGTGCAACG
RIGHT PRIMER     149  20  56.27  35.00  2.00  0.00 TTTTTCCCATTTCCAACTCT
SEQUENCE SIZE: 163
INCLUDED REGION SIZE: 163

PRODUCT SIZE: 136, PAIR ANY COMPL: 4.00, PAIR 3' COMPL: 2.00

   1 CACATAACTAATAAATTTGTAAGTATGTGCAACGGCTCACaCTTGCTTCCAGAATGGCAC
                  >>>>>>>>>>>>>>>>>>>>>

  61 CTAAAAAACAGATTTACCTCTCCCCAAATTCAGATATGGAATTAAATGTAATGTCAGGAA

 121 AAcTGTCTAAGAGTTGGAAATGGGAAAAAAATGTTCTTTTGGT
              <<<<<<<<<<<<<<<<<<<<

44) Whole sequence ::: rs11088086-rs2251447

AAAAAAAAAGATGAGACAGGCAGGTGCGAAAGAAATAAAAGTCAaAACTGATCCAGTTGG
GAAACTCAGAATTGACAGTTAcGTGTCCTTTCATTTATTGATATTTTGAGATTCACAGGG
GT (SEQ ID NO: 131)

OLIGO start len tm gc % any http://frodo.wi.mit.edu/cgi-
bin/primer3/primer3_www_results_help.cgi - PRIMER_THREE 3' seq
(SEQ ID NOs: 132, 133)
LEFT PRIMER        6  20  56.41  45.00  2.00  2.00 AAAAGATGAGACAGGCAGGT
RIGHT PRIMER     122  20  55.99  40.00  5.00  2.00 ACCCCTGTGAATCTCAAAAT
SEQUENCE SIZE: 122
INCLUDED REGION SIZE: 122

PRODUCT SIZE: 117, PAIR ANY COMPL: 5.00, PAIR 3' COMPL: 2.00

   1 AAAAAAAAAGATGAGACAGGCAGGTGCGAAAGAAATAAAAGTCAaAACTGATCCAGTTGG
          >>>>>>>>>>>>>>>>>>>>

  61 GAAACTCAGAATTGACAGTTAcGTGTCCTTTCATTTATTGATATTTTGAGATTCACAGGG
                                <<<<<<<<<<<<<<<<<<

 121 GT
   <<
```

TABLE 2-continued

45) Whole sequence ::: rs2832040-rs11088088

GAGTTAAATAAAGCACTTGCTTCTATTGTTTGTACCTAAACTTAACAGAAcACAGTAAGT
AACAAGTCATTGGGATGCAGAAAAGAAAAAAGAGAGTGAAGGAAGGAGAgAAGGTGAAGG
GAGAATGGAAGAGAGGAAGGGAGGGAGGAA (SEQ ID NO: 134)

OLIGO start len tm gc % any http://frodo.wi.mit.edu/cgi-bin/primer3/primer3_www_results_help.cgi - PRIMER_THREE 3' seq
(SEQ ID NOs: 135, 136)

```
LEFT PRIMER      13  21  54.81  38.10  4.00  0.00 GCACTTGCTTCTATTGTTTGT
RIGHT PRIMER    141  20  57.37  50.00  2.00  0.00 CCCTTCCTCTCTTCCATTCT
SEQUENCE SIZE: 150
INCLUDED REGION SIZE: 150

PRODUCT SIZE: 129, PAIR ANY COMPL: 2.00, PAIR 3' COMPL: 0.00

   1 GAGTTAAATAAAGCACTTGCTTCTATTGTTTGTACCTAAACTTAACAGAAcACAGTAAGT
         >>>>>>>>>>>>>>>>>>>>

  61 AACAAGTCATTGGGATGCAGAAAAGAAAAAAGAGAGTGAAGGAAGGAGAgAAGGTGAAGG

 121 GAGAATGGAAGAGAGGAAGGGAGGGAGGAA
   <<<<<<<<<<<<<<<<<<<<
```

46) Whole sequence ::: rs2832141-rs2246777 aaacgagccaccagtgggAGCACTGCAGGTATCTGTGTGAGACCcGTACTTCACAACTCC
TGCTTTCCCTCCATAAAGtAGCTTGCATTTTCCACATTGACTTTGCAGTTCTTTGGTATC
TGTATTGGT (SEQ ID NO: 137)

OLIGO start len tm gc % any http://frodo.wi.mit.edu/cgi-bin/primer3/primer3_www_results_help.cgi - PRIMER_THREE 3' seq
(SEQ ID NOs: 138, 139)

```
LEFT PRIMER      14  18  58.28  61.11  6.00  2.00 gtgggAGCACTGCAGGTA
RIGHT PRIMER    123  21  55.05  38.10  4.00  2.00 ACAGATACCAAAGAACTGCAA
SEQUENCE SIZE: 129
INCLUDED REGION SIZE: 129

PRODUCT SIZE: 110, PAIR ANY COMPL: 5.00, PAIR 3' COMPL: 3.00

   1 aaacgagccaccagtgggAGCACTGCAGGTATCTGTGTGAGACCcGTACTTCACAACTCC
           >>>>>>>>>>>>>>>>>>>>

  61 TGCTTTCCCTCCATAAAGtAGCTTGCATTTTCCACATTGACTTTGCAGTTCTTTGGTATC
                     <<<<<<<<<<<<<<<<<

 121 TGTATTGGT
     <<<
```

47) Whole sequence ::: rs2832959-rs9960934

TGGAGACCTTTCAACTTAGAAATCATAAACAGATTCATTTcCTTAAAGTTAATGaaaaga
attaacagaccctcctcaaaaaagacatatatgcagcctacaatcatatgaaaaaaagtt
caacattactgttcagcaaatcaaa (SEQ ID NO: 140)

OLIGO start len tm gc % any http://frodo.wi.mit.edu/cgi-bin/primer3/primer3_www_results_help.cgi - PRIMER_THREE 3' seq
(SEQ ID NOs: 141, 142)

```
LEFT PRIMER       1  20  53.30  40.00  3.00  3.00 TGGACACCTTTCAACTTAGA
RIGHT PRIMER    134  22  50.67  27.27  8.00  3.00 gaacagtaatgttgaacttttt
SEQUENCE SIZE: 145
INCLUDED REGION SIZE: 145

PRODUCT SIZE: 134, PAIR ANY COMPL: 7.00, PAIR 3' COMPL: 3.00

   1 TGGAGACCTTTCAACTTAGAAATCATAAACAGATTCATTTcCTTAAAGTTAATGaaaaga
     >>>>>>>>>>>>>>>>>>>>

  61 attaacagaccctcctcaaaaaagacatatatgcagcctacaatcatatgaaaaaaagtt
                                 <<<<<<<<

 121 caacattactgttcagcaaatcaaa
    <<<<<<<<<<<<
```

$7^{th}$ group

TABLE 2-continued

```
48) Whole sequence ::: rs2833734-rs2833735

TGGATACATTCCTAGAAATAGATGGAAACTGCTCTTGCAAAAAGCTTAGCACATGTTAAA
aATTTTAGAAACAATTTGCCAAAGTTTATTTAGTCTAGTGATTTtGACAGGTTAAATGGA
CCCTTTGAGATCTTTTTTCCTCAAGTACAAAGGCT (SEQ ID NO: 143)

OLIGO start len tm gc % any http://frodo.wi.mit.edu/cgi-
bin/primer3/primer3_www_results_help.cgi - PRIMER_THREE 3' seq
(SEQ ID NOs: 144, 145)
LEFT PRIMER      33  21  58.90  38.10  6.00  2.00 TCTTGCAAAAAGCTTAGCACA
RIGHT PRIMER    137  21  57.77  38.10  6.00  1.00 AAAAAGATCTCAAAGGGTCCA
SEQUENCE SIZE: 155
INCLUDED REGION SIZE: 155

PRODUCT SIZE: 105, PAIR ANY COMPL: 4.00, PAIR 3' COMPL: 0.00

   1 TGGATACATTCCTAGAAATAGATGGAAACTGCTCTTGCAAAAAGCTTAGCACATGTTAAA
                 >>>>>>>>>>>>>>>>>>>>>

  61 aATTTTAGAAACAATTTGCCAAAGTTTATTTAGTCTAGTGATTTtGACAGGTTAAATGGA
                           <<<<

 121 CCCTTTGAGATCTTTTTTCCTCAAGTACAAAGGCT
   <<<<<<<<<<<<<<<<<

49) Whole sequence ::: rs933121-rs933122

GCTTTTGCTGAACATCAAGTGGTGAGCCAGGACTCAAaGCCAGATCTTCTTGTTTCCCTG
TTAGGTGTtTGTAGCACAACTGGTATCTGCAGACTATGCTGCTGGAAGGGCTAGCCGTC
(SEQ ID NO: 146)

OLIGO start len tm gc % any http://frodo.wi.mit.edu/cgi-
bin/primer3/primer3_www_results_help.cgi - PRIMER_THREE 3' seq
(SEQ ID NOs: 147, 148)
LEFT PRIMER       1  20  55.61  40.00  6.00  3.00 GCTTTTGCTGAACATCAAGT
RIGHT PRIMER    109  19  55.56  52.63  3.00  3.00 CCTTCCAGCAGCATAGTCT
SEQUENCE SIZE: 119
INCLUDED REGION SIZE: 119

PRODUCT SIZE: 109, PAIR ANY COMPL: 5.00, PAIR 3' COMPL: 1.00

   1 GCTTTTGCTGAACATCAAGTGGTGAGCCAGGACTCAAaGCCAGATCTTCTTGTTTCCCTG
    >>>>>>>>>>>>>>>>>>>>

  61 TTAGGTGTtTGTAGCACAACTGGTATCTGCAGACTATGCTGCTGGAAGGGCTAGCCGTC
                 <<<<<<<<<<<<<<<<<<<

50) Whole sequence ::: rs2834140-rs12626953

ACTGTCCTAGAAAATCCAGGATGTGCAGTGATCAtGTATGAATGCATGGACCTGCACACA
CAGGAGTGAACAAAAGACCCACCCCTGCCAGGTCACCACTCATATCTCACCCCAGCCCAC
GCTAGCTCACaCTCCTCCCCACACACCACTGACCTCATCAT (SEQ ID NO: 149)

OLIGO start len tm gc % any http://frodo.wi.mit.edu/cgi-
bin/primer3/primer3_www_results_help.cgi - PRIMER_THREE 3' seq
(SEQ ID NOs: 150, 151)
LEFT PRIMER      12  18  53.64  44.44  7.00  1.00 AAATCCAGGATGTGCAGT
RIGHT PRIMER    161  19  53.29  47.37  4.00  0.00 ATGATGAGGTCAGTGGTGT
SEQUENCE SIZE: 161
INCLUDED REGION SIZE: 161

PRODUCT SIZE: 150, PAIR ANY COMPL: 3.00, PAIR 3' COMPL: 0.00

   1 ACTGTCCTAGAAAATCCAGGATGTGCAGTGATCAtGTATGAATGCATGGACCTGCACACA
          >>>>>>>>>>>>>>>>>>

  61 CAGGAGTGAACAAAAGACCCACCCCTGCCAGGTCACCACTCATATCTCACCCCAGCCCAC

 121 GCTAGCTCACaCTCCTCCCCACACACCACTGACCTCATCAT
            <<<<<<<<<<<<<<<<<<<
```

TABLE 2-continued

51) Whole sequence ::: rs2834485-rs3453

CACATCACAGATCATAGTAAATGGCTTTAATTTTTTAaCGAAATCTCACTACTGCAAATG
CATTGTTGTCCTAGCTAATGAATGCAtAGAGTATTGCCTGCAAAATAATAATTGAGATTC
TATT (SEQ ID NO: 152)

OLIGO start len tm gc % any http://frodo.wi.mit.edu/cgi-bin/primer3/primer3_www_results_help.cgi - PRIMER_THREE 3' seq (SEQ ID NOs: 153, 154)

```
LEFT PRIMER       3  22  52.35  36.36  4.00 0.00 CATCACAGATCATAGTAAATGG
RIGHT PRIMER    113  21  53.50  23.81  6.00 4.00 AATTATTATTTTGCAGGCAAT
SEQUENCE SIZE: 124
INCLUDED REGION SIZE: 124

PRODUCT SIZE: 111, PAIR ANY COMPL: 5.00, PAIR 3' COMPL: 2.00

   1 CACATCACAGATCATAGTAAATGGCTTTAATTTTTTAaCGAAATCTCACTACTGCAAATG
     >>>>>>>>>>>>>>>>>>>>

  61 CATTGTTGTCCTAGCTAATGAATGCAtAGAGTATTGCCTGCAAAATAATAATTGAGATTC
                 <<<<<<<<<<<<<<<<<<<<

 121 TATT
```

8th group

52) Whole sequence ::: rs9974956-rs2834703

TTATCCTCCACATCCTCATGAGGCAAACACCTTTCCTACCTTACCGCTCCcCAGTGGCCT
CCCTGTTGCGTTCTTATTCAAGACTAAGACtCTCTAGAATGTTCTTTATCCTGAGTCCAG
CTGATTGTCTATACTAATATCAGTACGGGGT (SEQ ID NO: 155)

OLIGO start len tm gc % any http://frodo.wi.mit.edu/cgi-bin/primer3/primer3_www_results_help.cgi - PRIMER_THREE 3' seq (SEQ ID NOs: 156, 157)

```
LEFT PRIMER      17  20  60.50  50.00  4.00 2.00 CATGAGGCAAACACCTTTCC
RIGHT PRIMER    121  22  58.46  45.45  3.00 0.00 GCTGGACTCAGGATAAAGAACA
SEQUENCE SIZE: 151
INCLUDED REGION SIZE: 151

PRODUCT SIZE: 105, PAIR ANY COMPL: 4.00, PAIR 3' COMPL: 1.00

   1 TTATCCTCCACATCCTCATGAGGCAAACACCTTTCCTACCTTACCGCTCCcCAGTGGCCT
            >>>>>>>>>>>>>>>>>>>>

  61 CCCTGTTGCGTTCTTATTCAAGACTAAGACtCTCTAGAATGTTCTTTATCCTGAGTCCAG
                    <<<<<<<<<<<<<<<<<<<

 121 CTGATTGTCTATACTAATATCAGTACGGGGT
   <
```

53) Whole sequence ::: rs12482353-rs2205032

ATCACCTGGTTTGGTGCATCCTCGCAGAAAGAGAGCCATACAGTGAAGTGGAAACACACCCAAAAGC
TCTGCAATATTCCTAGAAGTTCTCGAATCTCCTCCTTAAcAGAGCTGCAGAAGGGAAACACAGACAGG
AAGCACCTGTTTGACTCAgACAGCAGCCCTAATGCAGTGCCACTCAGGAGCATTCCCTCATTTGAAG
ACCCCCCAATTACATGAAATTATCAACCCC (SEQ ID NO: 346)

OLIGO start len tm gc % any http://frodo.wi.mit.edu/cgi-bin/primer3/primer3_www_results_help.cgi - PRIMER_THREE 3' seq (SEQ ID NOs: 347, 348)

```
LEFT PRIMER      56  20  59.74  45.00  4.00 2.00 ACACCCAAAAGCTCTGCAAT
RIGHT PRIMER    199  20  60.59  50.00  4.00 2.00 CAAATGAGGGAATGCTCCTG
SEQUENCE SIZE: 232
INCLUDED REGION SIZE: 232

PRODUCT SIZE: 144, PAIR ANY COMPL: 3.00, PAIR 3' COMPL: 0.00

   1 ATCACCTGGTTTGGTGCATCCTCGCAGAAAGAGAGCCATACAGTGAAGTGGAAACACACC
                          >>>>>

  61 CAAAAGCTCTGCAATATTCCTAGAAGTTCTCGAATCTCCTCCTTAAcAGAGCTGCAGAAG
    >>>>>>>>>>>>>>>

 121 GGAAACACAGACAGGAAGCACCTGTTTGACTCAgACAGCAGCCCTAATGCAGTGCCACTC
                           <

 181 AGGAGCATTCCCTCATTTGAAGACCCCCCAATTACATGAAATTATCAACCCC
   <<<<<<<<<<<<<<<<<<<
```

TABLE 2-continued

54) Whole sequence ::: rs2776266-rs2835001 agggtgcagcactttattatggaagcctgagctgactaatacaGGTGTCTcTATATCTCA
CTGAGGGAAAGTGACAGGAAAGTAAGAACCATTTaTGTCCAAGAGTCCAGAGGAGTCAAC
CAGATTCTGGGGGAAAGAAGGTAC (SEQ ID NO: 158)

OLIGO start len tm gc % any http://frodo.wi.mit.edu/cgi-bin/primer3/primer3_www_results_help.cgi - PRIMER_THREE 3' seq
(SEQ ID NOs: 159, 160)
LEFT PRIMER 20 20 58.75 50.00 4.00 1.00 tggaagcctgagctgactaa
RIGHT PRIMER 142 20 59.87 50.00 4.00 3.00 CCTTCTTTTCCCCCAGAATC
SEQUENCE SIZE: 145
INCLUDED REGION SIZE: 145

PRODUCT SIZE: 123, PAIR ANY COMPL: 4.00, PAIR 3' COMPL: 0.00

1 agggtgcagcactttattatggaagcctgagctgactaatacaGGTGTCTcTATATCTCA
>>>>>>>>>>>>>>>>>>>>

61 CTGAGGGAAAGTGACAGGAAAGTAAGAACCATTTaTGTCCAAGAGTCCAGAGGAGTCAAC

121 CAGATTCTGGGGGAAAGAAGGTAC
<<<<<<<<<<<<<<<<<<<<

55) Whole sequence ::: rs1984014-rs1984015

TGAGAATTTAGGAGAACAGAAGATCAGAGGGCTGCACaGGCTAAACTAGACAATGAGCCC
ATGCAAGTAAGTTAAGAGGAGAAGCGGGTAAGTATGCACCTGCTTTGTCTAGGtGACCAG
CAAGCATTTAGCAATAGTCTTTTCAAAACAACAG (SEQ ID NO: 161)

OLIGO start len tm gc % any http://frodo.wi.mit.edu/cgi-bin/primer3/primer3_www_results_help.cgi - PRIMER_THREE 3' seq
(SEQ ID NOs: 162, 163)
LEFT PRIMER 8 22 53.09 40.91 4.00 1.00 TTAGGAGAACAGAAGATCAGAG
RIGHT PRIMER 142 22 53.52 31.82 4.00 2.00 AAAGACTATTGCTAAATGCTTG
SEQUENCE SIZE: 154
INCLUDED REGION SIZE: 154

PRODUCT SIZE: 135, PAIR ANY COMPL: 4.00, PAIR 3' COMPL: 2.00

1 TGAGAATTTAGGAGAACAGAAGATCAGAGGGCTGCACaGGCTAAACTAGACAATGAGCCC
>>>>>>>>>>>>>>>>>>>>

61 ATGCAAGTAAGTTAAGAGGAGAAGCGGGTAAGTATGCACCTGCTTTGTCTAGGtGACCAG

121 CAAGCATTTAGCAATAGTCTTTTCAAAACAACAG
<<<<<<<<<<<<<<<<<<<<

56) Whole sequence ::: rs1014593-rs9305569

GGAACTGCAGGAGATCCCTGCTGCCTTCCAGTTCATGGGATGATGGCCTCCACTTCTGCCCCTGTTT
GCTTCTCCTTTGAaATCTTACATGAAGGTATACAGTTTGAAGAAGCCAGTTTGACTCCAATATCTGTGC
AATGGAATACTGCTCATTAAAAAGgAATTAAACTATTGATACACACAACATGGGTGAAGATCAAACTGT
CTCCTTCCCTTTGATTCAAGGGAATCTGAGAAATG (SEQ ID NO: 349)

OLIGO start len tm gc % any http://frodo.wi.mit.edu/cgi-bin/primer3/primer3_www_results_help.cgi - PRIMER_THREE 3' seq
(SEQ ID NOs: 350, 351)
LEFT PRIMER 51 19 59.86 52.63 2.00 0.00 ACTTCTGCCCCTGTTTGCT
RIGHT PRIMER 196 21 58.84 42.86 4.00 3.00 TGATCTTCACCCATGTTGTGT
SEQUENCE SIZE: 239
INCLUDED REGION SIZE: 239

PRODUCT SIZE: 148, PAIR ANY COMPL: 2.00, PAIR 3' COMPL: 0.00

1 GAACTGCAGGAGATCCCTGCTGCCTTCCAGTTCATGGGATGATGGCCTCCACTTCTGCCC
>>>>>>>>>>

61 CTGTTTGCTTCTCCTTTGAaATCTTACATGAAGGTATACAGTTTGAAGAAGCCAGTTTGA
>>>>>>>>>>

121 CTCCAATATCTGTGCAATGGAATACTGCTCATTAAAAAGgAATTAAACTATTGATACACA
<<<

181 CAACATGGGTGAAGATCAAACTGTCTCCTTCCCTTTGATTCAAGGGAATCTGAGAAATG
<<<<<<<<<<<<<<<<<

TABLE 2-continued

```
57) Whole sequence ::: rs7281674-rs2835316

AAACAGGCAAAATAAGCGTAGGGCTGTGTGTGCAACAGTTaATCATAAAGCCATCACCAG
GAGACgTCACTGGGCGCCTTCTGGAGTCATATCCGTCCTAACTTTGC (SEQ ID NO: 164)

OLIGO start len tm gc % any http://frodo.wi.mit.edu/cgi-
bin/primer3/primer3_www_results_help.cgi - PRIMER_THREE 3' seq
(SEQ ID NOs: 165, 166)
LEFT PRIMER      13  20  59.93  55.00  4.00  0.00 TAAGCGTAGGGCTGTGTGTG
RIGHT PRIMER     97  21  60.06  57.14  3.00  1.00 GGACGGATAGACTCCAGAAGG
SEQUENCE SIZE: 106
INCLUDED REGION SIZE: 106

PRODUCT SIZE: 85, PAIR ANY COMPL: 3.00, PAIR 3' COMPL: 0.00

   1 AAACAGGCAAAATAAGCGTAGGGCTGTGTGTGCAACAGTTaATCATAAAGCCATCACCAG
          >>>>>>>>>>>>>>>>>>>>

  61 GAGACgTCACTGGGCGCCTTCTGGAGTCATATCCGTCCTAACTTTGC
           <<<<<<<<<<<<<<<<<<<<<

58) Whole sequence ::: rs13047304-rs13047322

gaatgaccttggcacttttatcaaacatcaactggccacaCacaggtgagtctacttctg
gacacttaTcctgttccattcatctgtatatctctatccttacac (SEQ ID NO: 167)

OLIGO start len tm gc % any http://frodo.wi.mit.edu/cgi-
bin/primer3/primer3_www_results_help.cgi - PRIMER_THREE 3' seq
(SEQ ID NOs: 168, 169)
LEFT PRIMER       1  23  60.36  39.13  3.00  2.00 gaatgaccttggcacttttatca
RIGHT PRIMER    101  27  57.86  33.33  4.00  0.00 aaggatagagatatacagatgaatgga
SEQUENCE SIZE: 105
INCLUDED REGION SIZE: 105

PRODUCT SIZE: 101, PAIR ANY COMPL: 4.00, PAIR 3' COMPL: 1.00

   1 gaatgaccttggcacttttatcaaacatcaactggccacaCacaggtgagtctacttctg
    >>>>>>>>>>>>>>>>>>>>

  61 gacacttaTcctgttccattcatctgtatatctctatccttacac
            <<<<<<<<<<<<<<<<<<<<<

59) Whole sequence ::: rs2835545-rs4816551

CTGCTGGAATAGGCTGCTTGGCCATGTTCTTGGAAGCTACCACCATATCAaGGTAATTTC
CCACACAACATTCCAGCCCCTGCTTTCCtCTCTGGCCTTATCTAGGGCCATTCCCCAACT
CAGGTGAAT (SEQ ID NO: 170)

OLIGO start len tm gc % any http://frodo.wi.mit.edu/cgi-
bin/primer3/primer3_www_results_help.cgi - PRIMER_THREE 3' seq
(SEQ ID NOs: 168, 169)
LEFT PRIMER      20  20  60.21  50.00  4.00  2.00 GGCCATGTTCTTGGAAGCTA
RIGHT PRIMER    126  20  60.89  50.00  5.00  0.00 TTCACCTGAGTTGGGGAATG
SEQUENCE SIZE: 129
INCLUDED REGION SIZE: 129

PRODUCT SIZE: 109, PAIR ANY COMPL: 3.00, PAIR 3' COMPL: 0.00

   1 CTGCTGGAATAGGCTGCTTGGCCATGTTCTTGGAAGCTACCACCATATCAaGGTAATTTC
            >>>>>>>>>>>>>>>>>>>>

  61 CCACACAACATTCCAGCCCCTGCTTTCCtCTCTGGCCTTATCTAGGGCCATTCCCCAACT
                       <<<<<<<<<<<<

 121 CAGGTGAAT
   <<<<<<<<
```

TABLE 2-continued

```
60) Whole sequence ::: rs2835735-rs2835736

ACCTTTGTTCCATGCACCGCGCAAATACCTGGGAACCCTTaTTGCCCAACTCAAGAGCCA
GAGTCCTCTGTCATCATTTTGCCTCTCTCCTAAGTGAgAGGACTGAGTGCAGACTTGGTG
TTTGTGGGTGAGGCATGT (SEQ ID NO: 173)

OLIGO start len tm gc % any http://frodo.wi.mit.edu/cgi-
bin/primer3/primer3_www_results_help.cgi - PRIMER_THREE 3' seq
(SEQ ID NOs: 174, 175)
LEFT PRIMER      11  16  62.22  55.56  5.00  0.00 CATGCACCGCGCAAATAC
RIGHT PRIMER    136  19  59.38  52.63  2.00  0.00 ATGCCTCACCCACAAACAC
SEQUENCE SIZE: 138
INCLUDED REGION SIZE: 138

PRODUCT SIZE: 126, PAIR ANY COMPL: 3.00, PAIR 3' COMPL: 0.00

   1 ACCTTTGTTCCATGCACCGCGCAAATACCTGGGAACCCTTaTTGCCCAACTCAAGAGCCA
         >>>>>>>>>>>>>>>>>>>>

  61 GAGTCCTCTGTCATCATTTTGCCTCTCTCCTAAGTGAgAGGACTGAGTGCAGACTTGGTG
                            <<<

 121 TTTGTGGGTGAGGCATGT
     <<<<<<<<<<<<<<<<<

61) Whole sequence ::: rs13047608-rs2835826

CTCCTGAGTCCAAGCCCTTCTCACTCACCTCTTTCTTGAACTAATTTCTTcCTGTTTTTT
TCCAGTCCTCCCTTCTGTTCATGTCTCTCCTCTGCACACTTCCATTTTgTGGTTCAGAAA
ATGTCACCGTCCCAGTCACACTTGCCTTATGGCTGTTGT (SEQ ID NO: 176)

OLIGO start len tm gc % any http://frodo.wi.mit.edu/cgi-
bin/primer3/primer3_www_results_help.cgi - PRIMER_THREE 3' seq
(SEQ ID NOs: 177, 178)
LEFT PRIMER       9  20  60.39  55.00  4.00  0.00 TCCAAGCCCTTCTCACTCAC
RIGHT PRIMER    135  20  59.97  50.00  3.00  1.00 CTGGGACGGTGACATTTTCT
SEQUENCE SIZE: 159
INCLUDED REGION SIZE: 159

PRODUCT SIZE: 127, PAIR ANY COMPL: 4.00, PAIR 3' COMPL: 0.00

   1 CTCCTGAGTCCAAGCCCTTCTCACTCACCTCTTTCTTGAACTAATTTCTTcCTGTTTTTT
        >>>>>>>>>>>>>>>>>>>>

  61 TCCAGTCCTCCCTTCTGTTCATGTCTCTCCTCTGCACACTTCCATTTTgTGGTTCAGAAA
                           <<<<<

 121 ATGTCACCGTCCCAGTCACACTTGCCTTATGGCTGTTGT
    <<<<<<<<<<<<<<<

62) Whole sequence ::: rs857998-rs17264497

TGGAGAAAGTTGTTGCAAACTGCCCAGAGACCCTGGGAGTCACTCCAGTTTTCTGAAACCCAGATAT
TTCAGtGCCTCAGGAGAGACAAGTCCTGACCTTCTCTCCTCCAGCTCTCCCAGgAGATAGGCAAGCC
CCTAACTCCCTAACTAAGCCCTTACGACCTGAAATCCATTGAGTGGCTTCTTTAC (SEQ ID NO: 352)

OLIGO start len tm gc % any http://frodo.wi.mit.edu/cgi-
bin/primer3/primer3_www_results_help.cgi - PRIMER_THREE 3' seq
(SEQ ID NOs: 353, 354)
LEFT PRIMER      15  16  59.35  61.11  4.00  0.00 GCAAACTGCCCAGAGACC
RIGHT PRIMER    147  20  60.57  55.00  2.00  2.00 TTAGGGAGTTAGGGGCTTGC
SEQUENCE SIZE: 189
INCLUDED REGION SIZE: 189

PRODUCT SIZE: 133, PAIR ANY COMPL: 5.00, PAIR 3' COMPL: 2.00

   1 TGGAGAAAGTTGTTGCAAACTGCCCAGAGACCCTGGGAGTCACTCCAGTTTTCTGAAACC
          >>>>>>>>>>>>>>>>>>>>

  61 CAGATATTTCAGtGCCTCAGGAGAGACAAGTCCTGACCTTCTCTCCTCCAGCTCTCCCAG

 121 gAGATAGGCAAGCCCCTAACTCCCTAACTAAGCCCTTACGACCTGAAATCCATTGAGTGG
       <<<<<<<<<<<<<<<<<<<<

 181 CTTCTTTAC
```

9th group

TABLE 2-continued

```
63) Whole sequence ::: rs2836550-rs2212596

CCCAGGAAGAGTGGAAAGATTAACCTTTGTGAGCCAAACCaGTGACACTTGATTACTTGA
CAGAACTAATCCTTCTGTCCTGATGACAGAAcTTCAACTACACAGGTACATGCAAGCTAA
TATCTGTTGTAA (SEQ ID NO: 179)

OLIGO start len tm gc % any http://frodo.wi.mit.edu/cgi-
bin/primer3/primer3_www_results_help.cgi - PRIMER_THREE 3' seq
(SEQ ID NOs: 180, 181)
LEFT PRIMER       1  21  59.56  47.62  3.00  2.00 CCCAGGAAGAGTGGAAAGATT
RIGHT PRIMER    120  21  56.03  42.66  6.00  1.00 TTAGCTTGCATGTACCTGTGT
SEQUENCE SIZE: 132
INCLUDED REGION SIZE: 132

PRODUCT SIZE: 120, PAIR ANY COMPL: 5.00, PAIR 3' COMPL: 3.00

   1 CCCAGGAAGAGTGGAAAGATTAACCTTTGTGAGCCAAACCaGTGACACTTGATTACTTGA
     >>>>>>>>>>>>>>>>>>>>

  61 CAGAACTAATCCTTCTGTCCTGATGACAGAAcTTCAACTACACAGGTACATGCAAGCTAA
                    <<<<<<<<<<<<<<<<<<<<

 121 TATCTGTTGTAA

64) Whole sequence ::: rs2836660-rs2836661

GCCTGGCAAGCTAGATGGGGTGAATTTTCACCTGCCACAGcCGCAAGTCAAAGCCACCGG
CTTCTCTCTTCTCCCTCCCATTGCTCCTGACAGCCAGGGTTAATATTTTGCCTCATGTAA
ACAGGGAGGCAtCCACCCGAGAATCTCCCCTCAGCCCACATAAGC (SEQ ID NO: 182)

OLIGO start len tm gc % any http://frodo.wi.mit.edu/cgi-
bin/primer3/primer3_www_results_help.cgi - PRIMER_THREE 3' seq
(SEQ ID NOs: 183, 184)
LEFT PRIMER       9  20  55.41  40.00  4.00  2.00 AGCTAGATGGGGTGAATTTT
RIGHT PRIMER    158  18  61.14  61.11  3.00  3.00 TGGGCTGAGGGGAGATTC
SEQUENCE SIZE: 165
INCLUDED REGION SIZE: 165

PRODUCT SIZE: 150, PAIR ANY COMPL: 4.00, PAIR 3' COMPL: 3.00

   1 GCCTGGCAAGCTAGATGGGGTGAATTTTCACCTGCCACAGcCGCAAGTCAAAGCCACCGG
        >>>>>>>>>>>>>>>>>>>>

  61 CTTCTCTCTTCTCCCTCCCATTGCTCCTGACAGCCAGGGTTAATATTTTGCCTCATGTAA

 121 ACAGGGAGGCAtCCACCCGAGAATCTCCCCTCAGCCCACATAAGC
           <<<<<<<<<<<<<<<<<<<<

65) Whole sequence ::: rs465612-rs8131220

atcaagctaattaatgttatctatcacttcAcatagttcaacctttttttgtggtgagag
tactgaagatctactctcttagcaattttcaaatctaaaatacattattattaacacagt
cactgtgccGtacgttagctctgaggaccttattcatttt (SEQ ID NO: 185)

OLIGO start len tm gc % any http://frodo.wi.mit.edu/cgi-
bin/primer3/primer3_www_results_help.cgi - PRIMER_THREE 3' seq
(SEQ ID NOs: 186, 187)
LEFT PRIMER       1  22  47.51  22.73  6.00  4.00 atcaagctaattaatgttatct
RIGHT PRIMER    155  20  50.92  40.00  5.00  5.00 aatgaataaggtcctcagag
SEQUENCE SIZE: 160
INCLUDED REGION SIZE: 160

PRODUCT SIZE: 156, PAIR ANY COMPL: 5.00, PAIR 3' COMPL: 2.00

   1 atcaagctaattaatgttatctatcacttcAcatagttcaacctttttttgtggtgagag
    >>>>>>>>>>>>>>>>>>>>

  61 tactgaagatctactctcttagcaattttcaaatctaaaatacattattattaacacagt

 121 cactgtgccGtacgttagctctgaggaccttattcatttt
              <<<<<<<<<<<<<<<<<<<<
```

TABLE 2-continued

66) Whole sequence ::: rs9980072-rs8130031

TTTAATCTGATCATTGCCCTATGAGGTAGGgAGTATTCTGATTCCCATTTTATAAATAAG
GAACCCGAGGCTTAGAGAGCATCaGTGACTTGTTCAAGGTCACCCACAGCTGTCAAGTGA
CAGA (SEQ ID NO: 188)

OLIGO start len tm gc % any http://frodo.wi.mit.edu/cgi-
bin/primer3/primer3_www_results_help.cgi - PRIMER_THREE 3' seq
(SEQ ID NOs: 189, 190)
LEFT PRIMER 1 21 55.02 33.33 6.00 2.00 TTTAATCTGATCATTGCCCTA
RIGHT PRIMER 111 18 57.61 55.56 5.00 1.00 AGCTGTGGGTGACCTTGA
SEQUENCE SIZE: 124
INCLUDED REGION SIZE: 124

PRODUCT SIZE: 111, PAIR ANY COMPL: 3.00, PAIR 3' COMPL: 1.00

1 TTTAATCTGATCATTGCCCTATGAGGTAGGgAGTATTCTGATTCCCATTTTATAAATAAG
>>>>>>>>>>>>>>>>>>>>

61 GAACCCGAGGCTTAGAGAGCATCaGTGACTTGTTCAAGGTCACCCACAGCTGTCAAGTGA
<<<<<<<<<<<<<<<<<<<<

121 CAGA

10$^{th}$ group

67) Whole sequence ::: rs416359-rs2836926 tgtcccaccattgtgtattaggtttgtagagCgtagacaacttgccttttttagtttgtag
gtttctgtatcaagagaagatgtgtgtGggcctaacctagattacaggatcctggacttc
aagtctga (SEQ ID NO: 191)

OLIGO start len tm gc % any http://frodo.wi.mit.edu/cgi-
bin/primer3/primer3_www_results_help.cgi - PRIMER_THREE 3' seq
(SEQ ID NOs: 192, 193)
LEFT PRIMER 1 20 54.64 40.00 6.00 3.00 tgtcccaccattgtgtatta
RIGHT PRIMER 128 20 54.70 45.00 9.00 3.00 tcagacttgaagtccaggat
SEQUENCE SIZE: 128
INCLUDED REGION SIZE: 128

PRODUCT SIZE: 128, PAIR ANY COMPL: 3.00, PAIR 3' COMPL: 1.00

1 tgtcccaccattgtgtattaggtttgtagagCgtagacaacttgccttttttagtttgtag
>>>>>>>>>>>>>>>>>>>>

61 gtttctgtatcaagagaagatgtgtgtGggcctaacctagattacaggatcctggacttc
<<<<<<<<<<<<

121 aagtctga
<<<<<<<<

68) Whole sequence ::: rs11701943-rs4815634 tcatttgctaaggtcggatagctcctaattggcaaagtcaCgatgggatcccagggattc
tgaggatgaagcctgtgtttaataactAttatgccaAGTGAGCATTTTCAAATATATGAG
AGAAATTA (SEQ ID NO: 194)

OLIGO start len tm gc % any http://frodo.wi.mit.edu/cgi-
bin/primer3/primer3_www_results_help.cgi - PRIMER_THREE 3' seq
(SEQ ID NOs: 195, 196)
LEFT PRIMER 2 19 53.86 42.11 4.00 2.00 catttgctaaggtcggata
RIGHT PRIMER 114 20 51.56 30.00 6.00 2.00 TATTTGAAAATGCTCACTtg
SEQUENCE SIZE: 128
INCLUDED REGION SIZE: 128

PRODUCT SIZE: 113, PAIR ANY COMPL: 6.00, PAIR 3' COMPL: 0.00

1 tcatttgctaaggtcggatagctcctaattggcaaagtcaCgatgggatcccagggattc
>>>>>>>>>>>>>>>>>>>>

61 tgaggatgaagcctgtgtttaataactAttatgccaAGTGAGCATTTTCAAATATATGAG
<<<<<<<<<<<<<<<<<<<<

121 AGAAATTA

TABLE 2-continued

```
69) Whole sequence ::: rs7278447-rs7278858

CATTGCTTCAGGGGTGTTAGTTTTGTGTTCaCAACTAGATTATAAACTCCTCTTGCATTC
CTGATGGCAGTGACTTGAAGGCAtttatttgaagaataatagacatacagaaaggggcac
atgtcataaaggtacagctggacgacttttcacaaagtg (SEQ ID NO: 197)

OLIGO start len tm gc % any http://frodo.wi.mit.edu/cgi-
bin/primer3/primer3_www_results_help.cgi - PRIMER_THREE 3' seq
(SEQ ID NOs: 198, 199)
LEFT PRIMER       5  20  55.96  45.00  2.00  0.00 GCTTCAGGGGTGTTAGTTTT
RIGHT PRIMER    157  20  55.97  45.00  5.00  1.00 ctttgtgaaaagtcgtccag
SEQUENCE SIZE: 159
INCLUDED REGION SIZE: 159

PRODUCT SIZE: 153, PAIR ANY COMPL: 4.00, PAIR 3' COMPL: 0.00

   1 CATTGCTTCAGGGGTGTTAGTTTTGTGTTCaCAACTAGATTATAAACTCCTCTTGCATTC
      >>>>>>>>>>>>>>>>>>>>

  61 CTGATGGCAGTGACTTGAAGGCAtttatttgaagaataatagacatacagaaaggggcac

 121 atgtcataaaggtacagctggacgacttttcacaaagtg
              <<<<<<<<<<<<<<<<<<<<

70) Whole sequence ::: rs385787-rs367001

GAGAGGATGGTGCCATCATGGAAAGCATGGGGCAGTCATGGAGATGACGGaGTAGCTCAT
GGAGAAgATAATGCCATCATGGAAGGCATAGTGCAGTCATGGAGATGATGGTGCAGC
(SEQ ID NO: 200)

OLIGO start len tm gc % any http://frodo.wi.mit.edu/cgi-
bin/primer3/primer3_www_results_help.cgi - PRIMER_THREE 3' seq
(SEQ ID NOs: 201, 202)
LEFT PRIMER      13  18  56.34  50.00  7.00  3.00 CCATCATGGAAAGCATGG
RIGHT PRIMER    108  20  55.09  45.00  4.00  2.00 TCATCTCCATGACTGCACTA
SEQUENCE SIZE: 117
INCLUDED REGION SIZE: 117

PRODUCT SIZE: 96, PAIR ANY COMPL: 7.00, PAIR 3' COMPL: 3.00

   1 GAGAGGATGGTGCCATCATGGAAAGCATGGGGCAGTCATGGAGATGACGGaGTAGCTCAT
          >>>>>>>>>>>>>>>>>>>>

  61 GGAGAAgATAATGCCATCATGGAAGGCATAGTGCAGTCATGGAGATGATGGTGCAGC
               <<<<<<<<<<<<<<<<<<<<

71) Whole sequence ::: rs367001-rs386095

ATGGGGCAGTCATGGAGATGACGGAGTAGCTCATGGAGAAaATAATGCCATCATGGAAGG
CATAGTGCAGTCATGGAGATGATGGTGCAGCTCATCCAGAAGATGGTGCCATCATGgAAG
GCATGGTGCAATCATGGAGTAGACAGTGCAGCTGGGCCaagattctc (SEQ ID NO: 203)

OLIGO start len tm gc % any http://frodo.wi.mit.edu/cgi-
bin/primer3/primer3_www_results_help.cgi - PRIMER_THREE 3' seq
(SEQ ID NOs: 204, 205)
LEFT PRIMER      15  20  54.39  50.00  4.00  3.00 GAGATGACGGAGTAGCTCAT
RIGHT PRIMER    156  18  55.17  61.11  6.00  2.00 CCCAGCTGCACTGTCTAC
SEQUENCE SIZE: 167
INCLUDED REGION SIZE: 167

PRODUCT SIZE: 142, PAIR ANY COMPL: 6.00, PAIR 3' COMPL: 2.00

   1 ATGGGGCAGTCATGGAGATGACGGAGTAGCTCATGGAGAAaATAATGCCATCATGGAAGG
          >>>>>>>>>>>>>>>>>>>>

  61 CATAGTGCAGTCATGGAGATGATGGTGCAGCTCATCCAGAAGATGGTGCCATCATGgAAG

 121 GCATGGTGCAATCATGGAGTAGACAGTGCAGCTGGGCCaagattctc
          <<<<<<<<<<<<<<<<<<<<
```

TABLE 2-continued

72) Whole sequence ::: rs2837296-rs2837297

GATGTGCCTCTCTTGTTCCAATCACAGGACAGGGGTATAAcTAGGGGCACTGTCTATACT
GGCTGCACTCTGGCCAGTGCTGTCCCAgGTAGATTCATCAGGGTCTAGAGCTTCAGCTAA
CAGCATGA (SEQ ID NO: 206)

OLIGO start len tm gc % any http://frodo.wi.mit.edu/cgi-bin/primer3/primer3_www_results_help.cgi - PRIMER_THREE 3' seq
(SEQ ID NOs: 207, 208)

```
LEFT PRIMER      11  20  56.00  45.00  4.00  1.00 TCTTGTTCCAATCACAGGAC
RIGHT PRIMER    126  20  54.59  45.00  6.00  3.00 ATGCTGTTAGCTGAAGCTCT
SEQUENCE SIZE: 128
INCLUDED REGION SIZE: 128

PRODUCT SIZE: 116, PAIR ANY COMPL: 4.00, PAIR 3' COMPL: 1.00

   1 GATGTGCCTCTCTTGTTCCAATCACAGGACAGGGGTATAAcTAGGGGCACTGTCTATACT
               >>>>>>>>>>>>>>>>>>>>

  61 GGCTGCACTCTGGCCAGTGCTGTCCCAgGTAGATTCATCAGGGTCTAGAGCTTCAGCTAA
                                                   <<<<<<<<<<<<<<

 121 CAGCATGA
     <<<<<<
```

73) Whole sequence ::: rs4239608-rs2410205

AGGGCCATGGGATGATGCAGGTGGAGACTGGAGTGCTACAGCTGCAAGCAAATACATTTCTGTGCT
GTGAAGCCAcCCATTTGGTGGTACTACGTTAAAACAGCTCTAGGAAATTAAtACAGATGTTGCCTGTAT
TTTTGTTTCTCATATTACTACTCATTGTTTTAATGATGACTGTTTTATT (SEQ ID NO: 355)

OLIGO start len tm gc % any http://frodo.wi.mit.edu/cgi-bin/primer3/primer3_www_results_help.cgi - PRIMER_THREE 3' seq
(SEQ ID NOs: 356, 357)

```
LEFT PRIMER      19  20  57.45  55.00  4.00  2.00 AGGTGGAGACTGGAGTGCTA
RIGHT PRIMER    145  22  56.58  31.82  2.00  0.00 AGAAACAAAAATACAGGCAACA
SEQUENCE SIZE: 184
INCLUDED REGION SIZE: 184

PRODUCT SIZE: 127, PAIR ANY COMPL: 3.00, PAIR 3' COMPL: 1.00

   1 AGGGCCATGGGATGATGCAGGTGGAGACTGGAGTGCTACAGCTGCAAGCAAATACATTTC
                       >>>>>>>>>>>>>>>>>>>>

  61 TGTGCTGTGAAGCCAcCCATTTGGTGGTACTACGTTAAAACAGCTCTAGGAAATTAAtAC

 121 AGATGTTGCCTGTATTTTTGTTTCTCATATTACTACTCATTGTTTTAATGATGACTGTTT
        <<<<<<<<<<<<<<<<<<<<<<

 181 TATT
```

74) Whole sequence ::: rs2837381-rs4816672

TTTTATTCATTAAGTTGAAAGCTCCTAAAGCAGAGGGACCaTATTTTTATGTCCCAACTC
TCCTTAAGgCCTTGCCTATGATAGCACATCTCTTCAATAGAATTGTCCT (SEQ ID NO: 209)

OLIGO start len tm gc % any http://frodo.wi.mit.edu/cgi-bin/primer3/primer3_www_results_help.cgi - PRIMER_THREE 3' seq
(SEQ ID NOs: 210, 211)

```
LEFT PRIMER      16  20  55.17  45.00  4.00  0.00 TGAAAGCTCCTAAAGCAGAG
RIGHT PRIMER     97  20  50.59  35.00  4.00  3.00 TTGAAGAGATGTGCTATCAT
SEQUENCE SIZE: 109
INCLUDED REGION SIZE: 109

PRODUCT SIZE: 82, PAIR ANY COMPL: 5.00, PAIR 3' COMPL: 1.00

   1 TTTTATTCATTAAGTTGAAAGCTCCTAAAGCAGAGGGACCaTATTTTTATGTCCCAACTC
                    >>>>>>>>>>>>>>>>>>>>

  61 TCCTTAAGgCCTTGCCTATGATAGCACATCTCTTCAATAGAATTGTCCT
                      <<<<<<<<<<<<<<<<<<<<
```

11 th group

TABLE 2-continued

75) Whole sequence ::: rs13047873-rs2637697

AAAGACCAGCTTTTAGCTGAACATCAGGGCTGCCTTCAGAGTTTAATTACCGCCCTCCCC
ATGGGGCCAAATGAGCCATCGACTCCTCCCAAGGGGGTTCgGCTTGGTACTGATCTTTAA
GTAAGTaAACGCTAAACCAGCTCATCTTAAAGCGCCCACATCTGATTTCCTGCTCTGCTG
CAAGACAGTAGGTGACTGGTAATGACC (SEQ ID NO: 214)

OLIGO start len tm gc % any http://frodo.wi.mit.edu/cgi-bin/primer3/primer3_www_results_help.cgi - PRIMER_THREE 3' seq
(SEQ ID NOs: 215, 216)
LEFT PRIMER 26 20 59.08 50.00 5.00 2.00 AGGGCTGCCTTCAGAGTTTA
RIGHT PRIMER 155 20 59.62 50.00 5.00 2.00 GCGCTTTAAGATGAGCTGGT
SEQUENCE SIZE: 207
INCLUDED REGION SIZE: 207

PRODUCT SIZE: 130, PAIR ANY COMPL: 3.00, PAIR 3' COMPL: 1.00

1 AAAGACCAGCTTTTAGCTGAACATCAGGGCTGCCTTCAGAGTTTAATTACCGCCCTCCCC
>>>>>>>>>>>>>>>>>>>>

61 ATGGGGCCAAATGAGCCATCGACTCCTCCCAAGGGGGTTCgGCTTGGTACTGATCTTTAA

121 GTAAGTaAACGCTAAACCAGCTCATCTTAAAGCGCCCACATCTGATTTCCTGCTCTGCTG
<<<<<<<<<<<<<<<<<<<<

181 CAAGACAGTAGGTGACTGGTAATGACC

76) Whole sequence ::: rs455999-rs9305700

ACTCTGCTCCCAGTGTGAACATGGGGAAAGTTGATTAAACTCTCTGACTTCAGATTCCTC
aTGTAAAATGTGGGGAAACAGCTCTGACTTAATGGTGTCACTGTGAGGAGTAAATGAGGT
AgCATATTTAAAGGATTTTGTATAGTGCTGGTGACAGTAACCAGCCAATAGATGATATAG
CTAGTAATAGCA (SEQ ID NO: 217)

OLIGO start len tm gc % any http://frodo.wi.mit.edu/cgi-bin/primer3/primer3_www_results_help.cgi - PRIMER_THREE 3' seq
(SEQ ID NOs: 218, 219)
LEFT PRIMER 16 20 57.84 40.00 4.00 2.00 TGAACATGGGGAAAGTTGAT
RIGHT PRIMER 154 22 56.51 40.91 4.00 0.00 TCACCAGCACTATACAAAATCC
SEQUENCE SIZE: 192
INCLUDED REGION SIZE: 192

PRODUCT SIZE: 139, PAIR ANY COMPL: 4.00, PAIR 3' COMPL: 2.00

1 ACTCTGCTCCCAGTGTGAACATGGGGAAAGTTGATTAAACTCTCTGACTTCAGATTCCTC
>>>>>>>>>>>>>>>>>>>>

61 aTGTAAAATGTGGGGAAACAGCTCTGACTTAATGGTGTCACTGTGAGGAGTAAATGAGGT

121 AgCATATTTAAAGGATTTTGTATAGTGCTGGTGACAGTAACCAGCCAATAGATGATATAG
<<<<<<<<<<<<<<<<<<<<

181 CTAGTAATAGCA

77) Whole sequence ::: rs9976207-rs455473 cttcactgaccacttccttaactgtccactccgaaacaccCcttcttcctgttcttccaa
tacaccaaactctttcttgcctctgtgtgcttgcccatgctgttccttctggcttcttcc
ttcACATTCAAGTCTTGACTTAGATGTCACTTGCCAAGGGAGACCTTGGA (SEQ ID NO: 220)

OLIGO start len tm gc % any http://frodo.wi.mit.edu/cgi-bin/primer3/primer3_www_results_help.cgi - PRIMER_THREE 3' seq
(SEQ ID NOs: 221, 222)
LEFT PRIMER 12 21 54.96 47.62 4.00 0.00 acttccttaactgtccactcc
RIGHT PRIMER 159 19 54.64 47.37 7.00 2.00 CCTTGGCAAGTGACATCTA
SEQUENCE SIZE: 170
INCLUDED REGION SIZE: 170

PRODUCT SIZE: 146, PAIR ANY COMPL: 5.00, PAIR 3' COMPL: 3.00

1 cttcactgaccacttccttaactgtccactccgaaacaccCcttcttcctgttcttccaa
>>>>>>>>>>>>>>>>>>>>

61 tacaccaaactctttcttgcctctgtgtgcttgcccatgctgttccttctggcttcttcc 121 ttcACATTCAAGTCTTGACTTAGATGTCACTTGCCAAGGGAGACCTTGGA
<<<<<<<<<<<<<<<<<<<<

TABLE 2-continued

```
78) Whole sequence ::: rs2837807-rs2637808

AAACATCCCAATAGACAAAACTCCAAGAAGAGTCAAAACAAGAATAAAGTaCAGGTCATC
TTTTCTTTTGCACTCCTGACAGCACTTTGTACATGGTAATAATAATCTACCAATTAACTA
CATAAGCCACATGGTTTTATcATAGTGTGAAGCTTTGTATCCAGAAAGGAGAGAAGGCTCC
(SEQ ID NO: 223)

OLIGO start len tm gc % any http://frodo.wi.mit.edu/cgi-
bin/primer3/primer3_www_results_help.cgi - PRIMER_THREE 3' seq
(SEQ ID NOs: 224, 225)
LEFT PRIMER      23  22  56.31  36.36  3.00  0.00 CCAAGAAGAGTCAAAACAAGAA
RIGHT PRIMER    172  21  56.19  42.86  4.00  2.00 TCTCCTTTCTGGATACAAAGC
SEQUENCE SIZE: 181
INCLUDED REGION SIZE: 181

PRODUCT SIZE: 150, PAIR ANY COMPL: 5.00, PAIR 3' COMPL: 1.00

   1 AAACATCCCAATAGACAAAACTCCAAGAAGAGTCAAAACAAGAATAAAGTaCAGGTCATC
                           >>>>>>>>>>>>>>>>>>>>>>

  61 TTTTCTTTTGCACTCCTGACAGCACTTTGTACATGGTAATAATAATCTACCAATTAACTA

 121 CATAAGCCACATGGTTTTATcATAGTGTGAAGCTTTGTATCCAGAAAGGAGAGAAGGCTC
                                    <<<<<<<<<<<<<<<<<<<<<

 181 C

79) Whole sequence ::: rs9974587-rs2776356

GGCAGAGGCATGGGGTGCATAGGGATATGGGGTGGGCCAGTTTGCTCCTCAGACCAGAAG
GGGTGCAGGAcTCCCCCCGATCAGGATCaTGGAGAAAGGTGTGGACAGAGGAAGGGAGGG
AGGGAGAAATGGCAGCTGCCCTGCAGTGG (SEQ ID NO: 226)

OLIGO start len tm gc % any http://frodo.wi.mit.edu/cgi-
bin/primer3/primer3_www_results_help.cgi - PRIMER_THREE 3' seq
(SEQ ID NOs: 227, 228)
LEFT PRIMER      42  20  60.52  55.00  3.00  2.00 TTGCTCCTCAGACCAGAAGG
RIGHT PRIMER    118  20  59.68  60.00  4.00  2.00 CTCCCTTCCTCTGTCCACAC
SEQUENCE SIZE: 149
INCLUDED REGION SIZE: 149

PRODUCT SIZE: 77, PAIR ANY COMPL: 5.00, PAIR 3' COMPL: 1.00

   1 GGCAGAGGCATGGGGTGCATAGGGATATGGGGTGGGCCAGTTTGCTCCTCAGACCAGAAG
                                              >>>>>>>>>>>>>>>>>>>

  61 GGGTGCAGGAcTCCCCCCGATCAGGATCaTGGAGAAAGGTGTGGACAGAGGAAGGGAGGG
     >                                     <<<<<<<<<<<<<<<<<<<<

 121 AGGGAGAAATGGCAGCTGCCCTGCAGTGG

80) Whole sequence ::: rs2838089-rs2838090

cagggactaagtgtctctgacaatacattcagccactactAcagtatgaagccagcccct
catccccaccttcagagacccctggtgcctcagattcctcggccattctggagctgctgt
gCCCGAGGCTTGTGTAGTTGGAGATCATTTTGGCAGTCAGTGCTG (SEQ ID NO: 229)

OLIGO start len tm gc % any http://frodo.wi.mit.edu/cgi-
bin/primer3/primer3_www_results_help.cgi - PRIMER_THREE 3' seq
(SEQ ID NOs: 230, 231)
LEFT PRIMER      12  22  55.48  40.91  5.00  2.00 tgtctctgacaatacattcagc
RIGHT PRIMER    160  20  55.81  45.00  4.00  2.00 CTGACTGCCAAAATGATCTC
SEQUENCE SIZE: 165
INCLUDED REGION SIZE: 165

PRODUCT SIZE: 149, PAIR ANY COMPL: 5.00, PAIR 3' COMPL: 1.00

   1 cagggactaagtgtctctgacaatacattcagccactactAcagtatgaagccagcccct
                >>>>>>>>>>>>>>>>>>>>>>

  61 catccccaccttcagagacccctggtgcctcagattcctcggccattctggagctgctgt

 121 gCCCGAGGCTTGTGTAGTTGGAGATCATTTTGGCAGTCAGTGCTG
                         <<<<<<<<<<<<<<<<<<<<

12th group
```

TABLE 2-continued

```
81) Whole sequence ::: rs453592-rs380152

CCTGTCTCCGTGCGTGAAAGCCGGCTCCAAAGTGCCTTCTGTCCTATCTGCCTTCcGCAC
CTGGCTTTCCTGAAAGAAAGAAAACGCGTGGCTTATCTTTTCACGGCACGCCACCTTCAC
TCTCaCTTTTTCTTTTCTAATAAATACCTCTGGATGGGTTAGTGGTAATCTCTCCTCAAAC
(SEQ ID NO: 232)

OLIGO start len tm gc % any http://frodo.wi.mit.edu/cgi-
bin/primer3/primer3_www_results_help.cgi - PRIMER_THREE 3' seq
(SEQ ID NOs: 233, 234)
LEFT PRIMER       24  20  60.00  55.00  4.00  1.00 GCTCCAAAGTGCCTTCTGTC
RIGHT PRIMER    165  20  58.87  55.00  3.00  2.00 CCACTAACCCATCCAGAGGT
SEQUENCE SIZE: 181
INCLUDED REGION SIZE: 181

PRODUCT SIZE: 142, PAIR ANY COMPL: 4.00, PAIR 3' COMPL: 1.00

   1 CCTGTCTCCGTGCGTGAAAGCCGGCTCCAAAGTGCCTTCTGTCCTATCTGCCTTCcGCAC
              >>>>>>>>>>>>>>>>>>>>

  61 CTGGCTTTCCTGAAAGAAAGAAAACGCGTGGCTTATCTTTTCACGGCACGCCACCTTCAC

 121 TCTCaCTTTTTCTTTTCTAATAAATACCTCTGGATGGGTTAGTGGTAATCTCTCCTCAAA
              <<<<<<<<<<<<<<<<<<<<

 181 C

82) Whole sequence ::: rs442723-rs449888

GGGAGCACAACCTAGGCCCCTCCTGGGGAGGTGGTGGAGTCAGAATCACGTAAGAGaCAA
AGTTCCAGTCCCTCAGTGCCGGCTCCATTGTCCCCTGGACTTCCCTTACAAACCACAGAT
GCAAAGAGAGCACTTCTCgGAATCTCCACACAGCCACGGTGGAGCACTCAACCCACGCGA
CCCTCGGGCGCAGGTGCT (SEQ ID NO: 235)

OLIGO start len tm gc % any http://frodo.wi.mit.edu/cgi-
bin/primer3/primer3_www_results_help.cgi - PRIMER_THREE 3' seq
(SEQ ID NOs: 236, 237)
LEFT PRIMER       23  20  65.82  65.00  3.00  1.00 CTGGGGAGGTGGTGGAGTCA
RIGHT PRIMER    169  20  66.12  65.00  7.00  1.00 GAGTGCTCCACCGTGGCTGT
SEQUENCE SIZE: 198
INCLUDED REGION SIZE: 198

PRODUCT SIZE: 147, PAIR ANY COMPL: 7.00, PAIR 3' COMPL: 1.00

   1 GGGAGCACAACCTAGGCCCCTCCTGGGGAGGTGGTGGAGTCAGAATCACGTAAGAGaCAA
             >>>>>>>>>>>>>>>>>>>>

  61 AGTTCCAGTCCCTCAGTGCCGGCTCCATTGTCCCCTGGACTTCCCTTACAAACCACAGAT

 121 GCAAAGAGAGCACTTCTCgGAATCTCCACACAGCCACGGTGGAGCACTCAACCCACGCGA
                <<<<<<<<<<<<<<<<<<<<

 181 CCCTCGGGCGCAGGTGCT

83) Whole sequence ::: rs375888-rs9976560

CCTGAGAAGCTTCCAGCAAAGCACCAGCACGAACCGCCCCACCTCCCCACCTCCCCGCCA
GCGTTGcCGGGACTGACAGATTACAGAGCTCTGgTCCCTCTGCACTCCTGCTCTGCCACC
CCCAGGGTGTCAGAATGTGCCCCCCACACAGTTTCCAAAAG (SEQ ID NO: 238)

OLIGO start len tm gc % any http://frodo.wi.mit.edu/cgi-
bin/primer3/primer3_www_results_help.cgi - PRIMER_THREE 3' seq
(SEQ ID NOs: 239, 240)
LEFT PRIMER       18  18  59.84  55.56  2.00  0.00 AAAGCACCAGCACGAACC
RIGHT PRIMER    143  18  59.89  61.11  3.00  3.00 GGGGCACATTCTGACACC
SEQUENCE SIZE: 161
INCLUDED REGION SIZE: 161

PRODUCT SIZE: 126, PAIR ANY COMPL: 3.00, PAIR 3' COMPL: 0.00

   1 CCTGAGAAGCTTCCAGCAAAGCACCAGCACGAACCGCCCCACCTCCCCACCTCCCCGCCA
           >>>>>>>>>>>>>>>>>>>>

  61 GCGTTGcCGGGACTGACAGATTACAGAGCTCTGgTCCCTCTGCACTCCTGCTCTGCCACC

 121 CCCAGGGTGTCAGAATGTGCCCCCCACACAGTTTCCAAAAG
       <<<<<<<<<<<<<<<<<<<<
```

TABLE 2-continued

```
84) Whole sequence ::: rs3819900-rs3819901

ATGGAGCTGCTGCGCCGGCCTGAGCTCTGATCCCTCCTCCGACCCAGCCTCACCCTGCaA
GCAGCACCATGTGGGGCTCAGAATGGGGATCTTAAGGGACCCTcCCCACAACCTCCCGAT
AAGCCTTTCCACGGAGGGCCCAAGCGGAGACAGGAGAACACT (SEQ ID NO: 241)

OLIGO start len tm gc % any http://frodo.wi.mit.edu/cgi-
bin/primer3/primer3_www_results_help.cgi - PRIMER_THREE 3' seq
(SEQ ID NOs: 242, 243)
LEFT PRIMER      20  19  57.00  57.89  6.00  0.00 CTGAGCTCTGATCCCTCCT
RIGHT PRIMER    158  18  57.51  55.56  2.00  0.00 TTCTCCTGTCTCCGCTTG
SEQUENCE SIZE: 162
INCLUDED REGION SIZE: 162

PRODUCT SIZE: 139, PAIR ANY COMPL: 3.00, PAIR 3' COMPL: 0.00

   1 ATGGAGCTGCTGCGCCGGCCTGAGCTCTGATCCCTCCTCCGACCCAGCCTCACCCTGCaA
            >>>>>>>>>>>>>>>>>>>>

  61 GCAGCACCATGTGGGGCTCAGAATGGGGATCTTAAGGGACCCTcCCCACAACCTCCCGAT

 121 AAGCCTTTCCACGGAGGGCCCAAGCGGAGACAGGAGAACACT
            <<<<<<<<<<<<<<<<<<<<

85) Whole sequence ::: rs10451852-rs1045183

ACTTTCAGAATGTGCTGCCTTCCACGTGTGAACCAGACTGAGCTCCTTTCTGCCACTGAT
GTTGAATTGTCCATTTGCTCACaTCAGTGTCCACGTGGCAAATCCACAGGGCgTGGGTGG
GATCCTGCAGTCTAGACAAAGCCAAGGAGCACCGCTGGAGGCCACGTTGGGCTTCCCAAT
CCACATGCAAACCC (SEQ ID NO: 244)

OLIGO start len tm gc % any http://frodo.wi.mit.edu/cgi-
bin/primer3/primer3_www_results_help.cgi - PRIMER_THREE 3' seq
(SEQ ID NOs: 245, 246)
LEFT PRIMER      45  20  59.29  50.00  3.00  1.00 CCTTCTGCCACTGATGTTG
RIGHT PRIMER    190  19  60.46  47.37  4.00  0.00 TTGCATGTGGATTGGGAAG
SEQUENCE SIZE: 194
INCLUDED REGION SIZE: 194

PRODUCT SIZE: 146, PAIR ANY COMPL: 4.00, PAIR 3' COMPL: 0.00

   1 ACTTTCAGAATGTGCTGCCTTCCACGTGTGAACCAGACTGAGCTCCTTTCTGCCACTGAT
                      >>>>>>>>>>>>>>>>

  61 GTTGAATTGTCCATTTGCTCACaTCAGTGTCCACGTGGCAAATCCACAGGGCgTGGGTGG
   >>>>

 121 GATCCTGCAGTCTAGACAAAGCCAAGGAGCACCGCTGGAGGCCACGTTGGGCTTCCCAAT
                        <<<<<<<<<

 181 CCACATGCAAACCC
   <<<<<<<<<<

86) Whole sequence ::: rs7278528-rs11701158

TCTCCAGCCAGCGTGTCACAAAGCCGCTCACCTGCTCGTGTGAGTGTCTGAATGCACGTG
TTTGAGTGTCAGaGGCGTGTGAACCACAGCAACTCAATCTTGAATAGGGGCTGGGTAAAG
TGAGGCTgAGACCTCCCGGGGCTGCATTCCCAGATGGTTAAGGCATTCTAAGTCACAAGA
TGAGTAGGAAGTTCGCACAAGACACTGGTCAT (SEQ ID NO: 247)

OLIGO start len tm gc % any http://frodo.wi.mit.edu/cgi-
bin/primer3/primer3_www_results_help.cgi - PRIMER_THREE 3' seq
(SEQ ID NOs: 248, 249)
LEFT PRIMER      28  20  60.53  55.00  4.00  0.00 TCACCTGCTCGTGTGAGTGT
RIGHT PRIMER    163  20  59.39  50.00  4.00  2.00 CCTTAACCATCTGGGAATGC
SEQUENCE SIZE: 213
INCLUDED REGION SIZE: 213

PRODUCT SIZE: 136, PAIR ANY COMPL: 3.00, PAIR 3' COMPL: 0.00

   1 TCTCCAGCCAGCGTGTCACAAAGCCGCTCACCTGCTCGTGTGAGTGTCTGAATGCACGTG
               >>>>>>>>>>>>>>>>>>>>

  61 TTTGAGTGTCAGaGGCGTGTGAACCACAGCAACTCAATCTTGAATAGGGGCTGGGTAAAG

 121 TGAGGCTgAGACCTCCCGGGGCTGCATTCCCAGATGGTTAAGGCATTCTAAGTCACAAGA
             <<<<<<<<<<<<<<<<<<<<
```

TABLE 2-continued

181 TGAGTAGGAAGTTCGCACAAGACACTGGTCAT

87) Whole sequence ::: rs2839627-rs170916

TTGAGTCCTCTTAAGTAGTTACTATAGTGGAGAACTTGAGTCATTCTTTGTAGCGTGCTT
cGTAGAGCAGCGTGTTTGTTAGAAGGATTTGTTAATCCTGTATAGgGTCTTTACGAAGGC
TGTTTTCATGGAAGCTTCTCTTTGTTGACTCC (SEQ ID NO: 250)

OLIGO start len tm gc % any http://frodo.wi.mit.edu/cgi-
bin/primer3/primer3_www_results_help.cgi - PRIMER_THREE 3' seq
(SEQ ID NOs: 251, 252)
LEFT PRIMER 28 22 55.68 36.36 5.00 1.00 TGGAGAACTTGAGTCATTCTTT
RIGHT PRIMER 152 19 52.33 47.37 3.00 2.00 GGAGTCAACAAAGAGAAGC
SEQUENCE SIZE: 152
INCLUDED REGION SIZE: 152

PRODUCT SIZE: 125, PAIR ANY COMPL: 5.00, PAIR 3' COMPL: 3.00

1 TTGAGTCCTCTTAAGTAGTTACTATAGTGGAGAACTTGAGTCATTCTTTGTAGCGTGCTT
>>>>>>>>>>>>>>>>>>>>

61 cGTAGAGCAGCGTGTTTGTTAGAAGGATTTGTTAATCCTGTATAGgGTCTTTACGAAGGC

121 TGTTTTCATGGAAGCTTCTCTTTGTTGACTCC
<<<<<<<<<<<<<<<<<<<<

88) Whole sequence ::: rs2839628-rs234740

CATTCTCTCCAGCTGCAAACTTTCTTCAACTTTCCTAAATTCTTAcTAAATTCAGAGGAA
TAGGATAAAGATCACTTAGAGAAAGGGTGCTTATGGACATAGCCTGAGTTTCCTTTAACC
TCTCTgCAATGGGTGCTTTTAACTAGCTTCTACATGGCAAGCTGTTTCAGTTTG
(SEQ ID NO: 253)

OLIGO start len tm gc % any http://frodo.wi.mit.edu/cgi-
bin/primer3/primer3_www_results_help.cgi - PRIMER_THREE 3' seq
(SEQ ID NOs: 254, 255)
LEFT PRIMER 20 21 50.06 28.57 3.00 2.00 CTTTCTTCAACTTTCCTAAAT
RIGHT PRIMER 160 19 50.96 42.11 4.00 2.00 TTGCCATGTAGAAGCTAGT
SEQUENCE SIZE: 174
INCLUDED REGION SIZE: 174

PRODUCT SIZE: 141, PAIR ANY COMPL: 5.00, PAIR 3' COMPL: 2.00,

1 CATTCTCTCCAGCTGCAAACTTTCTTCAACTTTCCTAAATTCTTAcTAAATTCAGAGGAA
>>>>>>>>>>>>>>>>>>>>

61 TAGGATAAAGATCACTTAGAGAAAGGGTGCTTATGGACATAGCCTGAGTTTCCTTTAACC

121 TCTCTgCAATGGGTGCTTTTAACTAGCTTCTACATGGCAAGCTGTTTCAGTTTG
<<<<<<<<<<<<<<<<<<<<

89) Whole sequence ::: rs2838239-rs2838240

GGACATCTGGAACTGCACCAGCACAGAACCGACACGTTGTTAcTCATCGTCACTCGGCAG
GGCTGAAGACCACCAGAACTCATGACAGGCAGACGTGCCTGGCCCAGTTGAGGATGTAGC
tTCAGAGCCAAGCGCCAGTCCTGTTGGCCACGTGGGCTGGGGGCAGGATAGACCA
(SEQ ID NO: 256)

OLIGO start len tm gc % any http://frodo.wi.mit.edu/cgi-
bin/primer3/primer3_www_results_help.cgi - PRIMER_THREE 3' seq
(SEQ ID NOs: 257, 258)
LEFT PRIMER 17 19 59.73 57.89 2.00 0.00 ACCAGCACAGAACCGACAC
RIGHT PRIMER 145 18 62.40 61.11 4.00 0.00 AACAGGACTGGCGCTTGG
SEQUENCE SIZE: 175
INCLUDED REGION SIZE: 175

PRODUCT SIZE: 129, PAIR ANY COMPL: 4.00, PAIR 3' COMPL: 1.00

1 GGACATCTGGAACTGCACCAGCACAGAACCGACACGTTGTTAcTCATCGTCACTCGGCAG
>>>>>>>>>>>>>>>>>>>>

61 GGCTGAAGACCACCAGAACTCATGACAGGCAGACGTGCCTGGCCCAGTTGAGGATGTAGC 121 tTCAGAGCCAAGCGCCAGTCCTGTTGGCCACGTGGGCTGGGGGCAGGATAGACCA
<<<<<<<<<<<<<<<<<<<<

TABLE 2-continued

90) Whole sequence ::: rs630397-rs11069106

GGCTGGTTCTGCCCTTGGGAGGTGGTTCCTTTGGCTGGACCAGAATGTCTGaAGATGATC
AGGAGAGGGCCAAGGGTTGGGGGGTGCCCCATGTGCACCCTGAGAATTGCACCAGGCACA
GtGAGCAACTTCAGCCCTCCTTGTGCAGAGCTGCAGCGTACAGTGCCAGCCCTCGCTGGC
CC (SEQ ID NO: 259)

OLIGO start len tm gc % any http://frodo.wi.mit.edu/cgi-bin/primer3/primer3_www_results_help.cgi - PRIMER_THREE 3' seq
(SEQ ID NOs: 260, 261)
LEFT PRIMER 14 20 61.79 55.00 3.00 0.00 CTTGGGAGGTGGTTCCTTTG
RIGHT PRIMER 148 16 61.15 51.11 4.00 1.00 CTGCACAAGGAGGGCTGA
SEQUENCE SIZE: 182
INCLUDED REGION SIZE: 182

PRODUCT SIZE: 135, PAIR ANY COMPL: 5.00, PAIR 3' COMPL: 0.00

1 GGCTGGTTCTGCCCTTGGGAGGTGGTTCCTTTGGCTGGACCAGAATGTCTGaAGATGATC
>>>>>>>>>>>>>>>>>>>>

61 AGGAGAGGGCCAAGGGTTGGGGGGTGCCCCATGTGCACCCTGAGAATTGCACCAGGCACA

121 GtGAGCAACTTCAGCCCTCCTTGTGCAGAGCTGCAGCGTACAGTGCCAGCCCTCGCTGGC
<<<<<<<<<<<<<<<<<<<<

181 CC

91) Whole sequence ::: rs9637180-rs481767

GTTCTCACTTTACTGAGAAACCTGGCAGCTTCTCAGGCCACCGCCCAGGTCACCTGCTCA
CCAGCAAcGTGAACCACAGGAACtGAGGCTGTGCGGGAGGCGGCTCTGCTCTGTGCTGGG
CCCCCCTCCTCCTCACTCACCCTCTTCAGTCACCCG (SEQ ID NO: 262)

OLIGO start len tm gc % any http://frodo.wi.mit.edu/cgi-bin/primer3/primer3_www_results_help.cgi - PRIMER_THREE 3' seq
(SEQ ID NOs: 263, 264)
LEFT PRIMER 11 20 57.70 50.00 5.00 5.00 TACTGAGAAACCTGGCAGCT
RIGHT PRIMER 155 20 54.98 50.00 3.00 0.00 CTTTGACTGAAGAGGGTGAG
SEQUENCE SIZE: 155
INCLUDED REGION SIZE: 155

PRODUCT SIZE: 145, PAIR ANY COMPL: 3.00, PAIR 3' COMPL: 2.00

1 GTTCTCACTTTACTGAGAAACCTGGCAGCTTCTCAGGCCACCGCCCAGGTCACCTGCTCA
>>>>>>>>>>>>>>>>>>>>

61 CCAGCAAcGTGAACCACAGGAACtGAGGCTGTGCGGGAGGCGGCTCTGCTCTGTGCTGGG

121 CCCCCCTCCTCCTCACTCACCCTCTTCAGTCACCCG
<<<<<<<<<<<<<<<<<<<<

92) Whole sequence ::: rs162360-rs162359

TTAGTATTATTATTTTCATATATATTTTTTATAATAATCATATATTCAATTTTATCATCA
AGAAAAAAGTTTTAAAATTCaAAATCCTTTCATGTGCACTGTTTTAAACTtAGGTAGAAG
AAAAAAAGTCACTGAAAATCCAAGATGTAATAAACAGGCCCAACAAAGGCCAACAAACTT
(SEQ ID NO: 265)

OLIGO start len tm gc % any http://frodo.wi.mit.edu/cgi-bin/primer3/primer3_www_results_help.cgi - PRIMER_THREE 3' seq
(SEQ ID NOs: 266, 267)
LEFT PRIMER 45 20 48.37 20.00 5.00 3.00 TTCAATTTTATCATCAAGAA
RIGHT PRIMER 163 20 55.18 40.00 4.00 1.00 TTGGGCCTGTTTATTACATC
SEQUENCE SIZE: 180
INCLUDED REGION SIZE: 180

PRODUCT SIZE: 119, PAIR ANY COMPL: 4.00, PAIR 3' COMPL: 1.00

1 TTAGTATTATTATTTTCATATATATTTTTTATAATAATCATATATTCAATTTTATCATCA
>>>>>>>>>>>>>>>>

61 AGAAAAAAGTTTTAAAATTCaAAATCCTTTCATGTGCACTGTTTTAAACTtAGGTAGAAG
>>>>

121 AAAAAAAGTCACTGAAAATCCAAGATGTAATAAACAGGCCCAACAAAGGCCAACAAACTT
<<<<<<<<<<<<<<<<<<<<

TABLE 2-continued

```
93) Whole sequence ::: rs162356-rs162355

AGGGAACATGGCCTTGCCCACACAGATTTCAGACATCTGGCTCCAGAACTGTGGGAGGAC
ACATTTCTGTTGTTTAGAACTGCaTGTTTTTTATACTTTGTTATGGCTGCCCTAGGcAAC
TAATACAGATATTATTTTCCACTTCTGAACTTAGCAAAATATTTTTAAAATGAAAATTCT
TAAATGTTGGCACAGT (SEQ ID NO: 268)

OLIGO start len tm gc % any http://frodo.wi.mit.edu/cgi-
bin/primer3/primer3_www_results_help.cgi - PRIMER_THREE 3' seq
(SEQ ID NOs: 269, 270)
LEFT PRIMER      14  20  60.24  45.00  3.00 3.00 TTGCCCACACAGATTTCAGA
RIGHT PRIMER    156  22  56.88  36.36  5.00 0.00 TGCTAAGTTCAGAAGTGGAAAA
SEQUENCE SIZE: 196
INCLUDED REGION SIZE: 196

PRODUCT SIZE: 143, PAIR ANY COMPL: 4.00, PAIR 3' COMPL: 2.00

   1 AGGGAACATGGCCTTGCCCACACAGATTTCAGACATCTGGCTCCAGAACTGTGGGAGGAC
         >>>>>>>>>>>>>>>>>>>>

  61 ACATTTCTGTTGTTTAGAACTGCaTGTTTTTTATACTTTGTTATGGCTGCCCTAGGcAAC

 121 TAATACAGATATTATTTTCCACTTCTGAACTTAGCAAAATATTTTTAAAATGAAAATTCT
         <<<<<<<<<<<<<<<<<<<<

 181 TAAATGTTGGCACAGT

94) Whole sequence ::: rs91424-rs463738

CTGGATAAAGGATGCTACACGTCCCTGGTGGGACAGAGCAGGACGGCAGGGGATTTCATT
AcGCCAcTCAGAATGGCAGGCAATTGAAAAAACTTATAAATTGTTTATTTCCAGAATTTT
(SEQ ID NO: 271)

OLIGO start len tm gc % any http://frodo.wi.mit.edu/cgi-
bin/primer3/primer3_www_results_help.cgi - PRIMER_THREE 3' seq
(SEQ ID NOs: 272, 273)
LEFT PRIMER       3  20  54.33  45.00  4.00 4.00 GGATAAAGGATGCTACACGT
RIGHT PRIMER    120  20  49.40  20.00  4.00 0.00 AAAATTCTGGAAATAAACAA
SEQUENCE SIZE: 120
INCLUDED REGION SIZE: 120

PRODUCT SIZE: 118, PAIR ANY COMPL: 3.00, PAIR 3' COMPL: 1.00

   1 CTGGATAAAGGATGCTACACGTCCCTGGTGGGACAGAGCAGGACGGCAGGGGATTTCATT
     >>>>>>>>>>>>>>>>>>>>

  61 AcGCCAcTCAGAATGGCAGGCAATTGAAAAAACTTATAAATTGTTTATTTCCAGAATTTT
                <<<<<<<<<<<<<<<<<<<<

95) Whole sequence ::: rs2838318-rs2838319

TGTCAGTGGTGTAATCCGACTGTGAAAGATCAGTCTAACAAAACAGCGGGGAGAGAGAGG
GCTGAATCAGAGCaACTAGGTCCAAAGCCGAGGGAACCACCAACAGATCCCCTGGTGACC
CAACAAGAAATGCTCCAGTCTGGACCCAgTCAGAGTCTGCAGGACACACGCAGACATTCT
GGAAGTTACAACAGCCAGGAGCAAGAGGACGCATGGCCTGACTG (SEQ ID NO: 274)

OLIGO start len tm gc % any http://frodo.wi.mit.edu/cgi-
bin/primer3/primer3_www_results_help.cgi - PRIMER_THREE 3' seq
(SEQ ID NOs: 275, 276)
LEFT PRIMER      49  20  60.30  60.00  3.00 3.00 GGGAGAGAGAGGGCTGAATC
RIGHT PRIMER    202  21  59.00  52.38  4.00 2.00 GCTCCTGGCTGTTGTAACTTC
SEQUENCE SIZE: 224
INCLUDED REGION SIZE: 224

PRODUCT SIZE: 154, PAIR ANY COMPL: 4.00, PAIR 3' COMPL: 1.00

   1 TGTCAGTGGTGTAATCCGACTGTGAAAGATCAGTCTAACAAAACAGCGGGGAGAGAGAGG
                             >>>>>>>>>>>>

  61 GCTGAATCAGAGCaACTAGGTCCAAAGCCGAGGGAACCACCAACAGATCCCCTGGTGACC
   >>>>>>>>

 121 CAACAAGAAATGCTCCAGTCTGGACCCAgTCAGAGTCTGCAGGACACACGCAGACATTCT

 181 GGAAGTTACAACAGCCAGGAGCAAGAGGACGCATGGCCTGACTG
   <<<<<<<<<<<<<<<<<<<<<
```

TABLE 2-continued

```
96) Whole sequence ::: rs915770-rs731935

CGCCAGAGCACCCCTTCTCAGAACAGAAAGCGTCTCTACAaAGTGATCCGGAAGTGAGTG
TGTGAGGGCGCTGCGTCCTCCCTGCTCCCCTTGGAGTTGCCCTTTCTTGCTCAGATCTGG
GTGCCTTgGCCTTGTCCTGGGCCCTTCCGCAGCCCCCGGGGTGATCCCCGCTAG (SEQ ID NO: 277)

OLIGO start len tm gc % any http://frodo.wi.mit.edu/cgi-
bin/primer3/primer3_www_results_help.cgi - PRIMER_THREE 3' seq
(SEQ ID NOs: 278, 279)
LEFT PRIMER       3  19  80.95  63.16  3.00 3.00 CCAGAGCACCCCTTCTCAG
RIGHT PRIMER    148  18  62.95  66.67  6.00 0.00 GGAAGGGCCCAGGACAAG
SEQUENCE SIZE: 174
INCLUDED REGION SIZE: 174

PRODUCT SIZE: 146, PAIR ANY COMPL: 6.00, PAIR 3' COMPL: 2.00

   1 CGCCAGAGCACCCCTTCTCAGAACAGAAAGCGTCTCTACAaAGTGATCCGGAAGTGAGTG
       >>>>>>>>>>>>>>>>>>>

  61 TGTGAGGGCGCTGCGTCCTCCCTGCTCCCCTTGGAGTTGCCCTTTCTTGCTCAGATCTGG

 121 GTGCCTTgGCCTTGTCCTGGGCCCTTCCGCAGCCCCCGGGGTGATCCCCGCTAG
               <<<<<<<<<<<<<<<<<<

Final Set

97) Whole sequence ::: rs1573338-rs1573339

TATCTTACGGATTTGTCAACATCATTTGAGAAGAAGTCCATAGGCTCAGCAGATTTTTAT
GCCAGGTGGGCCATGGCATAAAAATGTGAAGAATGTGCTCaCTTAGACAATACcTGTGCT
AAAATTGGAACAATACAGAGAAGATTAGCAAATTAAAACAATGTTAGGAAGTCAGTGTGG
TGAGGTACGGTGCCTCATGCC (SEQ ID NO: 280)

OLIGO start len tm gc % any http://frodo.wi.mit.edu/cgi-
bin/primer3/primer3_www_results_help.cgi - PRIMER_THREE 3' seq
(SEQ ID NOs: 281, 282)
LEFT PRIMER      47  21  59.24  42.86  3.00 1.00 CAGCAGATTTTTATGCCAGGT
RIGHT PRIMER    192  20  60.06  60.00  4.00 3.00 CACCGTACCTCACCACACTG
SEQUENCE SIZE: 201
INCLUDED REGION SIZE: 201

PRODUCT SIZE: 146, PAIR ANY COMPL: 4.00, PAIR 3' COMPL: 3.00

   1 TATCTTACGGATTTGTCAACATCATTTGAGAAGAAGTCCATAGGCTCAGCAGATTTTTAT
                                                   >>>>>>>>>>>>>>

  61 GCCAGGTGGGCCATGGCATAAAAATGTGAAGAATGTGCTCaCTTAGACAATACcTGTGCT
     >>>>>>>

 121 AAAATTGGAACAATACAGAGAAGATTAGCAAATTAAAACAATGTTAGGAAGTCAGTGTGG
                                                         <<<<<<<<

 181 TGAGGTACGGTGCCTCATGCC
     <<<<<<<<<<<<
```

TABLE 2-continued

98) Whole sequence ::: rs3788094-rs3788095

AGGCAGGGCCCTCCTTGCCACATGTAAAGCTGCACAGAGCGGTCACTATATGTGTTTCCA
TATTTGCAATCCAACCACCACCAACTGAGTGTGCGTCCTGaTCAGCCGAGCCTGCCCACG
GTGGCCACAGGCCCTCTACATTCTAATCTCGAGAGCCTGAGCATGTACAAATTAAACgAA
GCAAAACGACACCACCCAGTTCTGGCCGTACTATAGGAGGTTTCCAGGAAGGGTTTGTGA
ACATAAACATAAGCTAGGTAACACTCCTTTCTGAA (SEQ ID NO: 283)

OLIGO start len tm gc % any http://frodo.wi.mit.edu/cgi-bin/primer3/primer3_www_results_help.cgi - PRIMER_THREE 3' seq
(SEQ ID NOs: 284, 285)

| | | | | | | | |
|---|---|---|---|---|---|---|---|
| LEFT PRIMER | 73 | 20 | 57.88 | 50.00 | 5.00 | 3.00 | AACCACCACCAACTGAGTGT |
| RIGHR PRIMER | 220 | 20 | 56.94 | 55.00 | 6.00 | 2.00 | CCTCCTATAGTACGGCCAGA |

SEQUENCE SIZE: 275
INCLUDED REGION SIZE: 275

PRODUCT SIZE: 148, PAIR ANY COMPL: 3.00, PAIR 3' COMPL: 1.00

```
   1 AGGCAGGGCCCTCCTTGCCACATGTAAAGCTGCACAGAGCGGTCACTATATGTGTTTCCA

  61 TATTTGCAATCCAACCACCACCAACTGAGTGTGCGTCCTGaTCAGCCGAGCCTGCCCACG
             >>>>>>>>>>>>>>>>>>>>

 121 GTGGCCACAGGCCCTCTACATTCTAATCTCGAGAGCCTGAGCATGTACAAATTAAACgAA

 181 GCAAAACGACACCACCCAGTTCTGGCCGTACTATAGGAGGTTTCCAGGAAGGGTTTGTGA
               <<<<<<<<<<<<<<<<<<<<

 241 ACATAAACATAAGCTAGGTAACACTCCTTTCTGAA
```

99) Whole sequence ::: rs756554-rs756555

TCAGAGCATCGCCTCAGTGGCCATCAATAGCTCGGGGGACTGGATTGCTTTTGGCTGTTC
AGGTTTGTCCCCaGCCTGGGTGGTAGAGATGGACTCCCCATTAGGGACCAGTGCTGCCCG
GCTACAGGCtTACTTGACAGCCACCCACTGGGGGTGCCCTCCCCTCCCCCAGTTGTCCTC
CATGGGGTGCCCTCTCCCCCAGCCGCCTTTCAGAAGGGGCCCTCCCCTCC (SEQ ID NO: 286)

OLIGO start len tm gc % any http://frodo.wi.mit.edu/cgi-bin/primer3/primer3_www_results_help.cgi - PRIMER_THREE 3' seq
(SEQ ID NOs: 287, 288)

| | | | | | | | |
|---|---|---|---|---|---|---|---|
| LEFT PRIMER | 41 | 20 | 61.15 | 45.00 | 2.00 | 0.00 | TGGATTGCTTTTGGCTGTTC |
| RIGHT PRIMER | 189 | 20 | 61.37 | 55.00 | 6.00 | 2.00 | CACCCCATGGAAGACAACTG |

SEQUENCE SIZE: 230
INCLUDED REGION SIZE: 230

PRODUCT SIZE: 149, PAIR ANY COMPL: 4.00, PAIR 3' COMPL: 2.00

```
   1 TCAGAGCATCGCCTCAGTGGCCATCAATAGCTCGGGGGACTGGATTGCTTTTGGCTGTTC
                                            >>>>>>>>>>>>>>>>>>>>

  61 AGGTTTGTCCCCaGCCTGGGTGGTAGAGATGGACTCCCCATTAGGGACCAGTGCTGCCCG

 121 GCTACAGGCtTACTTGACAGCCACCCACTGGGGGTGCCCTCCCCTCCCCCAGTTGTCCTC
                                                            <<<<<<<<<<<

 181 CATGGGGTGCCCTCTCCCCCAGCCGCCTTTCAGAAGGGGCCCTCCCCTCC
     <<<<<<<<<
```

TABLE 2-continued

100) Whole sequence ::: rs4350841-rs2838545

CTCATGCTTACATCCTTAGCTGATCATTAAACTTTGTGACCATTTCATGCTCACTGCTTT
CTTGCCcGGGAGCTAATGGTGAGGAAAGGTCACTGGGAACCAGCGCACCAACCTCAGACA
TcGATTTTGTTCCAGCCTTTTTTCCTGGGCAGGGGTGGCTATCACCTGCTGGTAGGCAGC
GGCAGGCCCACTGTCCTGC (SEQ ID NO: 289)

OLIGO start len tm gc % any http://frodo.wi.mit.edu/cgi-bin/primer3/primer3_www_results_help.cgi - PRIMER_THREE 3' seq (SEQ ID NOs: 290, 291)

LEFT PRIMER 27 21 53.45 28.57 5.00 2.00 TTAAACTTTGTGACCATTTCA
RIGHT PRIMER 174 18 54.55 55.56 6.00 2.00 TACCAGCAGGTGATAGCC
SEQUENCE SIZE: 199
INCLUDED REGION SIZE: 199

PRODUCT SIZE: 148, PAIR ANY COMPL: 3.00, PAIR 3' COMPL: 0.00

1 CTCATGCTTACATCCTTAGCTGATCATTAAACTTTGTGACCATTTCATGCTCACTGCTTT
>>>>>>>>>>>>>>>>>>>>>

61 CTTGCCcGGGAGCTAATGGTGAGGAAAGGTCACTGGGAACCAGCGCACCAACCTCAGACA

121 TcGATTTTGTTCCAGCCTTTTTTCCTGGGCAGGGGTGGCTATCACCTGCTGGTAGGCAGC
<<<<<<<<<<<<<<<<<<

181 GGCAGGCCCACTGTCCTGC

101) Whole sequence ::: rs2838551-rs2838552

TGACAGAAAAGTCTCAGAGCAGTGCCTTCTGAGCTCTTCTACACCAAGCAGGCAGAATGT
TCACTGCTAATGAGgCTGGAGCTGGTCCCCAGCAGTGGTAGGAAGCTTCCAaCAGGCTCA
GGCTGTGGGTGCTTGCAGGGGCACAGTGTGACGGCCACGGGCCTCAGAGCTCTGGTGGGC
T (SEQ ID NO: 292)

OLIGO start len tm gc % any http://frodo.wi.mit.edu/cgi-bin/primer3/primer3_www_results_help.cgi - PRIMER_THREE 3' seq (SEQ ID NOs: 293, 294)

LEFT PRIMER 2 20 53.05 45.00 5.00 3.00 GACAGAAAAGTCTCAGAGCA
RIGHT PRIMER 135 18 62.10 61.11 5.00 3.00 CAAGCACCCACAGCCTGA
SEQUENCE SIZE: 181
INCLUDED REGION SIZE: 181

PRODUCT SIZE: 134, PAIR ANY COMPL: 4.00, PAIR 3' COMPL: 3.00

1 TGACAGAAAAGTCTCAGAGCAGTGCCTTCTGAGCTCTTCTACACCAAGCAGGCAGAATGT
>>>>>>>>>>>>>>>>>>>>

61 TCACTGCTAATGAGgCTGGAGCTGGTCCCCAGCAGTGGTAGGAAGCTTCCAaCAGGCTCA
<<<

121 GGCTGTGGGTGCTTGCAGGGGCACAGTGTGACGGCCACGGGCCTCAGAGCTCTGGTGGGC
<<<<<<<<<<<<<<<

181 T

TABLE 2-continued

```
102) Whole sequence ::: rs8134902-rs8133874

ACATCTTTCTCAAATAAAGATAACAGCGATGTATTTTCACAAAAGCAAGAGCTTAGAAAG
TACTcCACCCAGGTATCCCTCTTGGAAAAAATaCTTAAGGAAATATGACAAATGGCAAAG
TGATTGTTATGGATGGAATGTTTGTATCCTCCCAAAATTCACATGTTGAGACCCTAATTC
CAATATG (SEQ ID NO: 295)

OLIGO start len tm gc % any http://frodo.wi.mit.edu/cgi-
bin/primer3/primer3_www_results_help.cgi - PRIMER_THREE 3' seq
(SEQ ID NOs: 296, 297)
LEFT PRIMER      33  20  54.84  35.00  5.00  2.00 ATTTTCACAAAAGCAAGAGC
RIGHT PRIMER    155  20  54.97  40.00  3.00  0.00 TTGGGAGGATACAAACATTC
SEQUENCE SIZE: 187
INCLUDED REGION SIZE: 187

PRODUCT SIZE: 123, PAIR ANY COMPL: 4.00, PAIR 3' COMPL: 0.00

    1 ACATCTTTCTCAAATAAAGATAACAGCGATGTATTTTCACAAAAGCAAGAGCTTAGAAAG
                                      >>>>>>>>>>>>>>>>>>>>

   61 TACTcCACCCAGGTATCCCTCTTGGAAAAAATaCTTAAGGAAATATGACAAATGGCAAAG

  121 TGATTGTTATGGATGGAATGTTTGTATCCTCCCAAAATTCACATGTTGAGACCCTAATTC
                     <<<<<<<<<<<<<<<<<<<<

  181 CAATATG

103) Whole sequense ::: rs425667-rs382478

AGGGGCATTCTACAAAACACCCAACCGGTCAAGGTCGCTGAGGCCAAGGAGAGATTGGGC
AACCGTCACAAACCAGAGAAGcCGAGGAGAcCTTTCAGCCAACGCCATGTGGGGTCCTGA
GCAGGACCCACCGGAAGTTGGTGCAGCTGCCTAAAGACCGTCCTGGCTGAGAAGAAACAG
(SEQ ID NO: 298)

OLIGO start len tm gc % any http://frodo.wi.mit.edu/cgi-
bin/primer3/primer3_www_results_help.cgi - PRIMER_THREE 3' seq
(SEQ ID NOs: 299, 300)
LEFT PRIMER      46  18  55.06  50.00  4.00  2.00 AAGGAGAGATTGGGCAAC
RIGHT PRIMER    178  19  54.85  52.63  3.00  1.00 GTTTCTTCTCAGCCAGGAC
SEQUENCE SIZE: 180
INCLUDED REGION SIZE: 180

PRODUCT SIZE: 133, PAIR ANY COMPL: 4.00, PAIR 3' COMPL: 0.00

    1 AGGGGCATTCTACAAAACACCCAACCGGTCAAGGTCGCTGAGGCCAAGGAGAGATTGGGC
                                                   >>>>>>>>>>>>>>>

   61 AACCGTCACAAACCAGAGAAGcCGAGGAGAcCTTTCAGCCAACGCCATGTGGGGTCCTGA
      >>>

  121 GCAGGACCCACCGGAAGTTGGTGCAGCTGCCTAAAGACCGTCCTGGCTGAGAAGAAACAG
                                                 <<<<<<<<<<<<<<<<<<<

104) Whole sequence ::: rs2838650-rs2838651

TGGCCCTGACCTGCCAGAGCTGTTGGCCTCCAGCTGGCGGGTAAAACCCACGGCCTTCTC
AGAACAGGTTTCTCAACACATGAGACAGAACACACCAGACTTCCaAGGGGAACACCTGGA
TGGAGCTGGTTACCCAGATcGTTCAACACCGAGGGGCAGCGGCTTGAGGGTCTTTCCACG
AAGGCTGGATTAACAAGAGGAGCSRGGTCTCTCCAGGATGGGCCCA (SEQ ID NO: 301)

OLIGO start len tm gc % any http://frodo.wi.mit.edu/cgi-
bin/primer3/primer3_www_results_help.cgi - PRIMER_THREE 3' seq
(SEQ ID NOs: 302, 303)
LEFT PRIMER      79  20  54.89  50.00  4.00  1.00 CATGAGACAGAACACACCAG
RIGHT PRIMER    199  20  54.61  40.00  5.00  3.00 TCTTGTTAATCCAAGCCTTC
SEQUENCE SIZE: 228
INCLUDED REGION SIZE: 228

PRODUCT SIZE: 121, PAIR ANY COMPL: 4.00, PAIR 3' COMPL: 1.00

    1 TGGCCCTGACCTGCCAGAGCTGTTGGCCTCCAGCTGGCGGGTAAAACCCACGGCCTTCTC

   61 AGAACAGGTTTCTCAACACATGAGACAGAACACACCAGACTTCCaAGGGGAACACCTGGA
                        >>>>>>>>>>>>>>>>>>>>

  121 TGGAGCTGGTTACCCAGATcGTTCAACACCGAGGGGCAGCGGCTTGAGGGTCTTTCCACG
                                                                 <

  181 AAGGCTGGATTAACAAGAGGAGCSRGGTCTCTCCAGGATGGGCCCA
      <<<<<<<<<<<<<<<<<<<
```

TABLE 2-continued

```
105) Whole sequence ::: rs2838654-rs1296489

CCACCCAGTGTCACGTCACGGCCCCGGCACGCCATCCACGGACCCTGGATGGAGCCCAGC
TGCCTCCaGGAGCGCAGTTTAACTACAAAGGAGCCCTGGCTGCCCGCCCCGCCCAGACGC
ACTGACCTGTTGTTCTCTGTGGCTGCTGATGGCCCaTCCCCAACCACTGGTGACTCTTCC
CTGGGGCCCCAAGCTCAGCCCCTAACCCCCTGTTGCTGGAAGT (SEQ ID NO: 304)

OLIGO start len tm gc % any http://frodo.wi.mit.edu/cgi-
bin/primer3/primer3_www_results_help.cgi - PRIMER_THREE 3' seq
(SEQ ID NOs: 305, 306)
LEFT PRIMER      37  18  62.56  66.67  5.00  2.00 CACGGACCCTGGATGGAG
RIGHT PRIMER    183  18  53.14  55.56  3.00  2.00 CAGGGAAGAGTCACCAGT
SEQUENCE SIZE: 223
INCLUDED REGION SIZE: 223

PRODUCT SIZE: 147, PAIR ANY COMPL: 5.00, PAIR 3' COMPL: 2.00

   1 CCACCCAGTGTCACGTCACGGCCCCGGCACGCCATCCACGGACCCTGGATGGAGCCCAGC
                  >>>>>>>>>>>>>>>>>>>>

  61 TGCCTCCaGGAGCGCAGTTTAACTACAAAGGAGCCCTGGCTGCCCGCCCCGCCCAGACGC

 121 ACTGACCTGTTGTTCTCTGTGGCTGCTGATGGCCCaTCCCCAACCACTGGTGACTCTTCC
                    <<<<<<<<<<<<<<<<<

 181 CTGGGGCCCCAAGCTCAGCCCCTAACCCCCTGTTGCTGGAAGT
   <<<

106) Whole sequence ::: rs2838659-rs1108261

CAGAGGACTGGGCTGCGGGGTCAGGAATGGGCACACTTCCTAACTGCAGGACACTCTAAG
GGCTTTGGTCATGCACAGgCAGCCAAGAGAAGGTGTCGCTGaCACACAGCCTTCCAGGAG
CGGACTTGGAGACCTCGCCAAGGACCAGGACTCCCCAGCACTCACACTCCCTTAGGCGCT
GAAGTC (SEQ ID NO: 307)

OLIGO start len tm gc % any http://frodo.wi.mit.edu/cgi-
bin/primer3/primer3_www_results_help.cgi - PRIMER_THREE 3' seq
(SEQ ID NOs: 308, 309)
LEFT PRIMER      53  20  55.48  45.00  4.00  2.00 ACTCTAAGGGCTTTGGTCAT
RIGHT PRIMER    175  20  56.02  55.00  3.00  1.00 CTAAGGGAGTGTGAGTGCTG
SEQUENCE SIZE: 186
INCLUDED REGION SIZE: 186

PRODUCT SIZE: 123, PAIR ANY COMPL: 4.00, PAIR 3' COMPL: 1.00

   1 CAGAGGACTGGGCTGCGGGGTCAGGAATGGGCACACTTCCTAACTGCAGGACACTCTAAG
                        >>>>>>>>

  61 GGCTTTGGTCATGCACAGgCAGCCAAGAGAAGGTGTCGCTGaCACACAGCCTTCCAGGAG
   >>>>>>>>>>>>

 121 CGGACTTGGAGACCTCGCCAAGGACCAGGACTCCCCAGCACTCACACTCCCTTAGGCGCT
                  <<<<<<<<<<<<<<<<<<<<

 181 GAAGTC
```

TABLE 2-continued

```
107) Whole sequence ::: rs585597-rs585601

GAAGAGGACAACACGGGGCTGTCTGCAGAGCACCTGCCACGCGCCAGGCTCTGTGTCCAC
AAGCACGGCGGCTGCTCCCACATGACaGAGCTCGTGcGGCAGCTCCAGGACTGTCTGGTG
CCAGAGCCCCAGCTCTCCGCCAGCCCCAGGCCACTGTGCGAGGCCCTCAGTGAAGAGGGG
GCCGT (SEQ ID NO: 310)

OLIGO start len tm gc % any http://frodo.wi.mit.edu/cgi-
bin/primer3/primer3_www_results_help.cgi - PRIMER_THREE 3' seq
(SEQ ID NOs: 311, 312)
LEFT PRIMER      42  18  64.78  66.67  5.00  2.00 CGCCAGGCTCTGTGTCCA
RIGHT PRIMER    183  18  60.76  66.67  5.00  3.00 GGCCCCCTCTTCACTGAG
SEQUENCE SIZE: 185
INCLUDED REGION SIZE: 185

PRODUCT SIZE: 142, PAIR ANY COMPL: 5.00, PAIR 3' COMPL: 3.00

   1 GAAGAGGACAACACGGGGCTGTCTGCAGAGCACCTGCCACGCGCCAGGCTCTGTGTCCAC
                                              >>>>>>>>>>>>>>>>>>

  61 AAGCACGGCGGCTGCTCCCACATGACaGAGCTCGTGcGGCAGCTCCAGGACTGTCTGGTG

 121 CCAGAGCCCCAGCTCTCCGCCAGCCCCAGGCCACTGTGCGAGGCCCTCAGTGAAGAGGGG
                                                          <<<<<<<<<<<<<<<

 181 GCCGT
     <<<

108) Whole sequence ::: rs9981033-rs4818998

TCTAAATAATGTTAATGATCAAATTTAGTCAGATCTCAATCTTCATATGTTAGTTGCCTT
CTTAaTAAATATTCTGTTTTCTTTATCGTTCTTTATTTGTATCTCcACCTTCATTTCTGA
TTAAATTAAGAAGTTTTGTCTCTTCCATTTAATAATTAATGTATTTAATAACC
(SEQ ID NO: 313)

OLIGO start len tm gc % any http://frodo.wi.mit.edu/cgi-
bin/primer3/primer3_www_results_help.cgi - PRIMER_THREE 3' seq
(SEQ ID NOs: 314, 315)
LEFT PRIMER      24  22  51.86  31.82  6.00  2.00 TTTAGTCAGATCTCAATCTTCA
RIGHT PRIMER    149  22  54.02  31.82  4.00  3.00 AATGGAAGAGACAAAACTTCTT
SEQUENCE SIZE: 173
INCLUDED REGION SIZE: 173

PRODUCT SIZE: 126, PAIR ANY COMPL: 5.00, PAIR 3' COMPL: 1.00

   1 TCTAAATAATGTTAATGATCAAATTTAGTCAGATCTCAATCTTCATATGTTAGTTGCCTT
                            >>>>>>>>>>>>>>>>>>>>>>

  61 CTTAaTAAATATTCTGTTTTCTTTATCGTTCTTTATTTGTATCTCcACCTTCATTTCTGA

 121 TTAAATTAAGAAGTTTTGTCTCTTCCATTTAATAATTAATGTATTTAATAACC
            <<<<<<<<<<<<<<<<<<<<<<

109) Whole sequence ::: rs2838802-rs2838803

CACACTCCACACTGGCCCCACGCGGGTGGCGAAGGACTCAGCCAGAGCCTGGCAGGATCC
TGGGGTGTCTaTTTCCAAGGAATGTTCTGGAAGAAACATACACACATACTTGTTTGCCAG
ATTTACCTGTGTGGTcTTCCAGATGAGAAGCAGCCTGTGTCACTCCATAAGGGAGAGTGC
GTGCAGCATTGAGA (SEQ ID NO: 316)

OLIGO start len tm gc % any http://frodo.wi.mit.edu/cgi-
bin/primer3/primer3_www_results_help.cgi - PRIMER_THREE 3' seq
(SEQ ID NOs: 317, 318)
LEFT PRIMER      31  18  55.98  61.11  5.00  3.00 GAAGGACTCAGCCAGAGC
RIGHT PRIMER    177  20  55.20  50.00  7.00  3.00 CTCTCCCTTATGGAGTGACA
SEQUENCE SIZE: 194
INCLUDED REGION SIZE: 194

PRODUCT SIZE: 147, PAIR ANY COMPL: 4.00, PAIR 3' COMPL: 0.00

   1 CACACTCCACACTGGCCCCACGCGGGTGGCGAAGGACTCAGCCAGAGCCTGGCAGGATCC
                                   >>>>>>>>>>>>>>>>>>

  61 TGGGGTGTCTaTTTCCAAGGAATGTTCTGGAAGAAACATACACACATACTTGTTTGCCAG

 121 ATTTACCTGTGTGGTcTTCCAGATGAGAAGCAGCCTGTGTCACTCCATAAGGGAGAGTGC
                                                     <<<<<<<<<<<<<<<<<<<<

 181 GTGCAGCATTGAGA
```

TABLE 2-continued

110) Whole seqence ::: rs2183596-rs2150452

```
AAGAAACTCCCAAGGAACGCATTGTCCCAAGTTGCTGCACCAGTCAGTGTACATTCCCAC
AAaCAGTGCATGAGAGTTCCTGTTGCTTGTGAAATAAATGGTCAGCATTCAGTGTTGTCA
GCTTTTAAAATTTTCTCCTTTCTAGTGGGCATGTAATGGTcTCACATTATAGTTTTAATT
TGCATTTTCCTGGTGACATGTGATACGGAACCTTCCTCCCATGCT (SEQ ID NO: 319)

OLIGO start len tm gc % any http://frodo.wi.mit.edu/cgi-
bin/primer3/primer3_www_results_help.cgi - PRIMER_THREE 3' seq
(SEQ ID NOs: 320, 321)
LEFT PRIMER      39  19  50.19  47.37  6.00  2.00 ACCAGTCAGTGTACATTCC
RIGHT PRIMER    190  19  50.12  26.32  4.00  0.00 GGAAAATGCAAATTAAAAC
SEQUENCE SIZE: 225
INCLUDED REGION SIZE: 225

PRODUCT SIZE: 152, PAIR ANY COMPL: 4.00, PAIR 3' COMPL: 1.00

  1 AAGAAACTCCCAAGGAACGCATTGTCCCAAGTTGCTGCACCAGTCAGTGTACATTCCCAC
                                          >>>>>>>>>>>>>>>>>>>

 61 AAaCAGTGCATGAGAGTTCCTGTTGCTTGTGAAATAAATGGTCAGCATTCAGTGTTGTCA

121 GCTTTTAAAATTTTCTCCTTTCTAGTGGGCATGTAATGGTcTCACATTATAGTTTTAATT
                                                       <<<<<<<<<

181 TGCATTTTCCTGGTGACATGTGATACGGAACCTTCCTCCCATGCT
    <<<<<<<<<<
```

111) Whole sequence ::: rs4599218-rs9978646

```
GTGCAATTTAATTACAAACGCTTAAATGGGGAGGTCAGGGGCAGAGGGATGATGTCACAA
ACACACCCAcGTGTGCTTGGTGCAAAACAGTAAAACAAACAGCAAGAAGgTCCATGAAGG
AAAGATCGCCTCTGTCAGTGGGAGTAATGAGAGTGGCTGATGGACAGGTG
(SEQ ID NO: 322)

OLIGO start len tm gc % any http://frodo.wi.mit.edu/cgi-
bin/primer3/primer3_www_results_help.cgi - PRIMER_THREE 3' seq
(SEQ ID NOs: 323, 324)
LEFT PRIMER      19  20  61.86  55.00  4.00  1.00 CGCTTAAATGGGGAGGTCAG
RIGHT PRIMER    168  20  60.83  60.00  3.00  0.00 CCTGTCCATCAGCCACTCTC
SEQUENCE SIZE: 170
INCLUDED REGION SIZE: 170

PRODUCT SIZE: 150, PAIR ANY COMPL: 5.00, PAIR 3' COMPL: 2.00

  1 GTGCAATTTAATTACAAACGCTTAAATGGGGAGGTCAGGGGCAGAGGGATGATGTCACAA
                      >>>>>>>>>>>>>>>>>>>>

 61 ACACACCCAcGTGTGCTTGGTGCAAAACAGTAAAACAAACAGCAAGAAGgTCCATGAAGG

121 AAAGATCGCCTCTGTCAGTGGGAGTAATGAGAGTGGCTGATGGACAGGTG
                                <<<<<<<<<<<<<<<<<<<<
```

112) Whole sequence ::: rs11702503-rs3827270

```
ACGCCAAGCAGGAGATGCCAGACACAGAGTCCATCCTGAGAGAGTCTGTTCCTGTCCAAG
CTCAGAAACACAGGAAGCcACCTGTGCTGTAGCAGCACaCGGAGATGCATCCTTTCTGGT
CCACCCCACGGCCCTCATTGCAGTCAGGGATCCTCTCCCAGAAAGTCCCTGCTGCCAGCC
CCTGCCCTT (SEQ ID NO: 325)

OLIGO start len tm gc % any http://frodo.wi.mit.edu/cgi-
bin/primer3/primer3_www_results_help.cgi - PRIMER_THREE 3' seq
(SEQ ID NOs: 326, 327)
LEFT PRIMER       7  20  62.02  55.00  3.00  0.00 AGCAGGAGATGCCAGACACA
RIGHT PRIMER    125  20  63.37  55.00  5.00  4.00 GGTGGACCAGAAAGGATGCA
SEQUENCE SIZE: 189
INCLUDED REGION SIZE: 189

PRODUCT SIZE: 119, PAIR ANY COMPL: 3.00, PAIR 3' COMPL: 0.00

  1 ACGCCAAGCAGGAGATGCCAGACACAGAGTCCATCCTGAGAGAGTCTGTTCCTGTCCAAG
          >>>>>>>>>>>>>>>>>>>>

 61 CTCAGAAACACAGGAAGCcACCTGTGCTGTAGCAGCACaCGGAGATGCATCCTTTCTGGT
                                                 <<<<<<<<<<<<<<<

121 CCACCCCACGGCCCTCATTGCAGTCAGGGATCCTCTCCCAGAAAGTCCCTGCTGCCAGCC
    <<<<<

181 CCTGCCCTT
```

TABLE 2-continued

```
113) Whole sequence ::: rs2839084-rs9984302

CATGAGAAAGACTTTGTTCCCATGAGAACAACAAGAGAAACTCAAACAAAATTAAAATTG
TACTTTTCTAAAAGACcGGGGTGGGGGTCGTGGTCAGGCAGCaGCATGAAGAAAGCCTTG
AGAACTGAATTCCAGAAAGAAACAAGCATAGGCAAGAAAGAGAGATGACA
(SEQ ID NO: 328)

OLIGO start len tm gc % any http://frodo.wi.mit.edu/cgi-
bin/primer3/primer3_www_results_help.cgi - PRIMER_THREE 3' seq
(SEQ ID NOs: 329, 330)
LEFT PRIMER      19  22  59.21  40.91  4.00  0.00 CCCATGAGAACAACAAGAGAAA
RIGHT PRIMER    162  20  55.48  45.00  4.00  2.00 CTCTTTCTTGCCTATGCTTG
SEQUENCE SIZE: 170
INCLUDED REGION SIZE: 170

PRODUCT SIZE: 144, PAIR ANY COMPL: 5.00, PAIR 3' COMPL: 3.00

   1 CATGAGAAAGACTTTGTTCCCATGAGAACAACAAGAGAAACTCAAACAAAATTAAAATTG
            >>>>>>>>>>>>>>>>>>>>

  61 TACTTTTCTAAAAGACcGGGGTGGGGGTCGTGGTCAGGCAGCaGCATGAAGAAAGCCTTG

 121 AGAACTGAATTCCAGAAAGAAACAAGCATAGGCAAGAAAGAGAGATGACA
             <<<<<<<<<<<<<<<<<<<<

114) Whole sequence ::: rs2249057-rs2249060

AAGATTTAGAACAGCTGAAGCAGCGAGAAAAAACCCAGCATGAGTCaGAACTGGAGCAAC
TGAGGATTTATTTTGAAAAGAAGTTAAGGGATGCTGAGAAAACTTACCAAGAAGACCTAA
cCCTGTTACAGCAGAGGCTGCAGGGGGCGAGGGAAGATGCTCTTCTG
(SEQ ID NO: 331)

OLIGO start len tm gc % any http://frodo.wi.mit.edu/cgi-
bin/primer3/primer3_www_results_help.cgi - PRIMER_THREE 3' seq
(SEQ ID NOs: 332, 333)
LEFT PRIMER      12  21  63.07  47.62  6.00  0.00 CAGCTGAAGCAGCGAGAAAAA
RIGHT PRIMER    146  19  66.33  66.42  6.00  3.00 CCCCTGCAGCCTCTGCTGT
SEQUENCE SIZE: 167
INCLUDED REGION SIZE: 167

PRODUCT SIZE: 135, PAIR ANY COMPL: 7.00, PAIR 3' COMPL: 1.00

   1 AAGATTTAGAACAGCTGAAGCAGCGAGAAAAAACCCAGCATGAGTCaGAACTGGAGCAAC
         >>>>>>>>>>>>>>>>>>>>

  61 TGAGGATTTATTTTGAAAAGAAGTTAAGGGATGCTGAGAAAACTTACCAAGAAGACCTAA

 121 cCCTGTTACAGCAGAGGCTGCAGGGGGCGAGGGAAGATGCTCTTCTG
       <<<<<<<<<<<<<<<<<<<<

115) Whole sequence ::: rs2839226-rs2839227

GGGAAACTGACTTGGCTTTTGCAAGGGTCATTGCTTCCTGATGCATGTTTAACTGTCCTG
TGTTCACTTTGTTGCcGCAGGTTTTTAGAGGAACGTAAAGAGATCaCCGAGAAATTCAGT
GCGGAACAAGATGCCTTCCTGCAGGAGGCCCAGGAGCAGCATGCCCGTGAGCTG
(SEQ ID NO: 334)

OLIGO start len tm gc % any http://frodo.wi.mit.edu/cgi-
bin/primer3/primer3_www_results_help.cgi - PRIMER_THREE 3' seq
(SEQ ID NOs: 335, 336)
LEFT PRIMER       1  22  64.29  50.00  3.00  2.00 GGGAAACTGACTTGGCTTTTGC
RIGHT PRIMER    135  20  64.83  55.00  3.00  2.00 GGCATCTTGTTCCGCACTGA
SEQUENCE SIZE: 174
INCLUDED REGION SIZE: 174

PRODUCT SIZE: 135, PAIR ANY COMPL: 4.00, PAIR 3' COMPL: 0.00

   1 GGGAAACTGACTTGGCTTTTGCAAGGGTCATTGCTTCCTGATGCATGTTTAACTGTCCTG
     >>>>>>>>>>>>>>>>>>>>

  61 TGTTCACTTTGTTGCcGCAGGTTTTTAGAGGAACGTAAAGAGATCaCCGAGAAATTCAGT
                         <<<<<

 121 GCGGAACAAGATGCCTTCCTGCAGGAGGCCCAGGAGCAGCATGCCCGTGAGCTG
    <<<<<<<<<<<<<<<
```

TABLE 2-continued

```
116) Whole sequence ::: rs10854482-rs2839261

CCCTGCACACTGACCTGCATGCCCTCGTCACCTGCACTCTGCATGCTCACCATCTGACGG
ACTCCTGCGAcGGGCATGGGAAGGTCGCCGCCGCCGGCAGCCtTGCGAGCACTTTGGATG
TGTGCACCCGGCATGCCAGGCCCGAGTCAACAAGACTGGCCGACCTTGGCGTCCTG
(SEQ ID NO: 337)

OLIGO start len tm gc % any http://frodo.wi.mit.edu/cgi-
bin/primer3/primer3_www_results_help.cgi - PRIMER_THREE 3' seq
(SEQ ID NOs: 338, 339)
LEFT PRIMER      21  20  65.22  65.00  4.00  0.00 GCCCTCGTCACCTGCACTCT
RIGHT PRIMER    168  20  64.77  60.00  5.00  1.00 CCAAGGTCGGCCAGTCTGTT
SEQUENCE SIZE: 175
INCLUDED REGION SIZE: 175

PRODUCT SIZE: 148, PAIR ANY COMPL: 4.00, PAIR 3' COMPL: 0.00

   1 CCCTGCACACTGACCTGCATGCCCTCGTCACCTGCACTCTGCATGCTCACCATCTGACGG
                         >>>>>>>>>>>>>>>>>>>>

  61 ACTCCTGCGAcGGGCATGGGAAGGTCGCCGCCGCCGGCAGCCtTGCGAGCACTTTGGATG

 121 TGTGCACCCGGCATGCCAGGCCCGAGTCAACAAGACTGGCCGACCTTGGCGTCCTG
                                            <<<<<<<<<<<<<<<<<<<<

117) Whole sequence ::: rs2032111-rs718496

TTTATTGCTGAGTGGTATTCCATTTTATGGGTCCATTATAGTTTATTTGTCCAGACACTT
CATGGAAaGACATCAGTGTTTCCtGTTTTTCAATCATAAATTGATGTTTAATTTTAAAAT
TTTGGAATTGTAGAAGAAATGCAATTCTTTTTTCC (SEQ ID NO: 340)

OLIGO start len tm gc % any http://frodo.wi.mit.edu/cgi-
bin/primer3/primer3_www_results_help.cgi - PRIMER_THREE 3' seq
(SEQ ID NOs: 341, 342)
LEFT PRIMER      28  22  53.65  31.82  4.00  3.00 TGGGTCCATTATAGTTTATTTG
RIGHT PRIMER    143  22  57.46  31.82  4.00  2.00 TGCATTTCTTCTACAATTCCAA
SEQUENCE SIZE: 155
INCLUDED REGION SIZE: 155

PRODUCT SIZE: 116, PAIR ANY COMPL: 5.00, PAIR 3' COMPL: 3.00

   1 TTTATTGCTGAGTGGTATTCCATTTTATGGGTCCATTATAGTTTATTTGTCCAGACACTT
                                >>>>>>>>>>>>>>>>>>>>>>

  61 CATGGAAaGACATCAGTGTTTCCtGTTTTTCAATCATAAATTGATGTTTAATTTTAAAAT

 121 TTTGGAATTGTAGAAGAAATGCAATTCTTTTTTCC
   <<<<<<<<<<<<<<<<<<<<<<

118) Whole sequence ::: rs2070434-rs2070435

CTTTGGTGCAGAATCATGCTGCAGGCAAGGTGGGCCCACCTCCCTGGAATTTCATCCCCC
cCGTCAGTTAAACCCATGGTGGTTTTATTTTCTAGGCCACCTGATCTGGGAGGACCACCT
CCAAGAAAAGCAGTCCTaTCGATGAACGGTCTAAGTTATGGTGTTATCAGAGTGGATACT
GAAGAAAAGTTGTCAGTCCTTACTGTTC (SEQ ID NO: 343)

OLIGO start len tm gc % any http://frodo.wi.mit.edu/cgi-
bin/primer3/primer3_www_results_help.cgi - PRIMER_THREE 3' seq
(SEQ ID NOs: 344, 345)
LEFT PRIMER      33  20  66.57  60.00  4.00  3.00 GGCCCACCTCCCTGGAATTT
RIGHT PRIMER    176  22  54.26  40.91  4.00  0.00 TCCACTCTGATAACACCATAAC
SEQUENCE SIZE: 208
INCLUDED REGION SIZE: 208

PRODUCT SIZE: 144, PAIR ANY COMPL: 4.00, PAIR 3' COMPL: 1.00

   1 CTTTGGTGCAGAATCATGCTGCAGGCAAGGTGGGCCCACCTCCCTGGAATTTCATCCCCC
                                    >>>>>>>>>>>>>>>>>>>>

  61 cCGTCAGTTAAACCCATGGTGGTTTTATTTTCTAGGCCACCTGATCTGGGAGGACCACCT

 121 CCAAGAAAAGCAGTCCTaTCGATGAACGGTCTAAGTTATGGTGTTATCAGAGTGGATACT
                                    <<<<<<<<<<<<<<<<<<<<<<

 181 GAAGAAAAGTTGTCAGTCCTTACTGTTC
```

Example 6 Determining Whether a Fetus has Trisomy

The number of alleles and the relationship between the number of molecules for the alleles detected for a particular marker are used to determine whether a fetus has trisomy. The results of such an exemplary experiment are depicted in FIG. 3, which is an example of a constant denaturant capillary electrophoresis electropherogram output, where each peak represents the number of molecules of alleles for a marker detected in a sample. As will be appreciated, the marker can be any marker of interest where the maternal genome is heterozygous for that marker and the fetus inherits an allele from the father that is not present in the maternal genome. Although the following description is provided in terms of a single marker, it will be appreciated that in any of the methods described herein, multiple markers may be analyzed, and in some embodiments, multiple markers are analyzed simultaneously in a multiplexed reaction. In specific embodiments, the marker is a tandem SNP, and different alleles detected for this marker represent different haplotypes. In still further embodiments, the tandem SNP represents a short haplotype.

The upper panel of FIG. 3A illustrates the output that would result from a maternal buccal swab, which will comprise maternal nucleic acids but no fetal nucleic acids, In some embodiments, the maternal genome is heterozygous for a particular marker, and in such embodiments, two alleles will be detected in the maternal sample, and these alleles will be present in a 1:1 ratio, which is represented in the electropherogram output as two peaks of equal area.

The lower panel of FIG. 3A illustrates the output that would result from a sample from a baby with trisomy, where the sample comprises fetal nucleic acids but no maternal nucleic acids. The electropherogram output expected from such a sample would show three peaks with areas in a ratio of 1:1:1 or two peaks with areas in a ratio of 2:1. These ratios in the fetal sample result from the fact that a fetus with trisomy would have inherited a total of three alleles for a particular marker: two alleles from the mother and one from the father. If the maternal genome is heterozygous for the marker, three alleles would be detectable in the sample, and all three alleles would be present in the same numbers, resulting in a ratio of 1:1:1, as depicted in the first trace of the lower panel in FIG. 3A (labeled "Baby with trisomy"). If the maternal genome is homozygous for the marker, the fetus with trisomy would still have inherited two alleles from the mother and one from the father, but only two different alleles would be detected in the fetal sample, so only two peaks would be in the output. However, the number of molecules for each allele (represented by the area of the peak) would be different and the peaks would be in a 2:1 ratio, as shown in the last two traces of the lower panel in FIG. 3A. Although the term "peak" is discussed herein in terms of electropherogram output, it will be appreciated that the ratios and relationships described herein apply to the output of any modality that provides information on the number of molecular of an allele present in a sample.

Similar experiments can be conducted on a sample containing both maternal and fetal nucleic acids, and the ratio of the peaks (i.e., the number of molecules for the different alleles of a marker) can be used to determine whether a fetus has trisomy. FIG. 3B shows the electropherogram outputs expected from a sample containing both maternal and fetal nucleic acids, where the fetus has trisomy. In this illustrated example, the maternal genome is heterozygous for the marker, and the paternal genome has an allele that is not present in the maternal genome. The third peak (also referred to herein as the "paternal peak") in the fetal sample output represents the allele inherited from the father (also referred to herein as the "paternal allele"). In the example illustrated in this figure, the paternal allele is not present in the maternal genome. Thus, at informative markers, a sample containing both maternal and fetal nucleic acids will contain three alleles: the two from the maternal genome and the one inherited by the fetus from the paternal genome. The electropherogram output will show larger peaks for the two alleles in the maternal genome than for the allele from the paternal genome, because the sample contains molecules of the two alleles from the maternal genome and from the fetal genome (because the fetus inherited both alleles from the mother). The third peak for the paternal allele will be smaller, because the number of molecules for that allele are only contributed by the fetal nucleic acids in the sample—that allele is not present in the maternal genome, so the overall number of molecules for the paternal allele will be less than the number of molecules for the maternal alleles. The present inventors have found that in such a sample, the number of molecules for the different alleles of the marker will be in a specific ratio if a baby has trisomy. In one embodiment, the ratios will be evident as two equal peaks (the maternal peaks) and a third smaller (paternal) peak, that is, the ratio will be x:peak+x:peak+x (first trace of FIG. 3B), or the ratio will be x:peak:peak+2x, where x is the area of the smallest peak, which represents the number of molecules of the paternal allele, and peak, peak+x, and peak+2x represent the number of molecules of the maternal alleles (which will be the number of molecules of the alleles from the maternal nucleic acids and the number of molecules of the alleles from the fetal nucleic acids inherited from the mother). In a further embodiment, the ratio is about x:peak+x:peak+x or about x:peak:peak+2x if the baby has trisomy. In a still further embodiment, the ratio is approximately x:peak+x:peak+x or about x:peak:peak+2x if the baby has trisomy. As used herein, the term "approximately" encompasses any variation that can still be tolerated by statistical tests to separate the different ratios. Common tests for statistical significance include, among others, t-test, ANOVA, Kruskal-Wallis, Wilcoxon, Mann-Whitney and odds ratio. In some embodiments, approximate ratios mean that there is a variation in a range of ±10% to ±50%. As will be appreciated, such range in variation may include ranges including without limitation ±10% to ±45%, ±15% to ±40%, ±20% to ±35%, and ±25% to ±30%.

FIG. 3C shows the results expected if the fetus is normal (i.e., does not have trisomy). In the situation illustrated in FIG. 3C, the maternal genome is heterozygous for the marker and the fetal allele inherited from the father is not present in the maternal genome. Since the normal fetus will only have inherited one allele from the father and one allele from the mother, the three peaks would have different areas, but these areas would be in a different ratio to each other than would be seen for a fetus with trisomy. For a normal fetus, the areas will in one embodiment be in a ratio of peak:x:peak+x. As in FIG. 3B, "x" is the paternal peak and represents the number of molecules of the allele inherited by the fetus from the father, and "peak" and "peak+x" are the maternal peaks and represent the number of molecules of the alleles in the maternal genome and the number of molecules of the alleles in the fetal genome inherited from the mother. In a further embodiment, the areas will be in a ratio of about peak:x:peak+x. In a still further embodiment, the areas will be in ratio of approximately peak:x:peak+x. Since the fetus only inherited one allele from the mother, one of the maternal peaks would be larger than the other, and the larger peak would be larger by the number "x", because for the fetal nucleic acids in the sample, the number of molecules for the allele inherited from the father will be the same as the number of molecules for the allele inherited from the mother. The third paternal peak thus serves as an internal standard of the number of molecules for alleles present in the fetal genome, and the methods of the present invention do not require a comparison of measurements across different chromosomes. Detection of alleles for a marker on a single chromosome can be used to detect whether the fetus has a chromosomal abnormality. The third (paternal) peak serves as this internal sample whether the fetus has trisomy or not, because this third peak represents only the molecules of the allele the fetus inherited from the father. Since the paternal allele is not present in the maternal genome, the third peak is an internal standard that is independent of the overall concentration of fetal nucleic acids versus maternal nucleic acids in a particular sample.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method, said method comprising:

(a) providing a maternal plasma or serum sample comprising maternal and fetal cell free DNA and providing a maternal buccal sample comprising maternal DNA;

(b) synthesizing primers that flank tandem single nucleotide polymorphisms in a specific chromosomal region of interest, wherein the tandem single nucleotide polymorphisms are single nucleotide polymorphisms that are at most 250 nucleotides apart;

(c) amplifying loci in the specific chromosomal region of interest in the maternal and fetal cell free DNA in the maternal plasma or serum sample using the synthesized primers to produce amplicons and amplifying loci in the specific chromosomal region of interest in the maternal DNA in the maternal buccal sample using the synthesized primers to produce amplicons; and (d) sequencing the amplicons produced in the maternal plasma or serum sample and the amplicons produced in the maternal buccal sample to identify and quantify the amplicons in the maternal plasma or serum sample and in the maternal buccal sample, wherein the amplicons in the maternal serum or plasma sample comprise at least three different haplotypes of the tandem single nucleotide polymorphisms, and wherein at least one of the haplotypes is not present in the maternal buccal sample and thereby is not present in the maternal genome.

2. The method of claim 1, wherein the single nucleotide polymorphisms in the tandem single nucleotide polymorphism are at most 100 nucleotides apart.

3. The method of claim 1, wherein the single nucleotide polymorphisms in the tandem single nucleotide polymorphism are at most 75 nucleotides apart.

4. The method of claim 1, wherein the single nucleotide polymorphisms in the tandem single nucleotide polymorphism are at most 50 nucleotides apart.

5. The method of claim 1, wherein the method comprises using constant denaturant capillary electrophoresis and high-fidelity PCR.

6. The method of claim 1, wherein the method comprises using denaturing HPLC, denaturing capillary electrophoresis, cycling temperature capillary electrophoresis, allele-specific PCR, quantitative PCR, or combinations thereof.

7. The method of claim 1, wherein the loci comprise at least one of the nucleic acid sequences selected from the group consisting of SEQ ID NO: 1-357.

* * * * *

SEQUENCE LISTING

```
<160> NUMBER OF SEQ ID NOS: 357

<210> SEQ ID NO 1
<211> LENGTH: 127
<212> TYPE: DNA
<213> ORGANISM: Homo sapiens

<400> SEQUENCE: 1

aacaaatctt catcttggaa tagcctgtga gaatgcctaa tcatctacga atgttacttt      60

ggcaccatct actggacaga ttaaataaca accaactcac tgtggattag acctacttct     120

atttcag                                                               127


<210> SEQ ID NO 2
<211> LENGTH: 20
<212> TYPE: DNA
<213> ORGANISM: Homo sapiens

<400> SEQUENCE: 2

atagcctgtg agaatgccta                                                  20


<210> SEQ ID NO 3
<211> LENGTH: 20
<212> TYPE: DNA
<213> ORGANISM: Homo sapiens

<400> SEQUENCE: 3

atccacagtg agttggttgt                                                  20
```

<210> SEQ ID NO 4
<211> LENGTH: 84
<212> TYPE: DNA
<213> ORGANISM: Homo sapiens

<400> SEQUENCE: 4
ttcctggaaa acaaaagtat ttctttcata gcccagctag catgataaat cagcgagtca 60
gaattctagc tttgttgtaa ggtt 84

<210> SEQ ID NO 5
<211> LENGTH: 20
<212> TYPE: DNA
<213> ORGANISM: Homo sapiens

<400> SEQUENCE: 5
tcctggaaaa caaaagtatt 20

<210> SEQ ID NO 6
<211> LENGTH: 21
<212> TYPE: DNA
<213> ORGANISM: Homo sapiens

<400> SEQUENCE: 6
aaccttacaa caaagctaga a 21

<210> SEQ ID NO 7
<211> LENGTH: 71
<212> TYPE: DNA
<213> ORGANISM: Homo sapiens

<400> SEQUENCE: 7
cactaagcct tggggatcca gctgcttaag gactaagacc gtatctagct ccttttagta 60
tttccacagc a 71

<210> SEQ ID NO 8
<211> LENGTH: 20
<212> TYPE: DNA
<213> ORGANISM: Homo sapiens

<400> SEQUENCE: 8
actaagcctt ggggatccag 20

<210> SEQ ID NO 9
<211> LENGTH: 21
<212> TYPE: DNA
<213> ORGANISM: Homo sapiens

<400> SEQUENCE: 9
tgctgtggaa atactaaaag g 21

<210> SEQ ID NO 10
<211> LENGTH: 155
<212> TYPE: DNA
<213> ORGANISM: Homo sapiens

<400> SEQUENCE: 10
tcctccagag gtaatcctgt gatcagcact aacaccacat accagccctt tcatcagctt 60
gttggagaag catctttact tcccgccaag cagtgaccta gataccatct cacaccagtt 120
agaatcagga tcattaaaaa gtcaagaaaa aacag 155

-continued

<210> SEQ ID NO 11
<211> LENGTH: 20
<212> TYPE: DNA
<213> ORGANISM: Homo sapiens

<400> SEQUENCE: 11
ctccagaggt aatcctgtga 20

<210> SEQ ID NO 12
<211> LENGTH: 21
<212> TYPE: DNA
<213> ORGANISM: Homo sapiens

<400> SEQUENCE: 12
tggtgtgaga tggtatctag g 21

<210> SEQ ID NO 13
<211> LENGTH: 146
<212> TYPE: DNA
<213> ORGANISM: Homo sapiens

<400> SEQUENCE: 13
tccaagtata atccatgaat cttgtttaaa tatagatcaa ataaaccact ataccaaaaa 60
catcaaaaga caactgggta aattttttaa atgactagct atttgatgtt aaggaagtaa 120
tgttactctc ttatatacaa tttgaa 146

<210> SEQ ID NO 14
<211> LENGTH: 22
<212> TYPE: DNA
<213> ORGANISM: Homo sapiens

<400> SEQUENCE: 14
gtataatcca tgaatcttgt tt 22

<210> SEQ ID NO 15
<211> LENGTH: 22
<212> TYPE: DNA
<213> ORGANISM: Homo sapiens

<400> SEQUENCE: 15
ttcaaattgt atataagaga gt 22

<210> SEQ ID NO 16
<211> LENGTH: 132
<212> TYPE: DNA
<213> ORGANISM: Homo sapiens

<400> SEQUENCE: 16
atggaaccga aacttcaagt agtttcatac gtatcacatt gacagttttc tctaagtttt 60
ctggtcttat gactcgttgt ttcattatta aaactgtgcc agtgtatgca tagggcttag 120
aaatttttta at 132

<210> SEQ ID NO 17
<211> LENGTH: 18
<212> TYPE: DNA
<213> ORGANISM: Homo sapiens

<400> SEQUENCE: 17
atggaaccga aacttcaa 18

<210> SEQ ID NO 18
<211> LENGTH: 22
<212> TYPE: DNA
<213> ORGANISM: Homo sapiens

<400> SEQUENCE: 18
ttaataatga aacaacgagt ca 22

<210> SEQ ID NO 19
<211> LENGTH: 157
<212> TYPE: DNA
<213> ORGANISM: Homo sapiens

<400> SEQUENCE: 19
acaggatcct tcctgaagac accaccttgg ggagggtgaa ggataaagaa tttgatcaga 60
aatcaagggt ggtgagatac atgttaagga tgaataaact ggccttttag gattcttgct 120
aaaattagac aatgcagagg caaccacaga gtccaag 157

<210> SEQ ID NO 20
<211> LENGTH: 19
<212> TYPE: DNA
<213> ORGANISM: Homo sapiens

<400> SEQUENCE: 20
ttcctgaaga caccacctt 19

<210> SEQ ID NO 21
<211> LENGTH: 18
<212> TYPE: DNA
<213> ORGANISM: Homo sapiens

<400> SEQUENCE: 21
cttggactct gtggttgc 18

<210> SEQ ID NO 22
<211> LENGTH: 173
<212> TYPE: DNA
<213> ORGANISM: Homo sapiens

<400> SEQUENCE: 22
aatttccatt aaatcttgtt cgttgcttta ctgaggcact gaagttacca atgttccact 60
ggttgacctg cggggctatc tctaggttat gttactccag aaaatgaatt gtgtataaaa 120
gaggccttgg aggaaggcgt tttattcaca tcagttgttt tgcacattgc tta 173

<210> SEQ ID NO 23
<211> LENGTH: 20
<212> TYPE: DNA
<213> ORGANISM: Homo sapiens

<400> SEQUENCE: 23
actgaggcac tgaagttacc 20

<210> SEQ ID NO 24
<211> LENGTH: 20
<212> TYPE: DNA
<213> ORGANISM: Homo sapiens

<400> SEQUENCE: 24
taagcaatgt gcaaaacaac 20

-continued

<210> SEQ ID NO 25
<211> LENGTH: 191
<212> TYPE: DNA
<213> ORGANISM: Homo sapiens

<400> SEQUENCE: 25
tcggtttcag caggaaagtt atttttaata acttccctgt atttcttggt ttcagttatt 60
aattaactca ttaatgctaa actttgtgat cctaggttaa aaaacatatt caagatagct 120
tcagaatgtt tggtatacaa gtaggtctgg ctaaatataa gtgttagctt tctcaagcat 180
ctaaatgctg g 191

<210> SEQ ID NO 26
<211> LENGTH: 20
<212> TYPE: DNA
<213> ORGANISM: Homo sapiens

<400> SEQUENCE: 26
gcaggaaagt tatttttaat 20

<210> SEQ ID NO 27
<211> LENGTH: 21
<212> TYPE: DNA
<213> ORGANISM: Homo sapiens

<400> SEQUENCE: 27
tgcttgagaa agctaacact t 21

<210> SEQ ID NO 28
<211> LENGTH: 166
<212> TYPE: DNA
<213> ORGANISM: Homo sapiens

<400> SEQUENCE: 28
aagttatttt taataacttc cctgtatttc ttggtttcag ttattaatta actcattaat 60
gctaaacttt gtgatcctag gttaaaaaac atattcaaga tagcttcaga atgtttggta 120
tacaagtagg tctggctaaa tataagtgtt agctttctca agcatc 166

<210> SEQ ID NO 29
<211> LENGTH: 20
<212> TYPE: DNA
<213> ORGANISM: Homo sapiens

<400> SEQUENCE: 29
atttttaata acttccctgt 20

<210> SEQ ID NO 30
<211> LENGTH: 20
<212> TYPE: DNA
<213> ORGANISM: Homo sapiens

<400> SEQUENCE: 30
cacttatatt tagccagacc 20

<210> SEQ ID NO 31
<211> LENGTH: 152
<212> TYPE: DNA
<213> ORGANISM: Homo sapiens

<400> SEQUENCE: 31
attcattgtg tagaaagtgc ctgactcagt gtttggaaat tgtctgactt ttcctcatat 60
atagtgtggt ttcatgttat tgtatataag aactgacatg aactctgttt acaataatct 120
cccagtgcca taaagaccat aataaataat at 152

<210> SEQ ID NO 32
<211> LENGTH: 20
<212> TYPE: DNA
<213> ORGANISM: Homo sapiens

<400> SEQUENCE: 32
cagtgtttgg aaattgtctg 20

<210> SEQ ID NO 33
<211> LENGTH: 20
<212> TYPE: DNA
<213> ORGANISM: Homo sapiens

<400> SEQUENCE: 33
ggcactggga gattattgta 20

<210> SEQ ID NO 34
<211> LENGTH: 163
<212> TYPE: DNA
<213> ORGANISM: Homo sapiens

<400> SEQUENCE: 34
cactgggtcc tgttgttaag tacacataat accacacagg agaaaatcag gctaattgta 60
aatgggcaac ctacttaatt gtttcattaa aaagcataca gattacattt acactatagc 120
tagtcttgtt tgttttttta ttttgcaaaa gtaattacgg ccc 163

<210> SEQ ID NO 35
<211> LENGTH: 20
<212> TYPE: DNA
<213> ORGANISM: Homo sapiens

<400> SEQUENCE: 35
tcctgttgtt aagtacacat 20

<210> SEQ ID NO 36
<211> LENGTH: 18
<212> TYPE: DNA
<213> ORGANISM: Homo sapiens

<400> SEQUENCE: 36
gggccgtaat tacttttg 18

<210> SEQ ID NO 37
<211> LENGTH: 108
<212> TYPE: DNA
<213> ORGANISM: Homo sapiens

<400> SEQUENCE: 37
ctactcagta ggcactttgt gtctagaaac ttctgtgtca acggttttcc ctctctctgg 60
aattcatcag gacagaagtg attggtgtgg tggaagaggg ttgtgsta 108

<210> SEQ ID NO 38
<211> LENGTH: 21
<212> TYPE: DNA
<213> ORGANISM: Homo sapiens

<400> SEQUENCE: 38
actcagtagg cactttgtgt c 21

<210> SEQ ID NO 39
<211> LENGTH: 18
<212> TYPE: DNA
<213> ORGANISM: Homo sapiens

<400> SEQUENCE: 39
tcttccacca caccaatc 18

<210> SEQ ID NO 40
<211> LENGTH: 144
<212> TYPE: DNA
<213> ORGANISM: Homo sapiens

<400> SEQUENCE: 40
tggcttttca aaggtaaaat ttactaagtg tattaatatt ttaccaattt ccagccagga 60
gagtatgaat gttgcattat tacattgctt tgaaacaaag cattagtctt aattcagaag 120
tttaaattca gatgttaacg ttgc 144

<210> SEQ ID NO 41
<211> LENGTH: 19
<212> TYPE: DNA
<213> ORGANISM: Homo sapiens

<400> SEQUENCE: 41
tggcttttca aaggtaaaa 19

<210> SEQ ID NO 42
<211> LENGTH: 21
<212> TYPE: DNA
<213> ORGANISM: Homo sapiens

<400> SEQUENCE: 42
gcaacgttaa catctgaatt t 21

<210> SEQ ID NO 43
<211> LENGTH: 110
<212> TYPE: DNA
<213> ORGANISM: Homo sapiens

<400> SEQUENCE: 43
taagtattga agaaaggaga atttaaatta cttcatatac ctgataaagg aaaacatata 60
caaggcaaat aaacatctta gatcatgaca tataaaataa tagattatta 110

<210> SEQ ID NO 44
<211> LENGTH: 20
<212> TYPE: DNA
<213> ORGANISM: Homo sapiens

<400> SEQUENCE: 44
ttgaagaaag gagaatttaa 20

<210> SEQ ID NO 45
<211> LENGTH: 22
<212> TYPE: DNA
<213> ORGANISM: Homo sapiens

<400> SEQUENCE: 45
attttatatg tcatgatcta ag 22

-continued

<210> SEQ ID NO 46
<211> LENGTH: 165
<212> TYPE: DNA
<213> ORGANISM: Homo sapiens

<400> SEQUENCE: 46
tgcagagatt acaggtgtga gccaccgtgc ccagcctcat aaccgtttca actacttttt 60
cacttgacaa gcagatgtga agttaacaaa gtcacccata tttgaaataa agatagtata 120
ttcctggggt aggcagaggc agttgaggat catgaaataa ctatg 165

<210> SEQ ID NO 47
<211> LENGTH: 19
<212> TYPE: DNA
<213> ORGANISM: Homo sapiens

<400> SEQUENCE: 47
agagattaca ggtgtgagc 19

<210> SEQ ID NO 48
<211> LENGTH: 19
<212> TYPE: DNA
<213> ORGANISM: Homo sapiens

<400> SEQUENCE: 48
atgatcctca actgcctct 19

<210> SEQ ID NO 49
<211> LENGTH: 178
<212> TYPE: DNA
<213> ORGANISM: Homo sapiens

<400> SEQUENCE: 49
tgcaatgaaa ctcaaaagag aaaagttaac aggtgcaaaa ggtagtttta ttataaaagg 60
agggtaggca acaagaatat gtttaatttt tcttcctttt catgagtaag gacaagagtg 120
tcatatatgt gaatattttt atttaatttt aagtagaaat ctgtttttaa aatatggg 178

<210> SEQ ID NO 50
<211> LENGTH: 20
<212> TYPE: DNA
<213> ORGANISM: Homo sapiens

<400> SEQUENCE: 50
tgaaactcaa aagagaaaag 20

<210> SEQ ID NO 51
<211> LENGTH: 20
<212> TYPE: DNA
<213> ORGANISM: Homo sapiens

<400> SEQUENCE: 51
acagatttct acttaaaatt 20

<210> SEQ ID NO 52
<211> LENGTH: 102
<212> TYPE: DNA
<213> ORGANISM: Homo sapiens

<400> SEQUENCE: 52
ccaccattca tcaaaacttt gatactggac tcaattgtga atttgacttg aaatttgata 60
atgcttttgt tttactgttc tgctcagcaa aatagtacat gt 102

<210> SEQ ID NO 53
<211> LENGTH: 20
<212> TYPE: DNA
<213> ORGANISM: Homo sapiens

<400> SEQUENCE: 53
caaaactttg atactggact 20

<210> SEQ ID NO 54
<211> LENGTH: 19
<212> TYPE: DNA
<213> ORGANISM: Homo sapiens

<400> SEQUENCE: 54
acatgtacta ttttgctga 19

<210> SEQ ID NO 55
<211> LENGTH: 166
<212> TYPE: DNA
<213> ORGANISM: Homo sapiens

<400> SEQUENCE: 55
gcctgcataa agtgaggatg gtgtagtaat tgggtatctc cagttataaa cacaaaaagc 60
atgatagagc tgggactgtg attgcaggaa agcaatagtc actccaaaag gagatcctca 120
tgatatgaat acggaagaaa caatatttcc tgctaatgta gtagcc 166

<210> SEQ ID NO 56
<211> LENGTH: 20
<212> TYPE: DNA
<213> ORGANISM: Homo sapiens

<400> SEQUENCE: 56
cctgcataaa gtgaggatgg 20

<210> SEQ ID NO 57
<211> LENGTH: 21
<212> TYPE: DNA
<213> ORGANISM: Homo sapiens

<400> SEQUENCE: 57
tgaggatctc cttttggagt g 21

<210> SEQ ID NO 58
<211> LENGTH: 154
<212> TYPE: DNA
<213> ORGANISM: Homo sapiens

<400> SEQUENCE: 58
gcaaaggggt actctatgta atgaacatga cctggcagta ctgacatctc ctgagggact 60
gttagaagtg cagactcttg tatcttttct caagtctatg aaatctagac ttcattttaa 120
caagatgacc cgatatttac atacacatta aagt 154

<210> SEQ ID NO 59
<211> LENGTH: 20
<212> TYPE: DNA
<213> ORGANISM: Homo sapiens

<400> SEQUENCE: 59
gcaaaggggt actctatgta 20

<210> SEQ ID NO 60
<211> LENGTH: 20
<212> TYPE: DNA
<213> ORGANISM: Homo sapiens

<400> SEQUENCE: 60
tatcgggtca tcttgttaaa 20

<210> SEQ ID NO 61
<211> LENGTH: 174
<212> TYPE: DNA
<213> ORGANISM: Homo sapiens

<400> SEQUENCE: 61
gtatctaaca aagctctgtc caaaattttg aatttctcgt taaaagcatc atgattatag 60
aacagaggtt acaatcaatt attcagtcac acaatcactc tcatcagtca ttaaggtgcg 120
tacctggtgt tccagttatt cagtgtggta taacaaacta cctggaactt aatg 174

<210> SEQ ID NO 62
<211> LENGTH: 22
<212> TYPE: DNA
<213> ORGANISM: Homo sapiens

<400> SEQUENCE: 62
tctaacaaag ctctgtccaa aa 22

<210> SEQ ID NO 63
<211> LENGTH: 21
<212> TYPE: DNA
<213> ORGANISM: Homo sapiens

<400> SEQUENCE: 63
ccacactgaa taactggaac a 21

<210> SEQ ID NO 64
<211> LENGTH: 202
<212> TYPE: DNA
<213> ORGANISM: Homo sapiens

<400> SEQUENCE: 64
agagtggtta agtgacttga tcaattcctc aggtggggat tcaagctctt aaagctgtag 60
actatgtcgt ccaaacaaac actgacatga atatgacttc caataggcaa gaaaagaggc 120
ctaggtcgag atactgcaag acatgcaagc aatctagtaa tggcataaaa cctgctatcc 180
gaattggcta aaattatgta tt 202

<210> SEQ ID NO 65
<211> LENGTH: 20
<212> TYPE: DNA
<213> ORGANISM: Homo sapiens

<400> SEQUENCE: 65
ggtggggatt caagctctta 20

<210> SEQ ID NO 66
<211> LENGTH: 22
<212> TYPE: DNA
<213> ORGANISM: Homo sapiens

<400> SEQUENCE: 66
ggatagcagg ttttatgcca tt 22

<210> SEQ ID NO 67
<211> LENGTH: 156
<212> TYPE: DNA
<213> ORGANISM: Homo sapiens

<400> SEQUENCE: 67
ttctttctca cacaatgggt tccattccca ctactactcc attcaaattg aagtgccttc 60
aatgattatt aaaaaactct ctttaaaata gctcacgtaa ccttacatcc tttgactgag 120
gctcaactca tgtcaatgct tcagtatcaa cttttc 156

<210> SEQ ID NO 68
<211> LENGTH: 21
<212> TYPE: DNA
<213> ORGANISM: Homo sapiens

<400> SEQUENCE: 68
aatgggttcc attcccacta c 21

<210> SEQ ID NO 69
<211> LENGTH: 20
<212> TYPE: DNA
<213> ORGANISM: Homo sapiens

<400> SEQUENCE: 69
tgagcctcag tcaaaggatg 20

<210> SEQ ID NO 70
<211> LENGTH: 202
<212> TYPE: DNA
<213> ORGANISM: Homo sapiens

<400> SEQUENCE: 70
atttgtaata acatttagta agtatttatt tgaggagttt gaattttgtt cttgtttatc 60
ttgttctctt tcttcgtaga ttagttggtg ttaacatcaa taggataacc ctttctttca 120
gcatatgtga atgaaataaa ccaattattg ccactttcca ggttaaccag aatatacata 180
gatacgagga cagtggactg tt 202

<210> SEQ ID NO 71
<211> LENGTH: 22
<212> TYPE: DNA
<213> ORGANISM: Homo sapiens

<400> SEQUENCE: 71
ttgaggagtt tgaattttgt tc 22

<210> SEQ ID NO 72
<211> LENGTH: 20
<212> TYPE: DNA
<213> ORGANISM: Homo sapiens

<400> SEQUENCE: 72
aacctggaaa gtggcaataa 20

<210> SEQ ID NO 73
<211> LENGTH: 171
<212> TYPE: DNA
<213> ORGANISM: Homo sapiens

<400> SEQUENCE: 73
tagggcagag agagcaagca agctctctac cttctcatat aagggcacta atcccaccat 60

-continued gaaggcgcca ctgtcatgac ctgattatgt cacaaagacc ccggggcaaa tattaccact 120
gtgaggagta cagttttagc atgtgaattt tggaagaaca caaacattta g 171

<210> SEQ ID NO 74
<211> LENGTH: 21
<212> TYPE: DNA
<213> ORGANISM: Homo sapiens

<400> SEQUENCE: 74
gcaagcaagc tctctacctt c 21

<210> SEQ ID NO 75
<211> LENGTH: 22
<212> TYPE: DNA
<213> ORGANISM: Homo sapiens

<400> SEQUENCE: 75
tgttcttcca aaattcacat gc 22

<210> SEQ ID NO 76
<211> LENGTH: 195
<212> TYPE: DNA
<213> ORGANISM: Homo sapiens

<400> SEQUENCE: 76
attctaattt taaatatcat tgatgtagaa cattctattt cactattcct tcattttatt 60
attatgggaa attatataca gttctccaga tttttaaagc cttgctaaca tgttttaagt 120
cacacaaata ttctcctgtg ggaaaatgac agtaatttag tgtgcaacaa ttatatagaa 180
ctatttttca aactt 195

<210> SEQ ID NO 77
<211> LENGTH: 21
<212> TYPE: DNA
<213> ORGANISM: Homo sapiens

<400> SEQUENCE: 77
atttcactat tccttcattt t 21

<210> SEQ ID NO 78
<211> LENGTH: 22
<212> TYPE: DNA
<213> ORGANISM: Homo sapiens

<400> SEQUENCE: 78
taattgttgc acactaaatt ac 22

<210> SEQ ID NO 79
<211> LENGTH: 138
<212> TYPE: DNA
<213> ORGANISM: Homo sapiens

<400> SEQUENCE: 79
actgtcatgg acttaaacaa ttgtctttga attgtctttt ttcatacttt tatttgcatc 60
tttccactaa aaagatggca caaagtaatc ctagtttaca ttttttacca tgtaattcca 120
tattactttt tcctgaaa 138

<210> SEQ ID NO 80
<211> LENGTH: 20
<212> TYPE: DNA

<213> ORGANISM: Homo sapiens

<400> SEQUENCE: 80
actgtcatgg acttaaacaa 20

<210> SEQ ID NO 81
<211> LENGTH: 22
<212> TYPE: DNA
<213> ORGANISM: Homo sapiens

<400> SEQUENCE: 81
ttcaggaaaa agtaatatgg aa 22

<210> SEQ ID NO 82
<211> LENGTH: 119
<212> TYPE: DNA
<213> ORGANISM: Homo sapiens

<400> SEQUENCE: 82
aaagaaaaaa aagccacaga aatcagtcct agagaaaacc gatctatgag ctgcctgaaa 60
ataattataa aataactatc ataaaaatgc ccagtgagat ataagaaaac acagacaac 119

<210> SEQ ID NO 83
<211> LENGTH: 21
<212> TYPE: DNA
<213> ORGANISM: Homo sapiens

<400> SEQUENCE: 83
aaaaagccac agaaatcagt c 21

<210> SEQ ID NO 84
<211> LENGTH: 22
<212> TYPE: DNA
<213> ORGANISM: Homo sapiens

<400> SEQUENCE: 84
ttcttatatc tcactgggca tt 22

<210> SEQ ID NO 85
<211> LENGTH: 143
<212> TYPE: DNA
<213> ORGANISM: Homo sapiens

<400> SEQUENCE: 85
caaggtcaga gaagttatct tggatggtag aagagaagaa aggagaagaa aggataagca 60
gaaaatcaaa aagggcataa aaaaattact ggggaaaata attcttagtc actcaccatt 120
tcttatgttt gtgaaaacag aaa 143

<210> SEQ ID NO 86
<211> LENGTH: 22
<212> TYPE: DNA
<213> ORGANISM: Homo sapiens

<400> SEQUENCE: 86
ggatggtaga agagaagaaa gg 22

<210> SEQ ID NO 87
<211> LENGTH: 22
<212> TYPE: DNA
<213> ORGANISM: Homo sapiens

<400> SEQUENCE: 87
tcacaaacat aagaaatggt ga 22

<210> SEQ ID NO 88
<211> LENGTH: 136
<212> TYPE: DNA
<213> ORGANISM: Homo sapiens

<400> SEQUENCE: 88
gaccacaatt cacaaatgca aagatgcaga accaacctaa gtggccactg actaatgaga 60
ggataaagaa gatgtggcat atatatatca gggactacta ctcagccatt acaaggaaca 120
aaataatgtc ttttgc 136

<210> SEQ ID NO 89
<211> LENGTH: 20
<212> TYPE: DNA
<213> ORGANISM: Homo sapiens

<400> SEQUENCE: 89
tgcaaagatg cagaaccaac 20

<210> SEQ ID NO 90
<211> LENGTH: 22
<212> TYPE: DNA
<213> ORGANISM: Homo sapiens

<400> SEQUENCE: 90
ttttgttcct tgtaatggct ga 22

<210> SEQ ID NO 91
<211> LENGTH: 160
<212> TYPE: DNA
<213> ORGANISM: Homo sapiens

<400> SEQUENCE: 91
gaccacaatt cacaaatgca aagatgcaga accaacctaa gtggccactg actaatgaga 60
ggataaagaa gatgtggcat atatacatca gggactactt ctcagccatt acaaggaaca 120
aaataatgtc ttttgcaaca acttggatag agctggaggc 160

<210> SEQ ID NO 92
<211> LENGTH: 20
<212> TYPE: DNA
<213> ORGANISM: Homo sapiens

<400> SEQUENCE: 92
tgcaaagatg cagaaccaac 20

<210> SEQ ID NO 93
<211> LENGTH: 21
<212> TYPE: DNA
<213> ORGANISM: Homo sapiens

<400> SEQUENCE: 93
gcctccagct ctatccaagt t 21

<210> SEQ ID NO 94
<211> LENGTH: 160
<212> TYPE: DNA
<213> ORGANISM: Homo sapiens

<400> SEQUENCE: 94

-continued

```
aatcctagac cttggattgc aagagactcc ttaatatctt cccatgtcca catttccttc     60

acatagtttg aatgtggctt ctattatata cagatacaag attcaaatcc aacctctatg    120

atgactggtc ttgtgaataa gcagaagagg cactaacaat                          160


<210> SEQ ID NO 95
<211> LENGTH: 22
<212> TYPE: DNA
<213> ORGANISM: Homo sapiens

<400> SEQUENCE: 95

ccttaatatc ttcccatgtc ca                                              22


<210> SEQ ID NO 96
<211> LENGTH: 22
<212> TYPE: DNA
<213> ORGANISM: Homo sapiens

<400> SEQUENCE: 96

attgttagtg cctcttctgc tt                                              22


<210> SEQ ID NO 97
<211> LENGTH: 162
<212> TYPE: DNA
<213> ORGANISM: Homo sapiens

<400> SEQUENCE: 97

aagagaagtg aggtcagcag ctgcaagcca cctccgtcat ttagaaaagc ttcatgatgt     60

agtgtgtcgt ttcgatgtga cactgtctca cagagttaaa atgatgttaa ggaactgttc    120

aatggaaatt tagaaatttc tctttttctc aattttagtg ta                       162


<210> SEQ ID NO 98
<211> LENGTH: 20
<212> TYPE: DNA
<213> ORGANISM: Homo sapiens

<400> SEQUENCE: 98

gagaagtgag gtcagcagct                                                 20


<210> SEQ ID NO 99
<211> LENGTH: 22
<212> TYPE: DNA
<213> ORGANISM: Homo sapiens

<400> SEQUENCE: 99

tttctaaatt tccattgaac ag                                              22


<210> SEQ ID NO 100
<211> LENGTH: 160
<212> TYPE: DNA
<213> ORGANISM: Homo sapiens

<400> SEQUENCE: 100

atggctgaat agtattccct tgtgtatata tctatttatc cttttattca ttgatggaca     60

cttaggctga ttttctctct tctcatggct ggcttctcat caccctttgg tcctcctgta    120

tcctcgtgta ataaagctct tccccaatat ctcgatagat                          160


<210> SEQ ID NO 101
<211> LENGTH: 22
<212> TYPE: DNA
<213> ORGANISM: Homo sapiens
```

<400> SEQUENCE: 101
ggctgaatag tattcccttg tg 22

<210> SEQ ID NO 102
<211> LENGTH: 20
<212> TYPE: DNA
<213> ORGANISM: Homo sapiens

<400> SEQUENCE: 102
tcgagatatt ggggaagagc 20

<210> SEQ ID NO 103
<211> LENGTH: 199
<212> TYPE: DNA
<213> ORGANISM: Homo sapiens

<400> SEQUENCE: 103
cattttaact tgattacctc cacaaagact attccagaat aaggttatgt tctgaggtat 60
taggggttac aacttcaaca tatgaatttt gagtggacac aattcaaccc atagcacctc 120
cgtgtaagag ctgggaaggg aaagtggcta agttgtgcaa atgtgcacat tggttggaga 180
tgattaactt ctggcatgt 199

<210> SEQ ID NO 104
<211> LENGTH: 22
<212> TYPE: DNA
<213> ORGANISM: Homo sapiens

<400> SEQUENCE: 104
cctccacaaa gactattcca ga 22

<210> SEQ ID NO 105
<211> LENGTH: 20
<212> TYPE: DNA
<213> ORGANISM: Homo sapiens

<400> SEQUENCE: 105
cactttccct tcccagctct 20

<210> SEQ ID NO 106
<211> LENGTH: 157
<212> TYPE: DNA
<213> ORGANISM: Homo sapiens

<400> SEQUENCE: 106 aggggaaat tggcaatctg attctaaaat tcatacggaa aaaaacaatg gagttagaat 60
aactaaaaca agtccgaaaa agaaaaagaa atggaggact aatgctacct gatttcaagt 120
cttatcttat aaatctacat caataaagga caagttg 157

<210> SEQ ID NO 107
<211> LENGTH: 20
<212> TYPE: DNA
<213> ORGANISM: Homo sapiens

<400> SEQUENCE: 107
gaaattggca atctgattct 20

<210> SEQ ID NO 108
<211> LENGTH: 21
<212> TYPE: DNA

<213> ORGANISM: Homo sapiens

<400> SEQUENCE: 108
caacttgtcc tttattgatg t 21

<210> SEQ ID NO 109
<211> LENGTH: 173
<212> TYPE: DNA
<213> ORGANISM: Homo sapiens

<400> SEQUENCE: 109
tctgtgtttg tctatgttga taaaacattg aaatgccaaa tagctcaaag gtcattcact 60
taagaaatct aagtactgat aacatcttag ccccgattct tcataggcat tgttaagcct 120
attataattt tggttcagag agaaggtaaa ctatattcca gacaggcata taa 173

<210> SEQ ID NO 110
<211> LENGTH: 22
<212> TYPE: DNA
<213> ORGANISM: Homo sapiens

<400> SEQUENCE: 110
ctatgttgat aaaacattga aa 22

<210> SEQ ID NO 111
<211> LENGTH: 20
<212> TYPE: DNA
<213> ORGANISM: Homo sapiens

<400> SEQUENCE: 111
gcctgtctgg aatatagttt 20

<210> SEQ ID NO 112
<211> LENGTH: 126
<212> TYPE: DNA
<213> ORGANISM: Homo sapiens

<400> SEQUENCE: 112
tgcagggcat ataatctaag ctgtaaacgt cctgtcagaa gacaacatat tcatcttgct 60
aaggtttaag ctatatgact ggcactgtgc tcaactcaga gtcattgaat gaacagtatt 120
tattta 126

<210> SEQ ID NO 113
<211> LENGTH: 22
<212> TYPE: DNA
<213> ORGANISM: Homo sapiens

<400> SEQUENCE: 113
cagggcatat aatctaagct gt 22

<210> SEQ ID NO 114
<211> LENGTH: 21
<212> TYPE: DNA
<213> ORGANISM: Homo sapiens

<400> SEQUENCE: 114
caatgactct gagttgagca c 21

<210> SEQ ID NO 115
<211> LENGTH: 132
<212> TYPE: DNA
<213> ORGANISM: Homo sapiens

<400> SEQUENCE: 115
ttcacattat tcccttaaaa taaactctct ccctcccctc tcccgtctca accttgtccc 60
tttctttata taatgggtaa ttcgttaatg tcagcagaat agttttgggg ccataatggc 120
aagtatcacg tg 132

<210> SEQ ID NO 116
<211> LENGTH: 19
<212> TYPE: DNA
<213> ORGANISM: Homo sapiens

<400> SEQUENCE: 116
aactctctcc ctcccctct 19

<210> SEQ ID NO 117
<211> LENGTH: 20
<212> TYPE: DNA
<213> ORGANISM: Homo sapiens

<400> SEQUENCE: 117
tatggcccca aaactattct 20

<210> SEQ ID NO 118
<211> LENGTH: 110
<212> TYPE: DNA
<213> ORGANISM: Homo sapiens

<400> SEQUENCE: 118
tcaggaagca acaagtactg ggcagattga tactgtagct aggctctagc tctatacctc 60
tagaataaat gttacaaact agcaacttga aagctaaacc tggcccacag 110

<210> SEQ ID NO 119
<211> LENGTH: 20
<212> TYPE: DNA
<213> ORGANISM: Homo sapiens

<400> SEQUENCE: 119
acaagtactg ggcagattga 20

<210> SEQ ID NO 120
<211> LENGTH: 20
<212> TYPE: DNA
<213> ORGANISM: Homo sapiens

<400> SEQUENCE: 120
gccaggttta gctttcaagt 20

<210> SEQ ID NO 121
<211> LENGTH: 106
<212> TYPE: DNA
<213> ORGANISM: Homo sapiens

<400> SEQUENCE: 121
tggttcttga gaattttata tcaggagaaa cactgtcagt ctgtattgaa aggaacagag 60
aaaattcgaa attaaagaag actattaaac ctccaaaatt ctggca 106

<210> SEQ ID NO 122
<211> LENGTH: 22
<212> TYPE: DNA
<213> ORGANISM: Homo sapiens

<400> SEQUENCE: 122
ttttatatca ggagaaacac tg 22

<210> SEQ ID NO 123
<211> LENGTH: 21
<212> TYPE: DNA
<213> ORGANISM: Homo sapiens

<400> SEQUENCE: 123
ccagaatttt ggaggtttaa t 21

<210> SEQ ID NO 124
<211> LENGTH: 171
<212> TYPE: DNA
<213> ORGANISM: Homo sapiens

<400> SEQUENCE: 124
gcatcaaact acacactgtc attcctcctt tatctccaaa agcttgaaaa ttcctcactt 60
gtatctcatt ctttctctct tagaaaactg atcacctctg atgaattaga acggaatgac 120
caagctttgg gagaggcaaa agaatctcgg tgttaaagac tcagagttta a 171

<210> SEQ ID NO 125
<211> LENGTH: 22
<212> TYPE: DNA
<213> ORGANISM: Homo sapiens

<400> SEQUENCE: 125
tgtcattcct cctttatctc ca 22

<210> SEQ ID NO 126
<211> LENGTH: 20
<212> TYPE: DNA
<213> ORGANISM: Homo sapiens

<400> SEQUENCE: 126
ttcttttgcc tctcccaaag 20

<210> SEQ ID NO 127
<211> LENGTH: 163
<212> TYPE: DNA
<213> ORGANISM: Homo sapiens

<400> SEQUENCE: 127
ttgaaaatta agaaaccctg gcacagtgtt gactggagcc acttacctta atagaaaata 60
aagctcacat atatccataa tgaaaagcag agaccagcac aaccatagtc acctgacagt 120
tttaaaatcc aaggccagga tcttctcaac tcaggcccac tca 163

<210> SEQ ID NO 128
<211> LENGTH: 20
<212> TYPE: DNA
<213> ORGANISM: Homo sapiens

<400> SEQUENCE: 128
accctggcac agtgttgact 20

<210> SEQ ID NO 129
<211> LENGTH: 20
<212> TYPE: DNA
<213> ORGANISM: Homo sapiens

<400> SEQUENCE: 129
tgggcctgag ttgagaagat 20

<210> SEQ ID NO 130
<211> LENGTH: 20
<212> TYPE: DNA
<213> ORGANISM: Homo sapiens

<400> SEQUENCE: 130
tttttcccat ttccaactct 20

<210> SEQ ID NO 131
<211> LENGTH: 122
<212> TYPE: DNA
<213> ORGANISM: Homo sapiens

<400> SEQUENCE: 131
aaaaaaaaag atgagacagg caggtgcgaa agaaataaaa gtcaaaactg atccagttgg 60
gaaactcaga attgacagtt acgtgtcctt tcatttattg atattttgag attcacaggg 120
gt 122

<210> SEQ ID NO 132
<211> LENGTH: 20
<212> TYPE: DNA
<213> ORGANISM: Homo sapiens

<400> SEQUENCE: 132
aaaagatgag acaggcaggt 20

<210> SEQ ID NO 133
<211> LENGTH: 20
<212> TYPE: DNA
<213> ORGANISM: Homo sapiens

<400> SEQUENCE: 133
acccctgtga atctcaaaat 20

<210> SEQ ID NO 134
<211> LENGTH: 150
<212> TYPE: DNA
<213> ORGANISM: Homo sapiens

<400> SEQUENCE: 134
gagttaaata aagcacttgc ttctattgtt tgtacctaaa cttaacagaa cacagtaagt 60
aacaagtcat tgggatgcag aaaagaaaaa agagagtgaa ggaaggagaa aaggtgaagg 120
gagaatggaa gagaggaagg gagggaggaa 150

<210> SEQ ID NO 135
<211> LENGTH: 21
<212> TYPE: DNA
<213> ORGANISM: Homo sapiens

<400> SEQUENCE: 135
gcacttgctt ctattgtttg t 21

<210> SEQ ID NO 136
<211> LENGTH: 20
<212> TYPE: DNA
<213> ORGANISM: Homo sapiens

<400> SEQUENCE: 136
cccttcctct cttccattct 20

<210> SEQ ID NO 137
<211> LENGTH: 129
<212> TYPE: DNA
<213> ORGANISM: Homo sapiens

<400> SEQUENCE: 137
aaacgagcca ccagtgggag cactgcaggt atctgtgtga gacccgtact tcacaactcc 60
tgctttccct ccataaagta gcttgcattt tccacattga ctttgcagtt ctttggtatc 120
tgtattggt 129

<210> SEQ ID NO 138
<211> LENGTH: 18
<212> TYPE: DNA
<213> ORGANISM: Homo sapiens

<400> SEQUENCE: 138
gtgggagcac tgcaggta 18

<210> SEQ ID NO 139
<211> LENGTH: 21
<212> TYPE: DNA
<213> ORGANISM: Homo sapiens

<400> SEQUENCE: 139
acagatacca aagaactgca a 21

<210> SEQ ID NO 140
<211> LENGTH: 145
<212> TYPE: DNA
<213> ORGANISM: Homo sapiens

<400> SEQUENCE: 140
tggacacctt tcaacttaga aatcataaac agattcattt ccttaaagtt aatgaaaaga 60
attaacagac cctcctcaaa aaagacatat atgcagccta caatcatatg aaaaaaagtt 120
caacattact gttcagcaaa tcaaa 145

<210> SEQ ID NO 141
<211> LENGTH: 20
<212> TYPE: DNA
<213> ORGANISM: Homo sapiens

<400> SEQUENCE: 141
tggacacctt tcaacttaga 20

<210> SEQ ID NO 142
<211> LENGTH: 22
<212> TYPE: DNA
<213> ORGANISM: Homo sapiens

<400> SEQUENCE: 142
gaacagtaat gttgaacttt tt 22

<210> SEQ ID NO 143
<211> LENGTH: 155
<212> TYPE: DNA
<213> ORGANISM: Homo sapiens

<400> SEQUENCE: 143
tggatacatt cctagaaata gatggaaact gctcttgcaa aaagcttagc acatgttaaa 60
aattttagaa acaatttgcc aaagtttatt tagtctagtg attttgacag gttaaatgga 120
ccctttgaga tctttttcc tcaagtacaa aggct 155

<210> SEQ ID NO 144
<211> LENGTH: 21
<212> TYPE: DNA
<213> ORGANISM: Homo sapiens

<400> SEQUENCE: 144
tcttgcaaaa agcttagcac a 21

<210> SEQ ID NO 145
<211> LENGTH: 21
<212> TYPE: DNA
<213> ORGANISM: Homo sapiens

<400> SEQUENCE: 145
aaaaagatct caaagggtcc a 21

<210> SEQ ID NO 146
<211> LENGTH: 119
<212> TYPE: DNA
<213> ORGANISM: Homo sapiens

<400> SEQUENCE: 146
gcttttgctg aacatcaagt ggtgagccag gactcaaagc cagatcttct tgtttccctg 60
ttaggtgttt gtagcacaac tggtatctgc agactatgct gctggaaggg ctagccgtc 119

<210> SEQ ID NO 147
<211> LENGTH: 20
<212> TYPE: DNA
<213> ORGANISM: Homo sapiens

<400> SEQUENCE: 147
gcttttgctg aacatcaagt 20

<210> SEQ ID NO 148
<211> LENGTH: 19
<212> TYPE: DNA
<213> ORGANISM: Homo sapiens

<400> SEQUENCE: 148
ccttccagca gcatagtct 19

<210> SEQ ID NO 149
<211> LENGTH: 161
<212> TYPE: DNA
<213> ORGANISM: Homo sapiens

<400> SEQUENCE: 149
actgtcctag aaaatccagg atgtgcagtg atcatgtatg aatgcatgga cctgcacaca 60
caggagtgaa caaaagaccc acccctgcca ggtcaccact catatctcac cccagcccac 120
gctagctcac actcctcccc acacaccact gacctcatca t 161

<210> SEQ ID NO 150
<211> LENGTH: 18
<212> TYPE: DNA
<213> ORGANISM: Homo sapiens

<400> SEQUENCE: 150

-continued aaatccagga tgtgcagt 18

<210> SEQ ID NO 151
<211> LENGTH: 19
<212> TYPE: DNA
<213> ORGANISM: Homo sapiens

<400> SEQUENCE: 151
atgatgaggt cagtggtgt 19

<210> SEQ ID NO 152
<211> LENGTH: 124
<212> TYPE: DNA
<213> ORGANISM: Homo sapiens

<400> SEQUENCE: 152
cacatcacag atcatagtaa atggctttaa ttttttaacg aaatctcact actgcaaatg 60
cattgttgtc ctagctaatg aatgcataga gtattgcctg caaaataata attgagattc 120
tatt 124

<210> SEQ ID NO 153
<211> LENGTH: 22
<212> TYPE: DNA
<213> ORGANISM: Homo sapiens

<400> SEQUENCE: 153
catcacagat catagtaaat gg 22

<210> SEQ ID NO 154
<211> LENGTH: 21
<212> TYPE: DNA
<213> ORGANISM: Homo sapiens

<400> SEQUENCE: 154
aattattatt ttgcaggcaa t 21

<210> SEQ ID NO 155
<211> LENGTH: 151
<212> TYPE: DNA
<213> ORGANISM: Homo sapiens

<400> SEQUENCE: 155
ttatcctcca catcctcatg aggcaaacac ctttcctacc ttaccgctcc ccagtggcct 60
ccctgttgcc ttcttattca agactaagac tctctagaat gttctttatc ctgagtccag 120
ctgattgtct atactaatat cagtacgggg t 151

<210> SEQ ID NO 156
<211> LENGTH: 20
<212> TYPE: DNA
<213> ORGANISM: Homo sapiens

<400> SEQUENCE: 156
catgaggcaa acacctttcc 20

<210> SEQ ID NO 157
<211> LENGTH: 22
<212> TYPE: DNA
<213> ORGANISM: Homo sapiens

<400> SEQUENCE: 157
gctggactca ggataaagaa ca 22

<210> SEQ ID NO 158
<211> LENGTH: 145
<212> TYPE: DNA
<213> ORGANISM: Homo sapiens

<400> SEQUENCE: 158
agggtgcagc actttattat ggaagcctga gctgactaat acaggtgtct ctatatctca 60
ctgagggaaa gtgacaggaa agtaagaacc atttatgtcc aagagtccag aggagtcaac 120
cagattctgg gggaaaagaa ggtac 145

<210> SEQ ID NO 159
<211> LENGTH: 20
<212> TYPE: DNA
<213> ORGANISM: Homo sapiens

<400> SEQUENCE: 159
tggaagcctg agctgactaa 20

<210> SEQ ID NO 160
<211> LENGTH: 20
<212> TYPE: DNA
<213> ORGANISM: Homo sapiens

<400> SEQUENCE: 160
ccttcttttc ccccagaatc 20

<210> SEQ ID NO 161
<211> LENGTH: 154
<212> TYPE: DNA
<213> ORGANISM: Homo sapiens

<400> SEQUENCE: 161
tgagaattta ggagaacaga agatcagagg gctgcacagg ctaaactaga caatgagccc 60
atgcaagtaa gttaagagga gaagcgggta agtatgcacc tgctttgtct aggtgaccag 120
caagcattta gcaatagtct tttcaaaaca acag 154

<210> SEQ ID NO 162
<211> LENGTH: 22
<212> TYPE: DNA
<213> ORGANISM: Homo sapiens

<400> SEQUENCE: 162
ttaggagaac agaagatcag ag 22

<210> SEQ ID NO 163
<211> LENGTH: 22
<212> TYPE: DNA
<213> ORGANISM: Homo sapiens

<400> SEQUENCE: 163
aaagactatt gctaaatgct tg 22

<210> SEQ ID NO 164
<211> LENGTH: 106
<212> TYPE: DNA
<213> ORGANISM: Homo sapiens

<400> SEQUENCE: 164
aaacaggcaa aataagcgta gggctgtgtg tgcaacagtt aatcataaag ccatcaccag 60

-continued gagacgtcac tgggcgcctt ctggagtcta tccgtcctaa ctttgc 106

<210> SEQ ID NO 165
<211> LENGTH: 20
<212> TYPE: DNA
<213> ORGANISM: Homo sapiens

<400> SEQUENCE: 165
taagcgtagg gctgtgtgtg 20

<210> SEQ ID NO 166
<211> LENGTH: 21
<212> TYPE: DNA
<213> ORGANISM: Homo sapiens

<400> SEQUENCE: 166
ggacggatag actccagaag g 21

<210> SEQ ID NO 167
<211> LENGTH: 105
<212> TYPE: DNA
<213> ORGANISM: Homo sapiens

<400> SEQUENCE: 167
gaatgacctt ggcactttta tcaaacatca actggccaca cacaggtgag tctacttctg 60
gacacttatc ctgttccatt catctgtata tctctatcct tacac 105

<210> SEQ ID NO 168
<211> LENGTH: 23
<212> TYPE: DNA
<213> ORGANISM: Homo sapiens

<400> SEQUENCE: 168
gaatgacctt ggcactttta tca 23

<210> SEQ ID NO 169
<211> LENGTH: 27
<212> TYPE: DNA
<213> ORGANISM: Homo sapiens

<400> SEQUENCE: 169
aaggatagag atatacagat gaatgga 27

<210> SEQ ID NO 170
<211> LENGTH: 129
<212> TYPE: DNA
<213> ORGANISM: Homo sapiens

<400> SEQUENCE: 170
ctgctggaat aggctgcttg gccatgttct tggaagctac caccatatca aggtaatttc 60
ccacacaaca ttccagcccc tgctttcctc tctggcctta tctagggcca ttccccaact 120
caggtgaat 129

<210> SEQ ID NO 171
<211> LENGTH: 20
<212> TYPE: DNA
<213> ORGANISM: Homo sapiens

<400> SEQUENCE: 171
ggccatgttc ttggaagcta 20

<210> SEQ ID NO 172
<211> LENGTH: 20
<212> TYPE: DNA
<213> ORGANISM: Homo sapiens

<400> SEQUENCE: 172
ttcacctgag ttggggaatg 20

<210> SEQ ID NO 173
<211> LENGTH: 138
<212> TYPE: DNA
<213> ORGANISM: Homo sapiens

<400> SEQUENCE: 173
acctttgttc catgcaccgc gcaaatacct gggaaccctt attgcccaac tcaagagcca 60
gagtcctctg tcatcatttt gcctctctcc taagtgagag gactgagtgc agacttggtg 120
tttgtgggtg aggcatgt 138

<210> SEQ ID NO 174
<211> LENGTH: 18
<212> TYPE: DNA
<213> ORGANISM: Homo sapiens

<400> SEQUENCE: 174
catgcaccgc gcaaatac 18

<210> SEQ ID NO 175
<211> LENGTH: 19
<212> TYPE: DNA
<213> ORGANISM: Homo sapiens

<400> SEQUENCE: 175
atgcctcacc cacaaacac 19

<210> SEQ ID NO 176
<211> LENGTH: 159
<212> TYPE: DNA
<213> ORGANISM: Homo sapiens

<400> SEQUENCE: 176
ctcctgagtc caagcccttc tcactcacct ctttcttgaa ctaatttctt cctgtttttt 60
tccagtcctc ccttctgttc atgtctctcc tctgcacact tccattttgt ggttcagaaa 120
atgtcaccgt cccagtcaca cttgccttat ggctgttgt 159

<210> SEQ ID NO 177
<211> LENGTH: 20
<212> TYPE: DNA
<213> ORGANISM: Homo sapiens

<400> SEQUENCE: 177
tccaagccct tctcactcac 20

<210> SEQ ID NO 178
<211> LENGTH: 20
<212> TYPE: DNA
<213> ORGANISM: Homo sapiens

<400> SEQUENCE: 178
ctgggacggt gacattttct 20

<210> SEQ ID NO 179

<211> LENGTH: 132
<212> TYPE: DNA
<213> ORGANISM: Homo sapiens

<400> SEQUENCE: 179
cccaggaaga gtggaaagat taacctttgt gagccaaacc agtgacactt gattacttga 60
cagaactaat ccttctgtcc tgatgacaga acttcaacta cacaggtaca tgcaagctaa 120
tatctgttgt aa 132

<210> SEQ ID NO 180
<211> LENGTH: 21
<212> TYPE: DNA
<213> ORGANISM: Homo sapiens

<400> SEQUENCE: 180
cccaggaaga gtggaaagat t 21

<210> SEQ ID NO 181
<211> LENGTH: 21
<212> TYPE: DNA
<213> ORGANISM: Homo sapiens

<400> SEQUENCE: 181
ttagcttgca tgtacctgtg t 21

<210> SEQ ID NO 182
<211> LENGTH: 165
<212> TYPE: DNA
<213> ORGANISM: Homo sapiens

<400> SEQUENCE: 182
gcctggcaag ctagatgggg tgaattttca cctgccacag ccgcaagtca aagccaccgg 60
cttctctctt ctccctccca ttgctcctga cagccagggt taatattttg cctcatgtaa 120
acagggaggc atccacccga gaatctcccc tcagcccaca taagc 165

<210> SEQ ID NO 183
<211> LENGTH: 20
<212> TYPE: DNA
<213> ORGANISM: Homo sapiens

<400> SEQUENCE: 183
agctagatgg ggtgaatttt 20

<210> SEQ ID NO 184
<211> LENGTH: 18
<212> TYPE: DNA
<213> ORGANISM: Homo sapiens

<400> SEQUENCE: 184
tgggctgagg ggagattc 18

<210> SEQ ID NO 185
<211> LENGTH: 160
<212> TYPE: DNA
<213> ORGANISM: Homo sapiens

<400> SEQUENCE: 185
atcaagctaa ttaatgttat ctatcacttc acatagttca accttttttt gtggtgagag 60
tactgaagat ctactctctt agcaattttc aaatctaaaa tacattatta ttaacacagt 120
cactgtgccg tacgttagct ctgaggacct tattcatttt 160

<210> SEQ ID NO 186
<211> LENGTH: 22
<212> TYPE: DNA
<213> ORGANISM: Homo sapiens

<400> SEQUENCE: 186
atcaagctaa ttaatgttat ct 22

<210> SEQ ID NO 187
<211> LENGTH: 20
<212> TYPE: DNA
<213> ORGANISM: Homo sapiens

<400> SEQUENCE: 187
aatgaataag gtcctcagag 20

<210> SEQ ID NO 188
<211> LENGTH: 124
<212> TYPE: DNA
<213> ORGANISM: Homo sapiens

<400> SEQUENCE: 188
tttaatctga tcattgccct atgaggtagg gagtattctg attcccattt tataaataag 60
gaacccgagg cttagagagc atcagtgact tgttcaaggt cacccacagc tgtcaagtga 120
caga 124

<210> SEQ ID NO 189
<211> LENGTH: 21
<212> TYPE: DNA
<213> ORGANISM: Homo sapiens

<400> SEQUENCE: 189
tttaatctga tcattgccct a 21

<210> SEQ ID NO 190
<211> LENGTH: 18
<212> TYPE: DNA
<213> ORGANISM: Homo sapiens

<400> SEQUENCE: 190
agctgtgggt gaccttga 18

<210> SEQ ID NO 191
<211> LENGTH: 128
<212> TYPE: DNA
<213> ORGANISM: Homo sapiens

<400> SEQUENCE: 191
tgtcccacca ttgtgtatta ggtttgtaga gcgtagacaa cttgcctttt tagtttgtag 60
gtttctgtat caagagaaga tgtgtgtggg cctaacctag attacaggat cctggacttc 120
aagtctga 128

<210> SEQ ID NO 192
<211> LENGTH: 20
<212> TYPE: DNA
<213> ORGANISM: Homo sapiens

<400> SEQUENCE: 192
tgtcccacca ttgtgtatta 20

<210> SEQ ID NO 193
<211> LENGTH: 20
<212> TYPE: DNA
<213> ORGANISM: Homo sapiens

<400> SEQUENCE: 193
tcagacttga agtccaggat 20

<210> SEQ ID NO 194
<211> LENGTH: 128
<212> TYPE: DNA
<213> ORGANISM: Homo sapiens

<400> SEQUENCE: 194
tcatttgcta aggtcggata gctcctaatt ggcaaagtca cgatgggatc ccagggattc 60
tgaggatgaa gcctgtgttt aataactatt atgccaagtg agcattttca aatatatgag 120
agaaatta 128

<210> SEQ ID NO 195
<211> LENGTH: 19
<212> TYPE: DNA
<213> ORGANISM: Homo sapiens

<400> SEQUENCE: 195
catttgctaa ggtcggata 19

<210> SEQ ID NO 196
<211> LENGTH: 20
<212> TYPE: DNA
<213> ORGANISM: Homo sapiens

<400> SEQUENCE: 196
tatttgaaaa tgctcacttg 20

<210> SEQ ID NO 197
<211> LENGTH: 159
<212> TYPE: DNA
<213> ORGANISM: Homo sapiens

<400> SEQUENCE: 197
cattgcttca ggggtgttag ttttgtgttc acaactagat tataaactcc tcttgcattc 60
ctgatggcag tgacttgaag gcatttattt gaagaataat agacatacag aaaggggcac 120
atgtcataaa ggtacagctg gacgactttt cacaaagtg 159

<210> SEQ ID NO 198
<211> LENGTH: 20
<212> TYPE: DNA
<213> ORGANISM: Homo sapiens

<400> SEQUENCE: 198
gcttcagggg tgttagtttt 20

<210> SEQ ID NO 199
<211> LENGTH: 20
<212> TYPE: DNA
<213> ORGANISM: Homo sapiens

<400> SEQUENCE: 199
ctttgtgaaa agtcgtccag 20

```
<210> SEQ ID NO 200
<211> LENGTH: 117
<212> TYPE: DNA
<213> ORGANISM: Homo sapiens

<400> SEQUENCE: 200

gagaggatgg tgccatcatg gaaagcatgg ggcagtcatg gagatgacgg agtagctcat     60

ggagaagata atgccatcat ggaaggcata gtgcagtcat ggagatgatg gtgcagc       117


<210> SEQ ID NO 201
<211> LENGTH: 18
<212> TYPE: DNA
<213> ORGANISM: Homo sapiens

<400> SEQUENCE: 201

ccatcatgga aagcatgg                                                   18


<210> SEQ ID NO 202
<211> LENGTH: 20
<212> TYPE: DNA
<213> ORGANISM: Homo sapiens

<400> SEQUENCE: 202

tcatctccat gactgcacta                                                 20


<210> SEQ ID NO 203
<211> LENGTH: 167
<212> TYPE: DNA
<213> ORGANISM: Homo sapiens

<400> SEQUENCE: 203

atggggcagt catggagatg acggagtagc tcatggagaa aataatgcca tcatggaagg     60

catagtgcag tcatggagat gatggtgcag ctcatggaga agatggtgcc atcatggaag    120

gcatggtgca atcatggagt agacagtgca gctgggccaa gattctc                  167


<210> SEQ ID NO 204
<211> LENGTH: 20
<212> TYPE: DNA
<213> ORGANISM: Homo sapiens

<400> SEQUENCE: 204

gagatgacgg agtagctcat                                                 20


<210> SEQ ID NO 205
<211> LENGTH: 18
<212> TYPE: DNA
<213> ORGANISM: Homo sapiens

<400> SEQUENCE: 205

cccagctgca ctgtctac                                                   18


<210> SEQ ID NO 206
<211> LENGTH: 128
<212> TYPE: DNA
<213> ORGANISM: Homo sapiens

<400> SEQUENCE: 206

gatgtgcctc tcttgttcca atcacaggac aggggtataa ctaggggcac tgtctatact     60

ggctgcactc tggccagtgc tgtcccaggt agattcatca gggtctagag cttcagctaa    120

cagcatga                                                             128
```

<210> SEQ ID NO 207
<211> LENGTH: 20
<212> TYPE: DNA
<213> ORGANISM: Homo sapiens

<400> SEQUENCE: 207
tcttgttcca atcacaggac 20

<210> SEQ ID NO 208
<211> LENGTH: 20
<212> TYPE: DNA
<213> ORGANISM: Homo sapiens

<400> SEQUENCE: 208
atgctgttag ctgaagctct 20

<210> SEQ ID NO 209
<211> LENGTH: 109
<212> TYPE: DNA
<213> ORGANISM: Homo sapiens

<400> SEQUENCE: 209
ttttattcat taagttgaaa gctcctaaag cagagggacc atatttttat gtcccaactc 60
tccttaaggc cttgcctatg atagcacatc tcttcaatag aattgtcct 109

<210> SEQ ID NO 210
<211> LENGTH: 20
<212> TYPE: DNA
<213> ORGANISM: Homo sapiens

<400> SEQUENCE: 210
tgaaagctcc taaagcagag 20

<210> SEQ ID NO 211
<211> LENGTH: 20
<212> TYPE: DNA
<213> ORGANISM: Homo sapiens

<400> SEQUENCE: 211
ttgaagagat gtgctatcat 20

<210> SEQ ID NO 212
<211> LENGTH: 163
<212> TYPE: DNA
<213> ORGANISM: Homo sapiens

<400> SEQUENCE: 212
cacataacta ataaatttgt aagtatgtgc aacggctcac acttgcttcc agaatggcac 60
ctaaaaaaca gatttacctc tccccaaatt cagatatgga attaaatgta atgtcaggaa 120
aactgtctaa gagttggaaa tgggaaaaaa atgttctttt ggt 163

<210> SEQ ID NO 213
<211> LENGTH: 21
<212> TYPE: DNA
<213> ORGANISM: Homo sapiens

<400> SEQUENCE: 213
aatttgtaag tatgtgcaac g 21

<210> SEQ ID NO 214
<211> LENGTH: 207

<212> TYPE: DNA
<213> ORGANISM: Homo sapiens

<400> SEQUENCE: 214
aaagaccagc ttttagctga acatcagggc tgccttcaga gtttaattac cgccctcccc 60
atggggccaa atgagccatc gactcctccc aagggggttc ggcttggtac tgatctttaa 120
gtaagtaaac gctaaaccag ctcatcttaa agcgcccaca tctgatttcc tgctctgctg 180
caagacagta ggtgactggt aatgacc 207

<210> SEQ ID NO 215
<211> LENGTH: 20
<212> TYPE: DNA
<213> ORGANISM: Homo sapiens

<400> SEQUENCE: 215
agggctgcct tcagagttta 20

<210> SEQ ID NO 216
<211> LENGTH: 20
<212> TYPE: DNA
<213> ORGANISM: Homo sapiens

<400> SEQUENCE: 216
gcgctttaag atgagctggt 20

<210> SEQ ID NO 217
<211> LENGTH: 192
<212> TYPE: DNA
<213> ORGANISM: Homo sapiens

<400> SEQUENCE: 217
actctgctcc cagtgtgaac atggggaaag ttgattaaac tctctgactt cagattcctc 60
atgtaaaatg tggggaaaca gctctgactt aatggtgtca ctgtgaggag taaatgaggt 120
agcatattta aaggattttg tatagtgctg gtgacagtaa ccagccaata gatgatatag 180
ctagtaatag ca 192

<210> SEQ ID NO 218
<211> LENGTH: 20
<212> TYPE: DNA
<213> ORGANISM: Homo sapiens

<400> SEQUENCE: 218
tgaacatggg gaaagttgat 20

<210> SEQ ID NO 219
<211> LENGTH: 22
<212> TYPE: DNA
<213> ORGANISM: Homo sapiens

<400> SEQUENCE: 219
tcaccagcac tatacaaaat cc 22

<210> SEQ ID NO 220
<211> LENGTH: 170
<212> TYPE: DNA
<213> ORGANISM: Homo sapiens

<400> SEQUENCE: 220
cttcactgac cacttcctta actgtccact ccgaaacacc ccttcttcct gttcttccaa 60

-continued

```
tacaccaaac tctttcttgc ctctgtgtgc ttgcccatgc tgttccttct ggcttcttcc    120

ttcacattca agtcttgact tagatgtcac ttgccaaggg agaccttgga               170


<210> SEQ ID NO 221
<211> LENGTH: 21
<212> TYPE: DNA
<213> ORGANISM: Homo sapiens

<400> SEQUENCE: 221

acttccttaa ctgtccactc c                                               21


<210> SEQ ID NO 222
<211> LENGTH: 19
<212> TYPE: DNA
<213> ORGANISM: Homo sapiens

<400> SEQUENCE: 222

ccttggcaag tgacatcta                                                  19


<210> SEQ ID NO 223
<211> LENGTH: 181
<212> TYPE: DNA
<213> ORGANISM: Homo sapiens

<400> SEQUENCE: 223

aaacatccca atagacaaaa ctccaagaag agtcaaaaca agaataaagt acaggtcatc     60

ttttcttttg cactcctgac agcactttgt acatggtaat aataatctac caattaacta    120

cataagccac atggttttat catagtgtga agctttgtat ccagaaagga gagaaggctc    180

c                                                                    181


<210> SEQ ID NO 224
<211> LENGTH: 22
<212> TYPE: DNA
<213> ORGANISM: Homo sapiens

<400> SEQUENCE: 224

ccaagaagag tcaaaacaag aa                                              22


<210> SEQ ID NO 225
<211> LENGTH: 21
<212> TYPE: DNA
<213> ORGANISM: Homo sapiens

<400> SEQUENCE: 225

tctcctttct ggatacaaag c                                               21


<210> SEQ ID NO 226
<211> LENGTH: 149
<212> TYPE: DNA
<213> ORGANISM: Homo sapiens

<400> SEQUENCE: 226

ggcagaggca tggggtgcat agggatatgg ggtgggccag tttgctcctc agaccagaag     60

gggtgcagga ctccccccga tcaggatcat ggagaaaggt gtggacagag gaagggaggg    120

agggagaaat ggcagctgcc ctgcagtgg                                      149


<210> SEQ ID NO 227
<211> LENGTH: 20
<212> TYPE: DNA
<213> ORGANISM: Homo sapiens
```

<400> SEQUENCE: 227
ttgctcctca gaccagaagg 20

<210> SEQ ID NO 228
<211> LENGTH: 20
<212> TYPE: DNA
<213> ORGANISM: Homo sapiens

<400> SEQUENCE: 228
ctcccttcct ctgtccacac 20

<210> SEQ ID NO 229
<211> LENGTH: 165
<212> TYPE: DNA
<213> ORGANISM: Homo sapiens

<400> SEQUENCE: 229
cagggactaa gtgtctctga caatacattc agccactact acagtatgaa gccagcccct 60
catccccacc ttcagagacc cctggtgcct cagattcctc ggccattctg gagctgctgt 120
gcccgaggct tgtgtagttg gagatcattt tggcagtcag tgctg 165

<210> SEQ ID NO 230
<211> LENGTH: 22
<212> TYPE: DNA
<213> ORGANISM: Homo sapiens

<400> SEQUENCE: 230
tgtctctgac aatacattca gc 22

<210> SEQ ID NO 231
<211> LENGTH: 20
<212> TYPE: DNA
<213> ORGANISM: Homo sapiens

<400> SEQUENCE: 231
ctgactgcca aaatgatctc 20

<210> SEQ ID NO 232
<211> LENGTH: 181
<212> TYPE: DNA
<213> ORGANISM: Homo sapiens

<400> SEQUENCE: 232
cctgtctccg tgcgtgaaag ccggctccaa agtgccttct gtcctatctg ccttccgcac 60
ctggctttcc tgaaagaaag aaaacgcgtg gcttatcttt tcacggcacg ccaccttcac 120
tctcactttt tcttttctaa taaatacctc tggatgggtt agtggtaatc tctcctcaaa 180
c 181

<210> SEQ ID NO 233
<211> LENGTH: 20
<212> TYPE: DNA
<213> ORGANISM: Homo sapiens

<400> SEQUENCE: 233
gctccaaagt gccttctgtc 20

<210> SEQ ID NO 234
<211> LENGTH: 20
<212> TYPE: DNA

<213> ORGANISM: Homo sapiens

<400> SEQUENCE: 234
ccactaaccc atccagaggt 20

<210> SEQ ID NO 235
<211> LENGTH: 198
<212> TYPE: DNA
<213> ORGANISM: Homo sapiens

<400> SEQUENCE: 235
gggagcacaa cctaggcccc tcctggggag gtggtggagt cagaatcacg taagagacaa 60
agttccagtc cctcagtgcc ggctccattg tcccctggac ttcccttaca aaccacagat 120
gcaaagagag cacttctcgg aatctccaca cagccacggt ggagcactca acccacgcga 180
ccctcgggcg caggtgct 198

<210> SEQ ID NO 236
<211> LENGTH: 20
<212> TYPE: DNA
<213> ORGANISM: Homo sapiens

<400> SEQUENCE: 236
ctggggaggt ggtggagtca 20

<210> SEQ ID NO 237
<211> LENGTH: 20
<212> TYPE: DNA
<213> ORGANISM: Homo sapiens

<400> SEQUENCE: 237
gagtgctcca ccgtggctgt 20

<210> SEQ ID NO 238
<211> LENGTH: 161
<212> TYPE: DNA
<213> ORGANISM: Homo sapiens

<400> SEQUENCE: 238
cctgagaagc ttccagcaaa gcaccagcac gaaccgcccc acctccccac ctccccgcaa 60
gcgttgccgg gactgacaga ttacagagct ctggtccctc tgcactcctg ctctgccacc 120
cccagggtgt cagaatgtgc cccccacaca gtttccaaaa g 161

<210> SEQ ID NO 239
<211> LENGTH: 18
<212> TYPE: DNA
<213> ORGANISM: Homo sapiens

<400> SEQUENCE: 239
aaagcaccag cacgaacc 18

<210> SEQ ID NO 240
<211> LENGTH: 18
<212> TYPE: DNA
<213> ORGANISM: Homo sapiens

<400> SEQUENCE: 240
ggggcacatt ctgacacc 18

<210> SEQ ID NO 241
<211> LENGTH: 162

<212> TYPE: DNA
<213> ORGANISM: Homo sapiens

<400> SEQUENCE: 241
atggagctgc tgcgccggcc tgagctctga tccctcctcc gacccagcct caccctgcaa 60
gcagcaccat gtggggctca gaatggggat cttaagggac cctccccaca acctcccgat 120
aagcctttcc acggagggcc caagcggaga caggagaaca ct 162

<210> SEQ ID NO 242
<211> LENGTH: 19
<212> TYPE: DNA
<213> ORGANISM: Homo sapiens

<400> SEQUENCE: 242
ctgagctctg atccctcct 19

<210> SEQ ID NO 243
<211> LENGTH: 18
<212> TYPE: DNA
<213> ORGANISM: Homo sapiens

<400> SEQUENCE: 243
ttctcctgtc tccgcttg 18

<210> SEQ ID NO 244
<211> LENGTH: 194
<212> TYPE: DNA
<213> ORGANISM: Homo sapiens

<400> SEQUENCE: 244
actttcagaa tgtgctgcct tccacgtgtg aaccagactg agctcctttc tgccactgat 60
gttgaattgt ccatttgctc acatcagtgt ccacgtggca aatccacagg gcgtgggtgg 120
gatcctgcag tctagacaaa gccaaggagc accgctggag gccacgttgg gcttcccaat 180
ccacatgcaa accc 194

<210> SEQ ID NO 245
<211> LENGTH: 20
<212> TYPE: DNA
<213> ORGANISM: Homo sapiens

<400> SEQUENCE: 245
cctttctgcc actgatgttg 20

<210> SEQ ID NO 246
<211> LENGTH: 19
<212> TYPE: DNA
<213> ORGANISM: Homo sapiens

<400> SEQUENCE: 246
ttgcatgtgg attgggaag 19

<210> SEQ ID NO 247
<211> LENGTH: 213
<212> TYPE: DNA
<213> ORGANISM: Homo sapiens

<400> SEQUENCE: 247
tctccagcca gcgtgtcaca aagccgctca cctgctcgtg tgagtgtctg aatgcacgtg 60
tttgagtgtc agaggcgtgt gaaccacagc aactcaatct tgaatagggg ctgggtaaag 120
tgaggctgag acctcccggg gctgcattcc cagatggtta aggcattcta agtcacaaga 180
tgagatagga agttcgcaca agacactggt cat 213

<210> SEQ ID NO 248
<211> LENGTH: 20
<212> TYPE: DNA
<213> ORGANISM: Homo sapiens

<400> SEQUENCE: 248
tcacctgctc gtgtgagtgt 20

<210> SEQ ID NO 249
<211> LENGTH: 20
<212> TYPE: DNA
<213> ORGANISM: Homo sapiens

<400> SEQUENCE: 249
ccttaaccat ctgggaatgc 20

<210> SEQ ID NO 250
<211> LENGTH: 152
<212> TYPE: DNA
<213> ORGANISM: Homo sapiens

<400> SEQUENCE: 250
ttgagtcctc ttaagtagtt actatagtgg agaacttgag tcattctttg tagcgtgctt 60
cgtagagcag cgtgtttgtt agaaggattt gttaatcctg tatagggtct ttacgaaggc 120
tgttttcatg gaagcttctc tttgttgact cc 152

<210> SEQ ID NO 251
<211> LENGTH: 22
<212> TYPE: DNA
<213> ORGANISM: Homo sapiens

<400> SEQUENCE: 251
tggagaactt gagtcattct tt 22

<210> SEQ ID NO 252
<211> LENGTH: 19
<212> TYPE: DNA
<213> ORGANISM: Homo sapiens

<400> SEQUENCE: 252
ggagtcaaca aagagaagc 19

<210> SEQ ID NO 253
<211> LENGTH: 174
<212> TYPE: DNA
<213> ORGANISM: Homo sapiens

<400> SEQUENCE: 253
cattctctcc agctgcaaac tttcttcaac tttcctaaat tcttactaaa ttcagaggaa 60
taggataaag atcacttaga gaaagggtgc ttatggacat agcctgagtt tcctttaacc 120
tctctgcaat gggtgctttt aactagcttc tacatggcaa gctgtttcag tttg 174

<210> SEQ ID NO 254
<211> LENGTH: 21
<212> TYPE: DNA
<213> ORGANISM: Homo sapiens

<400> SEQUENCE: 254
ctttcttcaa ctttcctaaa t 21

<210> SEQ ID NO 255
<211> LENGTH: 19
<212> TYPE: DNA
<213> ORGANISM: Homo sapiens

<400> SEQUENCE: 255
ttgccatgta gaagctagt 19

<210> SEQ ID NO 256
<211> LENGTH: 175
<212> TYPE: DNA
<213> ORGANISM: Homo sapiens

<400> SEQUENCE: 256
ggacatctgg aactgcacca gcacagaacc gacacgttgt tactcatcgt cactcggcag 60
ggctgaagac caccagaact catgacaggc agacgtgcct ggcccagttg aggatgtagc 120
ttcagagcca agcgccagtc ctgttggcca cgtgggctgg gggcaggata gacca 175

<210> SEQ ID NO 257
<211> LENGTH: 19
<212> TYPE: DNA
<213> ORGANISM: Homo sapiens

<400> SEQUENCE: 257
accagcacag aaccgacac 19

<210> SEQ ID NO 258
<211> LENGTH: 18
<212> TYPE: DNA
<213> ORGANISM: Homo sapiens

<400> SEQUENCE: 258
aacaggactg gcgcttgg 18

<210> SEQ ID NO 259
<211> LENGTH: 182
<212> TYPE: DNA
<213> ORGANISM: Homo sapiens

<400> SEQUENCE: 259
ggctggttct gcccttggga ggtggttcct ttggctggac cagaatgtct gaagatgatc 60
aggagagggc caagggttgg ggggtgcccc atgtgcaccc tgagaattgc accaggcaca 120
gtgagcaact tcagccctcc ttgtgcagag ctgcagcgta cagtgccagc cctcgctggc 180
cc 182

<210> SEQ ID NO 260
<211> LENGTH: 20
<212> TYPE: DNA
<213> ORGANISM: Homo sapiens

<400> SEQUENCE: 260
cttgggaggt ggttcctttg 20

<210> SEQ ID NO 261
<211> LENGTH: 18
<212> TYPE: DNA
<213> ORGANISM: Homo sapiens

<400> SEQUENCE: 261
ctgcacaagg agggctga 18

<210> SEQ ID NO 262
<211> LENGTH: 155
<212> TYPE: DNA
<213> ORGANISM: Homo sapiens

<400> SEQUENCE: 262
gttctcactt tactgagaaa cctggcagct tctcaggcca ccgcccaggt cacctgctca 60
ccagcaacgt gaaccacagg aactgaggct gtgcgggagg cggctctgct ctgtgctggg 120 ccccctcct cctcactcac cctcttcagt caaag 155

<210> SEQ ID NO 263
<211> LENGTH: 20
<212> TYPE: DNA
<213> ORGANISM: Homo sapiens

<400> SEQUENCE: 263
tactgagaaa cctggcagct 20

<210> SEQ ID NO 264
<211> LENGTH: 20
<212> TYPE: DNA
<213> ORGANISM: Homo sapiens

<400> SEQUENCE: 264
ctttgactga agagggtgag 20

<210> SEQ ID NO 265
<211> LENGTH: 180
<212> TYPE: DNA
<213> ORGANISM: Homo sapiens

<400> SEQUENCE: 265
ttagtattat tattttcata tatatttttt ataataatca tatattcaat tttatcatca 60
agaaaaaagt tttaaaattc aaaatccttt catgtgcact gttttaaact taggtagaag 120
aaaaaaagtc actgaaaatc caagatgtaa taaacaggcc caacaaaggc caacaaactt 180

<210> SEQ ID NO 266
<211> LENGTH: 20
<212> TYPE: DNA
<213> ORGANISM: Homo sapiens

<400> SEQUENCE: 266
ttcaatttta tcatcaagaa 20

<210> SEQ ID NO 267
<211> LENGTH: 20
<212> TYPE: DNA
<213> ORGANISM: Homo sapiens

<400> SEQUENCE: 267
ttgggcctgt ttattacatc 20

<210> SEQ ID NO 268
<211> LENGTH: 196
<212> TYPE: DNA
<213> ORGANISM: Homo sapiens

<400> SEQUENCE: 268

-continued agggaacatg gccttgccca cacagatttc agacatctgg ctccagaact gtgggaggac 60
acatttctgt tgtttagaac tgcatgtttt ttatactttg ttatggctgc cctaggcaac 120
taatacagat attattttcc acttctgaac ttagcaaaat atttttaaaa tgaaaattct 180
taaatgttgg cacagt 196

<210> SEQ ID NO 269
<211> LENGTH: 20
<212> TYPE: DNA
<213> ORGANISM: Homo sapiens

<400> SEQUENCE: 269
ttgcccacac agatttcaga 20

<210> SEQ ID NO 270
<211> LENGTH: 22
<212> TYPE: DNA
<213> ORGANISM: Homo sapiens

<400> SEQUENCE: 270
tgctaagttc agaagtggaa aa 22

<210> SEQ ID NO 271
<211> LENGTH: 120
<212> TYPE: DNA
<213> ORGANISM: Homo sapiens

<400> SEQUENCE: 271
ctggataaag gatgctacac gtccctggtg ggacagagca ggacggcagg ggatttcatt 60
acgccactca gaatggcagg caattgaaaa aacttataaa ttgtttattt ccagaatttt 120

<210> SEQ ID NO 272
<211> LENGTH: 20
<212> TYPE: DNA
<213> ORGANISM: Homo sapiens

<400> SEQUENCE: 272
ggataaagga tgctacacgt 20

<210> SEQ ID NO 273
<211> LENGTH: 20
<212> TYPE: DNA
<213> ORGANISM: Homo sapiens

<400> SEQUENCE: 273
aaaattctgg aaataaacaa 20

<210> SEQ ID NO 274
<211> LENGTH: 224
<212> TYPE: DNA
<213> ORGANISM: Homo sapiens

<400> SEQUENCE: 274
tgtcagtggt gtaatccgac tgtgaaagat cagtctaaca aaacagcggg gagagagagg 60
gctgaatcag agcaactagg tccaaagccg agggaaccac caacagatcc cctggtgacc 120
caacaagaaa tgctcacagt ctggacccag tcagagtctg caggacacag cagacattct 180
ggaagttaca acagccagga gcaagaggac gcatggcctg actg 224

<210> SEQ ID NO 275

<211> LENGTH: 20
<212> TYPE: DNA
<213> ORGANISM: Homo sapiens

<400> SEQUENCE: 275
gggagagaga gggctgaatc 20

<210> SEQ ID NO 276
<211> LENGTH: 21
<212> TYPE: DNA
<213> ORGANISM: Homo sapiens

<400> SEQUENCE: 276
gctcctggct gttgtaactt c 21

<210> SEQ ID NO 277
<211> LENGTH: 174
<212> TYPE: DNA
<213> ORGANISM: Homo sapiens

<400> SEQUENCE: 277
cgccagagca ccccttctca gaacagaaag cgtctctaca aagtgatccg gaagtgagtg 60
tgtgagggcg ctgcgtcctc cctgctcccc ttggagttgc cctttcttgc tcagatctgg 120
gtgccttggc cttgtcctgg gcccttccgc agcccccggg gtgatccccg ctag 174

<210> SEQ ID NO 278
<211> LENGTH: 19
<212> TYPE: DNA
<213> ORGANISM: Homo sapiens

<400> SEQUENCE: 278
ccagagcacc ccttctcag 19

<210> SEQ ID NO 279
<211> LENGTH: 18
<212> TYPE: DNA
<213> ORGANISM: Homo sapiens

<400> SEQUENCE: 279
ggaagggccc aggacaag 18

<210> SEQ ID NO 280
<211> LENGTH: 201
<212> TYPE: DNA
<213> ORGANISM: Homo sapiens

<400> SEQUENCE: 280
tatcttacgg atttgtcaac atcatttgag aagaagtcca taggctcagc agatttttat 60
gccaggtggg ccatggcata aaaatgtgaa gaatgtgctc acttagacaa tacctgtgct 120
aaaattggaa caatacagag aagattagca aattaaaaca atgttaggaa gtcagtgtgg 180
tgaggtacgg tgcctcatgc c 201

<210> SEQ ID NO 281
<211> LENGTH: 21
<212> TYPE: DNA
<213> ORGANISM: Homo sapiens

<400> SEQUENCE: 281
cagcagattt ttatgccagg t 21

<210> SEQ ID NO 282
<211> LENGTH: 20
<212> TYPE: DNA
<213> ORGANISM: Homo sapiens

<400> SEQUENCE: 282
caccgtacct caccacactg 20

<210> SEQ ID NO 283
<211> LENGTH: 275
<212> TYPE: DNA
<213> ORGANISM: Homo sapiens

<400> SEQUENCE: 283
aggcagggcc ctccttgcca catgtaaagc tgcacagagc ggtcactata tgtgtttcca 60
tatttgcaat ccaaccacca ccaactgagt gtgcgtcctg atcagccgag cctgcccacg 120
gtggccacag gccctctaca ttctaatctc gagagcctga gcatgtacaa attaaacgaa 180
gcaaaacgac accacccagt tctggccgta ctataggagg tttccaggaa gggtttgtga 240
acataaacat aagctaggta acactccttt ctgaa 275

<210> SEQ ID NO 284
<211> LENGTH: 20
<212> TYPE: DNA
<213> ORGANISM: Homo sapiens

<400> SEQUENCE: 284
aaccaccacc aactgagtgt 20

<210> SEQ ID NO 285
<211> LENGTH: 20
<212> TYPE: DNA
<213> ORGANISM: Homo sapiens

<400> SEQUENCE: 285
cctcctatag tacggccaga 20

<210> SEQ ID NO 286
<211> LENGTH: 230
<212> TYPE: DNA
<213> ORGANISM: Homo sapiens

<400> SEQUENCE: 286
tcagagcatc gcctcagtgg ccatcaatag ctcgggggac tggattgctt ttggctgttc 60
aggtttgtcc ccagcctggg tggtagagat ggactcccca ttagggacca gtgctgcccg 120
gctacaggct tacttgacag ccacccactg gggtgccct cccctccccc agttgtcttc 180
catggggtgc cctctccccc agccgccttt cagaaggggc cctcccctcc 230

<210> SEQ ID NO 287
<211> LENGTH: 20
<212> TYPE: DNA
<213> ORGANISM: Homo sapiens

<400> SEQUENCE: 287
tggattgctt ttggctgttc 20

<210> SEQ ID NO 288
<211> LENGTH: 20
<212> TYPE: DNA
<213> ORGANISM: Homo sapiens

<400> SEQUENCE: 288
caccccatgg aagacaactg 20

<210> SEQ ID NO 289
<211> LENGTH: 199
<212> TYPE: DNA
<213> ORGANISM: Homo sapiens

<400> SEQUENCE: 289
ctcatgctta catccttagc tgatcattaa actttgtgac catttcatgc tcactgcttt 60
cttgcccggg agctaatggt gaggaaaggt cactgggaac cagcgcacca acctcagaca 120
tcgattttgt tccagccttt tttcctgggc aggggtggct atcacctgct ggtaggcagc 180
ggcaggccca ctgtcctgc 199

<210> SEQ ID NO 290
<211> LENGTH: 21
<212> TYPE: DNA
<213> ORGANISM: Homo sapiens

<400> SEQUENCE: 290
ttaaactttg tgaccatttc a 21

<210> SEQ ID NO 291
<211> LENGTH: 18
<212> TYPE: DNA
<213> ORGANISM: Homo sapiens

<400> SEQUENCE: 291
taccagcagg tgatagcc 18

<210> SEQ ID NO 292
<211> LENGTH: 181
<212> TYPE: DNA
<213> ORGANISM: Homo sapiens

<400> SEQUENCE: 292
tgacagaaaa gtctcagagc agtgccttct gagctcttct acaccaagca ggcagaatgt 60
tcactgctaa tgaggctgga gctggtcccc agcagtggta ggaagcttcc aacaggctca 120
ggctgtgggt gcttgcaggg gcacagtgtg acggccacgg gcctcagagc tctggtgggc 180
t 181

<210> SEQ ID NO 293
<211> LENGTH: 20
<212> TYPE: DNA
<213> ORGANISM: Homo sapiens

<400> SEQUENCE: 293
gacagaaaag tctcagagca 20

<210> SEQ ID NO 294
<211> LENGTH: 18
<212> TYPE: DNA
<213> ORGANISM: Homo sapiens

<400> SEQUENCE: 294
caagcaccca cagcctga 18

<210> SEQ ID NO 295
<211> LENGTH: 187

<212> TYPE: DNA
<213> ORGANISM: Homo sapiens

<400> SEQUENCE: 295
acatctttct caaataaaga taacagcgat gtattttcac aaaagcaaga gcttagaaag 60
tactccaccc aggtatccct cttggaaaaa atacttaagg aaatatgaca aatggcaaag 120
tgattgttat ggatggaatg tttgtatcct cccaaaattc acatgttgag accctaattc 180
caatatg 187

<210> SEQ ID NO 296
<211> LENGTH: 20
<212> TYPE: DNA
<213> ORGANISM: Homo sapiens

<400> SEQUENCE: 296
attttcacaa aagcaagagc 20

<210> SEQ ID NO 297
<211> LENGTH: 20
<212> TYPE: DNA
<213> ORGANISM: Homo sapiens

<400> SEQUENCE: 297
ttgggaggat acaaacattc 20

<210> SEQ ID NO 298
<211> LENGTH: 180
<212> TYPE: DNA
<213> ORGANISM: Homo sapiens

<400> SEQUENCE: 298
aggggcattc tacaaaacac ccaaccggtc aaggtcgctg aggccaagga gagattgggc 60
aaccgtcaca aaccagagaa gccgaggaga cctttcagcc aacgccatgt ggggtcctga 120
gcaggaccca ccggaagttg gtgcagctgc ctaaagaccg tcctggctga gaagaaacag 180

<210> SEQ ID NO 299
<211> LENGTH: 18
<212> TYPE: DNA
<213> ORGANISM: Homo sapiens

<400> SEQUENCE: 299
aaggagagat tgggcaac 18

<210> SEQ ID NO 300
<211> LENGTH: 19
<212> TYPE: DNA
<213> ORGANISM: Homo sapiens

<400> SEQUENCE: 300
gtttcttctc agccaggac 19

<210> SEQ ID NO 301
<211> LENGTH: 228
<212> TYPE: DNA
<213> ORGANISM: Homo sapiens

<400> SEQUENCE: 301
tggccctgac ctgccagagc tgttggcctc cagctggcgg gtaaaaccca cggccttctc 60
agaacaggtt tctcaacaca tgagacagaa cacaccagac ttccaagggg aacacctgga 120

```
tggagctggt tacccagatc gttcaacacc gaggggcagc ggcttgaggg tctttccacg    180

aaggcttgga ttaacaagag gagcasrggt ctctccagga tgggccca                228

<210> SEQ ID NO 302
<211> LENGTH: 20
<212> TYPE: DNA
<213> ORGANISM: Homo sapiens

<400> SEQUENCE: 302

catgagacag aacacaccag                                                20

<210> SEQ ID NO 303
<211> LENGTH: 20
<212> TYPE: DNA
<213> ORGANISM: Homo sapiens

<400> SEQUENCE: 303

tcttgttaat ccaagccttc                                                20

<210> SEQ ID NO 304
<211> LENGTH: 223
<212> TYPE: DNA
<213> ORGANISM: Homo sapiens

<400> SEQUENCE: 304

ccacccagtg tcacgtcacg gccccggcac gccatccacg gaccctggat ggagcccagc    60

tgcctccagg agcgcagttt aactacaaag gagccctggc tgcccgcccc gcccagacgc   120

actgacctgt tgttctctgt ggctgctgat ggcccatccc caaccactgg tgactcttcc   180

ctggggcccc aagctcagcc cctaaccccc tgttgctgga agt                     223

<210> SEQ ID NO 305
<211> LENGTH: 18
<212> TYPE: DNA
<213> ORGANISM: Homo sapiens

<400> SEQUENCE: 305

cacggaccct ggatggag                                                  18

<210> SEQ ID NO 306
<211> LENGTH: 18
<212> TYPE: DNA
<213> ORGANISM: Homo sapiens

<400> SEQUENCE: 306

cagggaagag tcaccagt                                                  18

<210> SEQ ID NO 307
<211> LENGTH: 186
<212> TYPE: DNA
<213> ORGANISM: Homo sapiens

<400> SEQUENCE: 307

cagaggactg ggctgcgggg tcaggaatgg gcacacttcc taactgcagg acactctaag    60

ggctttggtc atgcacacgc agccaagaga aggtgtcgct gacacacagc cttccaggag   120

cggacttgga gacctcgcca aggaccagga ctccccagca ctcacactcc cttaggcgct   180

gaagtc                                                              186

<210> SEQ ID NO 308
<211> LENGTH: 20
```

<212> TYPE: DNA
<213> ORGANISM: Homo sapiens

<400> SEQUENCE: 308
actctaaggg ctttggtcat 20

<210> SEQ ID NO 309
<211> LENGTH: 20
<212> TYPE: DNA
<213> ORGANISM: Homo sapiens

<400> SEQUENCE: 309
ctaagggagt gtgagtgctg 20

<210> SEQ ID NO 310
<211> LENGTH: 185
<212> TYPE: DNA
<213> ORGANISM: Homo sapiens

<400> SEQUENCE: 310
gaagaggaca acacggggct gtctgcagag cacctgccac gcgccaggct ctgtgtccac 60
aagcacggcg gctgctccca catgacagag ctcgtgcggc agctccagga ctgtctggtg 120
ccagagcccc agctctccgc cagccccagg ccactgtgcg aggccctcag tgaagagggg 180
gccgt 185

<210> SEQ ID NO 311
<211> LENGTH: 18
<212> TYPE: DNA
<213> ORGANISM: Homo sapiens

<400> SEQUENCE: 311
cgccaggctc tgtgtcca 18

<210> SEQ ID NO 312
<211> LENGTH: 18
<212> TYPE: DNA
<213> ORGANISM: Homo sapiens

<400> SEQUENCE: 312
ggccccctct tcactgag 18

<210> SEQ ID NO 313
<211> LENGTH: 173
<212> TYPE: DNA
<213> ORGANISM: Homo sapiens

<400> SEQUENCE: 313
tctaaataat gttaatgatc aaatttagtc agatctcaat cttcatatgt tagttgcctt 60
cttaataaat attctgtttt ctttatcgtt ctttatttgt atctccacct tcatttctga 120
ttaaattaag aagttttgtc tcttccattt aataattaat gtatttaata acc 173

<210> SEQ ID NO 314
<211> LENGTH: 22
<212> TYPE: DNA
<213> ORGANISM: Homo sapiens

<400> SEQUENCE: 314
tttagtcaga tctcaatctt ca 22

<210> SEQ ID NO 315

<211> LENGTH: 22
<212> TYPE: DNA
<213> ORGANISM: Homo sapiens

<400> SEQUENCE: 315
aatggaagag acaaaacttc tt 22

<210> SEQ ID NO 316
<211> LENGTH: 194
<212> TYPE: DNA
<213> ORGANISM: Homo sapiens

<400> SEQUENCE: 316
cacactccac actggcccca cgcgggtggc gaaggactca gccagagcct ggcaggatcc 60
tggggtgtct atttccaagg aatgttctgg aagaaacata cacacatact tgtttgccag 120
atttacctgt gtggtcttcc agatgagaag cagcctgtgt cactccataa gggagagtgc 180
gtgcagcatt gaga 194

<210> SEQ ID NO 317
<211> LENGTH: 18
<212> TYPE: DNA
<213> ORGANISM: Homo sapiens

<400> SEQUENCE: 317
gaaggactca gccagagc 18

<210> SEQ ID NO 318
<211> LENGTH: 20
<212> TYPE: DNA
<213> ORGANISM: Homo sapiens

<400> SEQUENCE: 318
ctctccctta tggagtgaca 20

<210> SEQ ID NO 319
<211> LENGTH: 225
<212> TYPE: DNA
<213> ORGANISM: Homo sapiens

<400> SEQUENCE: 319
aagaaactcc caaggaacgc attgtcccaa gttgctgcac cagtcagtgt acattcccac 60
aaacagtgca tgagagttcc tgttgcttgt gaaataaatg gtcagcattc agtgttgtca 120
gcttttaaaa ttttctcctt tctagtgggc atgtaatggt ctcacattat agttttaatt 180
tgcattttcc tggtgacatg tgatacggaa ccttcctccc atgct 225

<210> SEQ ID NO 320
<211> LENGTH: 19
<212> TYPE: DNA
<213> ORGANISM: Homo sapiens

<400> SEQUENCE: 320
accagtcagt gtacattcc 19

<210> SEQ ID NO 321
<211> LENGTH: 19
<212> TYPE: DNA
<213> ORGANISM: Homo sapiens

<400> SEQUENCE: 321
ggaaaatgca aattaaaac 19

<210> SEQ ID NO 322
<211> LENGTH: 170
<212> TYPE: DNA
<213> ORGANISM: Homo sapiens

<400> SEQUENCE: 322
gtgcaattta attacaaacg cttaaatggg gaggtcaggg gcagagggat gatgtcacaa 60
acacacccac gtgtgcttgg tgcaaaacag taaaacaaac agcaagaagg tccatgaagg 120
aaagatcgcc tctgtcagtg ggagtaatga gagtggctga tggacaggtg 170

<210> SEQ ID NO 323
<211> LENGTH: 20
<212> TYPE: DNA
<213> ORGANISM: Homo sapiens

<400> SEQUENCE: 323
cgcttaaatg gggaggtcag 20

<210> SEQ ID NO 324
<211> LENGTH: 20
<212> TYPE: DNA
<213> ORGANISM: Homo sapiens

<400> SEQUENCE: 324
cctgtccatc agccactctc 20

<210> SEQ ID NO 325
<211> LENGTH: 189
<212> TYPE: DNA
<213> ORGANISM: Homo sapiens

<400> SEQUENCE: 325
acgccaagca ggagatgcca gacacagagt ccatcctgag agagtctgtt cctgtccaag 60
ctcagaaaca caggaagcca cctgtgctgt agcagcacac ggagatgcat cctttctggt 120
ccaccccacg gccctcattg cagtcaggga tcctctccca gaaagtccct gctgccagcc 180
cctgcccctt 189

<210> SEQ ID NO 326
<211> LENGTH: 20
<212> TYPE: DNA
<213> ORGANISM: Homo sapiens

<400> SEQUENCE: 326
agcaggagat gccagacaca 20

<210> SEQ ID NO 327
<211> LENGTH: 20
<212> TYPE: DNA
<213> ORGANISM: Homo sapiens

<400> SEQUENCE: 327
ggtggaccag aaaggatgca 20

<210> SEQ ID NO 328
<211> LENGTH: 170
<212> TYPE: DNA
<213> ORGANISM: Homo sapiens

<400> SEQUENCE: 328

```
catgagaaag actttgttcc catgagaaca acaagagaaa ctcaaacaaa attaaaattg     60

tacttttcta aaagaccggg gtgggggtcg tggtcaggca gcagcatgaa gaaagccttg    120

agaactgaat tccagaaaga aacaagcata ggcaagaaag agagatgaca               170


<210> SEQ ID NO 329
<211> LENGTH: 22
<212> TYPE: DNA
<213> ORGANISM: Homo sapiens

<400> SEQUENCE: 329

cccatgagaa caacaagaga aa                                              22


<210> SEQ ID NO 330
<211> LENGTH: 20
<212> TYPE: DNA
<213> ORGANISM: Homo sapiens

<400> SEQUENCE: 330

ctctttcttg cctatgcttg                                                 20


<210> SEQ ID NO 331
<211> LENGTH: 167
<212> TYPE: DNA
<213> ORGANISM: Homo sapiens

<400> SEQUENCE: 331

aagatttaga acagctgaag cagcgagaaa aaacccagca tgagtcagaa ctggagcaac     60

tgaggattta ttttgaaaag aagttaaggg atgctgagaa aacttaccaa gaagacctaa    120

ccctgttaca gcagaggctg cagggggcga gggaagatgc tcttctg                  167


<210> SEQ ID NO 332
<211> LENGTH: 21
<212> TYPE: DNA
<213> ORGANISM: Homo sapiens

<400> SEQUENCE: 332

cagctgaagc agcgagaaaa a                                               21


<210> SEQ ID NO 333
<211> LENGTH: 19
<212> TYPE: DNA
<213> ORGANISM: Homo sapiens

<400> SEQUENCE: 333

cccctgcagc ctctgctgt                                                  19


<210> SEQ ID NO 334
<211> LENGTH: 174
<212> TYPE: DNA
<213> ORGANISM: Homo sapiens

<400> SEQUENCE: 334

gggaaactga cttggctttt gcaagggtca ttgcttcctg atgcatgttt aactgtcctg     60

tgttcacttt gttgccgcag gtttttagag gaacgtaaag agatcaccga gaaattcagt    120

gcggaacaag atgccttcct gcaggaggcc caggagcagc atgcccgtga gctg          174


<210> SEQ ID NO 335
<211> LENGTH: 22
<212> TYPE: DNA
<213> ORGANISM: Homo sapiens
```

<400> SEQUENCE: 335
gggaaactga cttggctttt gc 22

<210> SEQ ID NO 336
<211> LENGTH: 20
<212> TYPE: DNA
<213> ORGANISM: Homo sapiens

<400> SEQUENCE: 336
ggcatcttgt tccgcactga 20

<210> SEQ ID NO 337
<211> LENGTH: 175
<212> TYPE: DNA
<213> ORGANISM: Homo sapiens

<400> SEQUENCE: 337
ccctgcacac tgacctgcat gccctcgtca cctgcactct gcatgctcac catctgacgg 60
actcctgcga cgggcatggg aaggtcgccg ccgccggcag ccttgcgagc actttggatg 120
tgtgcacccg gcatgccagg cccgagtcaa cagactggcc gaccttggcg tcctg 175

<210> SEQ ID NO 338
<211> LENGTH: 20
<212> TYPE: DNA
<213> ORGANISM: Homo sapiens

<400> SEQUENCE: 338
gccctcgtca cctgcactct 20

<210> SEQ ID NO 339
<211> LENGTH: 20
<212> TYPE: DNA
<213> ORGANISM: Homo sapiens

<400> SEQUENCE: 339
ccaaggtcgg ccagtctgtt 20

<210> SEQ ID NO 340
<211> LENGTH: 155
<212> TYPE: DNA
<213> ORGANISM: Homo sapiens

<400> SEQUENCE: 340
tttattgctg agtggtattc cattttatgg gtccattata gtttatttgt ccagacactt 60
catggaaaga catcagtgtt tcctgttttt caatcataaa ttgatgttta attttaaaat 120
tttggaattg tagaagaaat gcaattcttt tttcc 155

<210> SEQ ID NO 341
<211> LENGTH: 22
<212> TYPE: DNA
<213> ORGANISM: Homo sapiens

<400> SEQUENCE: 341
tgggtccatt atagtttatt tg 22

<210> SEQ ID NO 342
<211> LENGTH: 22
<212> TYPE: DNA
<213> ORGANISM: Homo sapiens

<400> SEQUENCE: 342
tgcatttctt ctacaattcc aa 22

<210> SEQ ID NO 343
<211> LENGTH: 208
<212> TYPE: DNA
<213> ORGANISM: Homo sapiens

<400> SEQUENCE: 343
ctttggtgca gaatcatgct gcaggcaagg tgggcccacc tccctggaat ttcatccccc 60
ccgtcagtta aacccatggt ggttttattt tctaggccac ctgatctggg aggaccacct 120
ccaagaaaag cagtcctatc gatgaacggt ctaagttatg gtgttatcag agtggatact 180
gaagaaaagt tgtcagtcct tactgttc 208

<210> SEQ ID NO 344
<211> LENGTH: 20
<212> TYPE: DNA
<213> ORGANISM: Homo sapiens

<400> SEQUENCE: 344
ggcccacctc cctggaattt 20

<210> SEQ ID NO 345
<211> LENGTH: 22
<212> TYPE: DNA
<213> ORGANISM: Homo sapiens

<400> SEQUENCE: 345
tccactctga taacaccata ac 22

<210> SEQ ID NO 346
<211> LENGTH: 232
<212> TYPE: DNA
<213> ORGANISM: Homo sapiens

<400> SEQUENCE: 346
atcacctggt ttggtgcatc ctcgcagaaa gagagccata cagtgaagtg gaaacacacc 60
caaaagctct gcaatattcc tagaagttct cgaatctcct ccttaacaga gctgcagaag 120
ggaaacacag acaggaagca cctgtttgac tcagacagca gccctaatgc agtgccactc 180
aggagcattc cctcatttga agaccccccca attacatgaa attatcaacc cc 232

<210> SEQ ID NO 347
<211> LENGTH: 20
<212> TYPE: DNA
<213> ORGANISM: Homo sapiens

<400> SEQUENCE: 347
acacccaaaa gctctgcaat 20

<210> SEQ ID NO 348
<211> LENGTH: 20
<212> TYPE: DNA
<213> ORGANISM: Homo sapiens

<400> SEQUENCE: 348
caaatgaggg aatgctcctg 20

<210> SEQ ID NO 349
<211> LENGTH: 240
<212> TYPE: DNA
<213> ORGANISM: Homo sapiens

<400> SEQUENCE: 349
ggaactgcag gagatccctg ctgccttcca gttcatggga tgatggcctc cacttctgcc 60
cctgtttgct tctcctttca aatcttacat gaaggtatac agtttgaaga agccagtttg 120
actccaatat ctgtgcaatg gaatactgct cattaaaaag gaattaaact attgatacac 180
acaacatggg tgaagatcaa actgtctcct tccctttgat tcaagggaat ctgagaaatg 240

<210> SEQ ID NO 350
<211> LENGTH: 19
<212> TYPE: DNA
<213> ORGANISM: Homo sapiens

<400> SEQUENCE: 350
acttctgccc ctgtttgct 19

<210> SEQ ID NO 351
<211> LENGTH: 21
<212> TYPE: DNA
<213> ORGANISM: Homo sapiens

<400> SEQUENCE: 351
tgatcttcac ccatgttgtg t 21

<210> SEQ ID NO 352
<211> LENGTH: 187
<212> TYPE: DNA
<213> ORGANISM: Homo sapiens

<400> SEQUENCE: 352
tggagaaagt tgttgcaaac tgcccagaga ccctgggagt cactccagtt ttctgaaacc 60
cagatatttc agtgcctcag gagagacaag tcctgacctt ctctcctcca gctctcccag 120
gagataggca agcccctaac tccctaacta agcccttcag acctgaaatc cattgagtgg 180
cttcttt 187

<210> SEQ ID NO 353
<211> LENGTH: 18
<212> TYPE: DNA
<213> ORGANISM: Homo sapiens

<400> SEQUENCE: 353
gcaaactgcc cagagacc 18

<210> SEQ ID NO 354
<211> LENGTH: 20
<212> TYPE: DNA
<213> ORGANISM: Homo sapiens

<400> SEQUENCE: 354
ttagggagtt aggggcttgc 20

<210> SEQ ID NO 355
<211> LENGTH: 184
<212> TYPE: DNA
<213> ORGANISM: Homo sapiens -continued

<400> SEQUENCE: 355

```
agggccatgg gatgatgcag gtggagactg gagtgctaca gctgcaagca aatacatttc     60

tgtgctgtga agccacccat ttggtggtac tacgttaaaa cagctctagg aaattaatac    120

agatgttgcc tgtatttttg tttctcatat tactactcat tgttttaatg atgactgttt    180

tatt                                                                 184
```

<210> SEQ ID NO 356
<211> LENGTH: 20
<212> TYPE: DNA
<213> ORGANISM: Homo sapiens

<400> SEQUENCE: 356

```
aggtggagac tggagtgcta                                                 20
```

<210> SEQ ID NO 357
<211> LENGTH: 22
<212> TYPE: DNA
<213> ORGANISM: Homo sapiens

<400> SEQUENCE: 357

```
agaaacaaaa atacaggcaa ca                                              22
```